United States Patent [19]

Iwasawa et al.

[11] Patent Number: 5,919,786
[45] Date of Patent: Jul. 6, 1999

[54] N,N-DISUBSTITUTED AMIC ACID DERIVATIVES

[75] Inventors: Yoshikazu Iwasawa; Tetsuya Aoyama; Kumiko Kawakami; Sachie Arai; Toshihiko Satoh; Yoshiaki Monden, all of Tsukuba, Japan

[73] Assignee: Banyu Pharmaceutical Co., Ltd., Tokyo, Japan

[21] Appl. No.: 09/047,311

[22] Filed: Mar. 25, 1998

Related U.S. Application Data

[60] Division of application No. 08/616,464, Mar. 15, 1996, Pat. No. 5,849,747, which is a continuation-in-part of application No. PCT/JP95/01589, Aug. 10, 1995.

[30] Foreign Application Priority Data

Aug. 12, 1994 [JP] Japan ...................................... 6-212147

[51] Int. Cl.⁶ .................. A61K 31/505; A61K 31/44; C07D 239/26; C07D 213/02
[52] U.S. Cl. .................. 514/256; 514/350; 514/355; 514/364; 514/365; 514/371; 514/372; 514/374; 514/378; 514/406; 514/427; 514/444; 514/465; 514/471; 514/533; 514/539; 514/570; 514/332; 544/332; 546/290; 546/309; 548/204; 548/214; 548/235; 548/247; 548/338.1; 548/571; 548/572; 549/58; 549/435; 549/487; 560/21; 562/443; 562/444; 562/449; 562/450
[58] Field of Search ..................... 514/256, 350, 514/416, 355, 364, 427, 371, 444, 465, 471, 533, 539, 570, 365, 372, 378, 374, 397; 544/332; 546/291, 309; 549/58, 435, 487; 560/21; 562/443, 444, 449, 480; 548/204, 214, 235, 247, 338.1, 571, 572

[56] References Cited

U.S. PATENT DOCUMENTS 5,260,465 11/1993 Singh et al. .
5,340,828 8/1994 Graham et al. .
5,488,149 1/1996 Nomoto et al. .

FOREIGN PATENT DOCUMENTS 0 535 730 4/1993 European Pat. Off. .
0 547 670 6/1993 European Pat. Off. .
0 776 884 6/1997 European Pat. Off. .
5-213992 8/1993 Japan .
5-279290 10/1993 Japan .
WO 97/01275 1/1997 WIPO .

*Primary Examiner*—Yogendra N. Gupta
*Attorney, Agent, or Firm*—Oblon, Spivak, McClelland, Maier & Neustadt, P.C.

[57] ABSTRACT

The present invention relates to a compound of the formula (I):

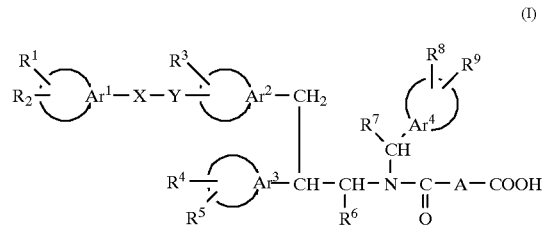

wherein $Ar^1$, $Ar^2$, $Ar^3$ and $Ar^4$ represent an aryl group or a heteroaromatic ring group; A represents a hydrocarbon group which may be substituted; X and Y represent an oxygen atom, a sulfur atom, a carbonyl group or a group of the formula —$CHR^a$— (wherein $R^a$ is a hydrogen atom or a lower alkyl group) or —$NR^b$— (wherein $R^b$ is a hydrogen atom or a lower alkyl group), or X and Y together represent a vinylene group or an ethynylene group; $R^1$, $R^2$, $R^3$, $R^8$ and $R^9$ represent a hydrogen atom, a halogen atom, a hydroxyl group, a lower alkyl group or a lower alkoxy group; $R^4$ and $R^5$ represent a hydrogen atom, a halogen atom, a hydroxyl group, an amino group, a nitro group, a cyano group, a carboxyl group, a lower alkoxycarbonyl group, a carbamoyl group, a lower alkylcarbamoyl group, a lower alkyl group, a lower hydroxyalkyl group, a lower fluoroalkyl group or a lower alkoxy group, $R^6$ is a lower alkyl group, and $R^7$ is a hydrogen atom or a lower alkyl group, provided that when one of X and Y is an oxygen atom, a sulfur atom or a group of the formula —$NR^b$—, the other is a carbonyl group or a group of the formula —$CHR^a$—, its pharmaceutically acceptable salt or ester, and an antitumor agent containing it as an active ingredient.

14 Claims, No Drawings

N,N-DISUBSTITUTED AMIC ACID DERIVATIVES

This application is a division of application Ser. No. 08/616,464, filed Mar. 15, 1996, now U.S. Pat. No. 5,849,747, which is a continuation-in-part of PCT/J195/01589 filed Aug. 10, 1995.

TECHNICAL FIELD

The present invention relates novel N,N-disubstituted amic acid derivatives. More particularly, the N,N-disubstituted amic acid derivatives of the present invention inhibit protein-farnesyl transferase (PFT) in vivo thereby to suppress function of oncogene protein Ras and thus present antitumor activities, and they are thus useful as antitumor agents.

BACKGROUND ART

The ras oncogene is activated by mutation, and its translation product Ras protein plays an important role in transformation of normal cells to cancer cells. Such activation of ras oncogene is observed in many cancers such as colorectal cancers or pancreatic cancers, and an proportion thereof is said to reach about 25% of the total human cancers. Accordingly, it is expected that canceration can be suppressed and antitumor effects can be obtained by suppressing such activation of ras oncogene, by inhibiting the function of Ras protein as its product.

Recently, it has been found that farnesyl-modification of Ras protein itself is essential for function of Ras protein, and it is possible to suppress localization of Ras protein at the plasma membrane by inhibiting this farnesyl-modification and thereby to inhibit transformation to cancer cells. The protein-farnesyl transferase (PFT) is an enzyme which catalyses this farnesyl-modification of Ras protein, and by inhibiting this enzyme, it is possible to suppress function of carcinogenic Ras protein. Further, this enzyme contributes to farnesyl-modification of only very limited proteins in vivo. Accordingly, the inhibitor for such an enzyme is expected to be a safe and highly selective antitumor agent. From such a viewpoint, many PFT inhibitors have been developed in recent years (Cell, vol. 57, p. 1167–1177 (1989); Proc. Natl. Acad. Sci., vol. 86, p. 8323–8327 (1989); ditto, vol. 90, p. 2281–2285 (1993); Science, vol. 245, p. 379–385 (1989); ditto, vol. 260, p. 1934–1937 (1993); ditto, vol. 260, p. 1937–1942 (1993); J. Biol. Chem., vol. 266, p. 15575–15578 (1991); J. Antibiotics, vol. 46, p. 222–227 (1993); Japanese Unexamined Patent Publications No. 201869/1993 and No. 213992/1993).

However, up to now, all of the reported PFT inhibitors have had some problems for development as medicines, such that the activities are low in cells, and the effects in vivo are inadequate.

DISCLOSURE OF INVENTION

It is an object of the present invention to provide a novel antitumor agent which inhibits the protein-farnesyl transferase (PFT) thereby to inhibit functional manifestation of oncogene protein Ras and which thus provides antitumor effects.

The present inventors have found that a compound of the formula (I):

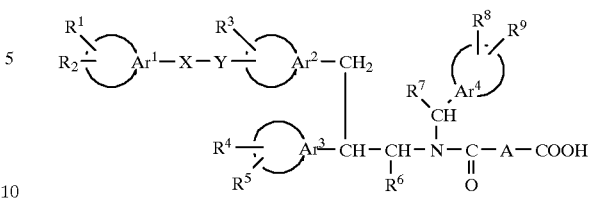

wherein each of

which are the same or different, is an aryl group or a heteroaromatic ring group; A is a $C_{2-8}$ saturated or unsaturated aliphatic hydrocarbon group which may have substituent(s) selected from the group consisting of a lower alkyl group, a hydroxyl group, a lower hydroxyalkyl group, a lower alkoxy group, a carboxyl group, a lower carboxyalkyl group, an aryl group and an aralkyl group; each of X and Y which are the same or different, is an oxygen atom, a sulfur atom, a carbonyl group or a group of the formula —CHR$^a$— (wherein R$^a$ is a hydrogen atom or a lower alkyl group) or —NR$^{b'}$ (wherein R$^b$ is a hydrogen atom or a lower alkyl group), or X and Y together represent a vinylene group or an ethynylene group; each of R$^1$, R$^2$, R$^3$, R$^8$ and R$^9$ which are the same or different, is a hydrogen atom, a halogen atom, a hydroxyl group, a lower alkyl group or a lower alkoxy group; each of R$^4$ and R$^5$ which are the same or different, is a hydrogen atom, a halogen atom, a hydroxyl group, an amino group, a nitro group, a cyano group, a carboxyl group, a lower alkoxycarbonyl group, a carbamoyl group, a lower alkylcarbamoyl group, a lower alkyl group, a lower hydroxyalkyl group, a lower fluoroalkyl group or a lower alkoxy group; R$^6$ is a lower alkyl group; and R$^7$ is a hydrogen atom or a lower alkyl group, provided that when one of X and Y is an oxygen atom, a sulfur atom or a group of the formula —NR$^b$— (wherein R$^b$ is as defined above), the other is a carbonyl group or a group of the formula —CHR$^a$— (wherein R$^a$ is as defined above), inhibits the protein-farnesyl transferase (PFT) thereby to suppress function of oncogene protein Ras, and thus is useful as an antitumor agent. The present invention has been accomplished on the basis of this discovery.

Thus, the present invention relates to a compound of the formula (I) or its pharmaceutically acceptable salt or ester, as well as its application as an antitumor agent.

Symbols and terms used in this specification will be explained.

The aryl group means a phenyl group, a naphthyl group or an anthryl group. A phenyl group or a naphthyl group is preferred.

The heteroaromatic ring group means a 5-membered or 6-membered monocyclic aromatic heterocyclic group containing one or two heteroatoms, which are the same or different, selected from the group consisting of an oxygen atom, a nitrogen atom and a sulfur atom, or a fused aromatic heterocyclic group having such a monocyclic aromatic heterocyclic group fused with the above-mentioned aryl group or having the same or different such monocyclic aromatic heterocyclic groups fused with each other, which may, for example, be a pyrrolyl group, an imidazolyl group, a pyrazolyl group, a pyridyl group, a pyrazinyl group, a pyrimidinyl group, a pyridazinyl group, an oxazolyl group, an isoxazolyl group, a furyl group, a thienyl group, a thiazolyl group, an isothiazolyl group, an indolyl group, a benzofuranyl group, a benzothienyl group, a benzimidazolyl group, a benzoxazolyl group, a benzisoxazolyl group, a benzothiazolyl group, a benzisothiazolyl group, an indazolyl group, a purinyl group, a quinolyl group, an isoquinolyl group, a phthalazinyl group, a naphthylidinyl group, a quinoxalinyl group, a quinazolinyl group, a cinnolinyl group or a pteridinyl group. Among them, a furyl group, a thienyl group, a pyridyl group, a pyrimidinyl group, an oxazolyl group, an isoxazolyl group, a thiazolyl group, a benzofuranyl group, a benzothienyl group, a benzimidazolyl group, a benzoxazolyl group, a benzothiazolyl group or a quinolyl group is preferred.

The lower alkyl group means a $C_{1-6}$ linear or branched alkyl group, which may, for example, be a methyl group, an ethyl group, a propyl group, an isopropyl group, a butyl group, a sec-butyl group, a tert-butyl group, a pentyl group or a hexyl group. Among them, a methyl group or an ethyl group is preferred.

The lower hydroxyalkyl group means the above-mentioned lower alkyl group having a hydroxyl group, i.e. a $C_{1-6}$ hydroxyalkyl group, such as a hydroxymethyl group, a hydroxyethyl group, a hydroxypropyl group or a hydroxybutyl group. Among them, a hydroxymethyl group or a hydroxyethyl group is preferred.

The lower alkoxy group means a $C_{1-6}$ alkoxy or alkylenedioxy group, which may, for example, be a methoxy group, an ethoxy group, a propoxy group, an isopropoxy group, a butoxy group, a tert-butoxy group, a methylenedioxy group, an ethylenedioxy group or a trimethylenedioxy group. Among them, a methoxy group, an ethoxy group or a methylenedioxy group is preferred.

The lower carboxyalkyl group means the above-mentioned lower alkyl group having a carboxyl group, i.e. a $C_{1-7}$ carboxyalkyl group, such as a carboxymethyl group, a carboxyethyl group, a carboxypropyl group or a carboxybutyl group. Among them, a carboxymethyl group or a carboxyethyl group is preferred.

The aralkyl group means the above-mentioned lower alkyl group having the above-mentioned aryl group, such as a benzyl group, a phenethyl group, a 3-phenylpropyl group, a 1-naphthylmethyl group, a 2-naphthylmethyl group or a 1-(2-naphthyl)ethyl group. Among them, a benzyl group, a phenethyl group or a 2-naphthylmethyl group is preferred.

The saturated aliphatic hydrocarbon group may, for example, be an ethylene group, a trimethylene group, a tetramethylene group, a pentamethylene group, a hexamethylene group, a heptamethylene group or an octamethylene group. For example, a trimethylene group, a tetramethylene group or a pentamethylene group is preferred.

The unsaturated aliphatic hydrocarbon group means an unsaturated aliphatic hydrocarbon group having one or more, preferably one or two double bonds, at optional position(s) on the carbon chain, which may, for example, be a vinylene group, a propenylene group, a 1-butenylene group, a 2-butenylene group, a 1,3-butadienylene group, a 1-pentenylene group, a 2-pentenylene group, a 1,3-pentadienylene group, a 1,4-pentadienylene group, a 1-hexenylene group, a 2-hexenylene group, a 3-hexenylene group, a 1,3-hexadienylene group, a 1,4-hexadienylene group, a 1,5-hexadienylene group, a 1,3,5-hexatrienylene group, a 1-heptenylene group, a 2-heptenylene group, a 3-heptenylene group, a 1,3-heptadienylene group, a 1,4-heptadienylene group, a 1,5-heptadienylene group, a 1,6-heptadienylene group, a 1,3,5-heptatrienylene group, a 1-octenylene group, a 2-octenylene group, a 3-octenylene group, a 4-octenylene group, a 1,3-octadienylene group, a 1,4-octadienylene group, a 1,5-octadienylene group, a 1,6-octadienylene group, a 1,7-octadienylene group, a 2,4-octadienylene group, a 2,5-octadienylene group, a 2,6-octadienylene group, a 3,5-octadienylene group, a 1,3,5-octatrienylene group, a 2,4,6-octatrienylene group or a 1,3,5,7-octatetraenylene group. Among them, a propenylene group, a 1-butenylene group, a 1,3-butadienylene group or a 1-pentenylene group is preferred.

The halogen atom may be a fluorine atom, a chlorine atom, a bromine atom or an iodine atom. For example, a fluorine atom or a chlorine atom is preferred.

The lower alkoxycarbonyl group means a $C_{1-7}$ alkoxycarbonyl group, such as a methoxycarbonyl group, an ethoxycarbonyl group, a propoxycarbonyl group, a butoxycarbonyl group or a tert-butoxycarbonyl group. Among them, a methoxycarbonyl group or an ethoxycarbonyl group is preferred.

The lower alkylcarbamoyl group means a carbamoyl group mono-substituted or di-substituted by the above-mentioned lower alkyl group, such as a methylcarbamoyl group, an ethylcarbamoyl group, a dimethylcarbamoyl group or a diethylcarbamoyl group.

The lower fluoroalkyl group means the above-mentioned lower alkyl group having fluorine atom(s), i.e. a $C_{1-6}$ fluoroalkyl group, such as a fluoromethyl group, a difluoromethyl group, a trifluoromethyl group, a 1-fluoroethyl group, a 2-fluoroethyl group, a 2,2,2-trifluoroethyl group or a pentafluoroethyl group.

The salt of the compound of the formula (I) may be a pharmaceutically acceptable common salt, which may, for example, be a base-addition salt of the terminal carboxyl group or of a carboxyl group when $R^4$ and/or $R^5$ is a carboxyl group, or when a carboxyl group or a lower carboxyalkyl group is present on a saturated or unsaturated aliphatic hydrocarbon group represented by A in the formula (I), or an acid-addition salt of an amino group when $R^4$ and/or $R^5$ is an amino group, or of a basic heteroaromatic ring when such a basic heteroaromatic ring is present.

The base-addition salt may, for example, be an alkali metal salt such as a sodium salt or a potassium salt; an alkaline earth metal salt such as a calcium salt or a magnesium salt; an ammonium salt; or an organic amine salt such as a trimethylamine salt, a triethylamine salt, a dicyclohexylamine salt, an ethanolamine salt, a diethanolamine salt, a triethanolamine salt, a procaine salt or an N,N'-dibenzylethylenediamine salt.

The acid-addition salt may, for example, be an inorganic acid salt such as a hydrochloride, a sulfate, a nitrate, a phosphate or a perchlorate; an organic acid salt such as a maleate, a fumarate, a tartrate, a citrate, an ascorbate or a trifluoroacetate; or a sulfonic acid salt such as a methanesulfonate, an isethionate, a benzenesulfonate or a p-toluenesulfonate.

The ester of the compound of the formula (I) means a pharmaceutically acceptable common ester of the terminal carboxyl group or of a carboxyl group when $R^4$ and/or $R^5$ is a carboxyl group, or when a carboxyl group or a lower carboxyalkyl group is present on the saturated or unsaturated aliphatic hydrocarbon group represented by A in the formula (I). It may, for example, be an ester with a lower alkyl group such as a methyl group, an ethyl group, a propyl group, an isopropyl group, a butyl group, a sec-butyl group, a tert-butyl group, a cyclopropyl group or a cyclopentyl group, an ester with an aralkyl group such as a benzyl group or a phenethyl group, an ester with a lower alkenyl group such as an allyl group or a 2-butenyl group, an ester with a lower alkoxyalkyl group such as a methoxymethyl group, a 2-methoxyethyl group or a 2-ethoxyethyl group, an ester with a lower alkanoyloxyalkyl group such as an acetoxymethyl group, a pivaloyloxymethyl group or a 1-pivaloyloxyethyl group, an ester with a lower alkoxycarbonylalkyl group such as a methoxycarbonylmethyl group or an isopropoxycarbonylmethyl group, an ester with a lower carboxyalkyl group such as a carboxymethyl group, an ester with a lower alkoxycarbonyloxyalkyl group such as a 1-(ethoxycarbonyloxy)ethyl group or a 1-(cyclohexyloxycarbonyloxy)ethyl group, an ester with a lower carbamoyloxyalkyl group such as a carbamoyloxymethyl group, an ester with a phthalidyl group, or an ester with a (5-substituted-2-oxo-1,3-dioxol-4-yl)methyl group such as a (5-methyl-2-oxo-1,3-dioxol-4-yl)methyl group.

Further, when a hydroxyl group is present at the γ- or δ-position of the terminal carboxyl group or of a carboxyl group when such a carboxyl group or a lower carboxyalkyl group is present on the saturated or unsaturated aliphatic hydrocarbon group represented by A in the formula (I), such a hydroxyl group and a carboxyl group may form an intramolecular ester i.e. a 5-membered or 6-membered lactone ring.

Further, the compound of the present invention may have stereoisomers such as optical isomers, diastereomers or geometrical isomers, depending upon the form of its substituents. The compound of the present invention includes all of such stereoisomers and their mixtures. Among them, a compound of the formula (I-1):

is a phenyl group and a compound wherein

is a naphthyl group, a benzofuranyl group or a benzothienyl group, are preferred.

Each of X and Y which are the same or different, is an oxygen atom, a sulfur atom, a carbonyl group or a group of the formula —CHR$^a$— (wherein R$^a$ is a hydrogen atom or a lower alkyl group) or —NR$^b$— (wherein R$^b$ is a hydrogen atom or a lower alkyl group), or X and Y together represent a vinylene group or an ethynylene group. However, when one of X and Y is an oxygen atom, a sulfur atom or a group of the formula —NR$^b$— (wherein R$^b$ is as defined above), the other is a carbonyl group or a group of the formula —CHR$^a$— (wherein R$^a$ is as defined above).

Referring to the formula (I), a compound wherein X is —NR$^b$— (wherein R$^b$ is as defined above), and Y is a carbonyl group, a compound wherein X is an oxygen atom, and Y is —CHR$^a$— (wherein R$^a$ is as defined above), a compound wherein each of X and Y is a group of the formula —CHR$^a$— (wherein R$^a$ is as defined above), or a compound wherein X and Y together represent a vinylene group, is preferred.

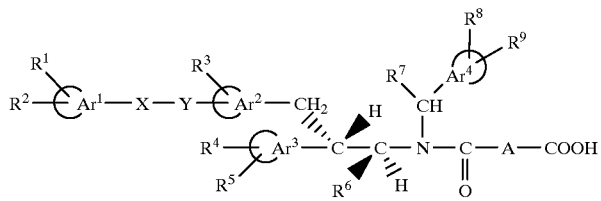

or the formula (I-2):

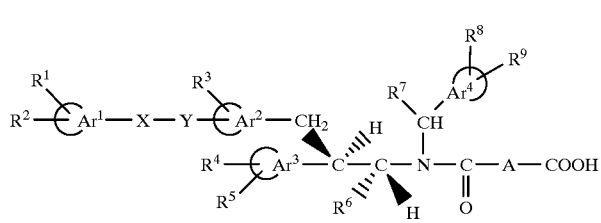

wherein

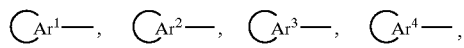

A, X, Y, R$^1$, R$^2$, R$^3$, R$^4$, R$^5$, R$^6$, R$^7$, R$^8$ and R$^9$ are as defined above, is preferred.

Among compounds of the formula (I), a compound wherein

The $C_{2-8}$ saturated or unsaturated aliphatic hydrocarbon group which may have substituent(s) selected from the group consisting of a lower alkyl group, a hydroxyl group, a lower hydroxyalkyl group, a lower alkoxy group, a carboxyl group, a lower carboxyalkyl group, an aryl group and an aralkyl group, for A in the compound of the formula (I), means the above-mentioned saturated aliphatic hydrocarbon group or the above-mentioned unsaturated aliphatic hydrocarbon group, which is unsubstituted or which may have substituent(s) at optional position(s) for substitution. Such substituent(s) may be one or more, preferably from one to three members, which are the same or different, selected from the group consisting of a lower alkyl group, a hydroxyl group, a lower hydroxyalkyl group, a lower alkoxy group, a carboxyl group, a lower carboxyalkyl group, an aryl group and an aralkyl group.

Preferred is a compound wherein A is a group of the formula (a):

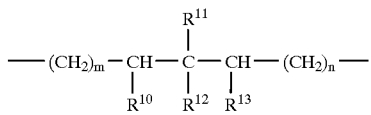

wherein $R^{10}$ is a hydrogen atom, a hydroxyl group, a lower hydroxyalkyl group, a lower alkoxy group or a carboxyl group; $R^{11}$ is a hydrogen atom, a hydroxyl group, a lower alkoxy group, a carboxyl group or a lower carboxyalkyl group; $R^{12}$ is a hydrogen atom, a lower hydroxyalkyl group or a carboxyl group; $R^{13}$ is a hydrogen atom, a hydroxyl group or a carboxyl group; and each of m and n which are the same or different, is an integer of from 0 to 2, or a compound wherein A is a group of the formula (b):

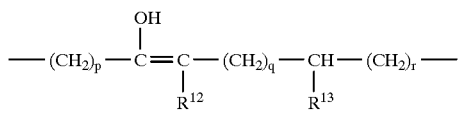

wherein $R^{12}$ is a hydrogen atom, a lower hydroxyalkyl group or a carboxyl group; $R^{13}$ is a hydrogen atom, a hydroxyl group or a carboxyl group; p is 0 or 1; and each of q and r which are the same or different, is an integer of from 0 to 2.

When A is a group of the formula (a), $R^{10}$ is preferably a hydrogen atom, a hydroxyl group or a carboxyl group, $R^{11}$ is preferably a carboxyl group or a lower carboxyalkyl group such as a carboxymethyl group, each of $R^{12}$ and $R^{13}$ is preferably a hydrogen atom or a carboxyl group, and each of m and n which are the same or different, is preferably 0 or 1.

When A is a group of the formula (b), $R^{12}$ is preferably a lower hydroxyalkyl group such as a hydroxymethyl group, or a carboxyl group, and $R^{13}$ is preferably a hydrogen atom, and each of p, q and r is preferably 0.

Further, it is well known that in the case of a compound having a partial structure of the formula (b), there exist enol form and keto form tautomers, as shown below. The compound of the present invention includes such enol form and keto form isomers and their mixtures.

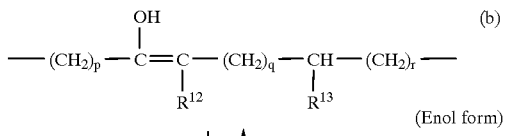

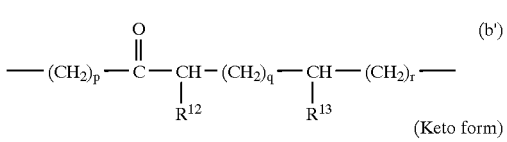

In the above formulas, $R^{12}$, $R^{13}$, p, q and r are as defined above.

Each of $R^1$ and $R^2$ which are the same or different, is a hydrogen atom, a halogen atom, a hydroxyl group, a lower alkyl group or a lower alkoxy group, and may be substituted at an optional position for substitution on the aryl group or the heteroaromatic ring group represented by the formula

$R^3$ is a hydrogen atom, a halogen atom, a hydroxyl group, a lower alkyl group or a lower alkoxy group, and may be substituted at an optional position for substitution on the aryl group or the heteroaromatic ring group represented by the formula

Further, in the formula (I), the group of the formula

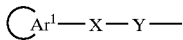

may also be substituted at an optional position for substitution on the above-mentioned aryl or the heteroaromatic ring group in the same manner as $R^3$.

Each of $R^4$ and $R^5$ which are the same or different, is a hydrogen atom, a halogen atom, a hydroxyl group, an amino group, a nitro group, a cyano group, a carboxyl group, a lower alkoxycarbonyl group, a carbamoyl group, a lower alkylcarbamoyl group, a lower alkyl group, a lower hydroxyalkyl group, a lower fluoroalkyl group or a lower alkoxy group. Each of them may be substituted at an optional position for substitution on the aryl or heteroaromatic ring group represented by the formula

$R^6$ is preferably a methyl group, an ethyl group or a propyl group. Particularly preferred is a methyl group or an ethyl group.

$R^7$ is preferably a hydrogen atom, a methyl group, an ethyl group or a propyl group. Particularly preferred is a hydrogen atom or a methyl group.

Each of $R^8$ and $R^9$ which are the same or different, is a hydrogen atom, a halogen atom, a hydroxyl group, a lower alkyl group or a lower alkoxy group, and each of them may be substituted at an optional position for substitution on the aryl or heteroaromatic ring group represented by the formula

Now, processes for producing the compound of the present invention will be described.

The compound of the formula (I) of the present invention can be prepared, for example, by the following process 1, 2, 3, 4, 5 or 6.

Process 1

The compound of the formula (I) can be prepared by reacting a compound of the formula (II):

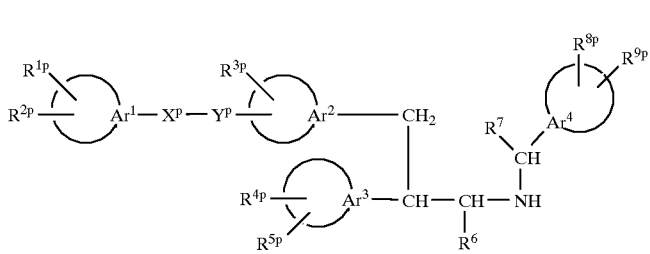

(II)

wherein each of

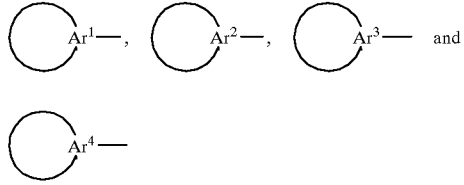

and

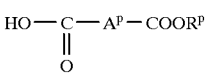

which are the same or different, is an aryl group or a heteroaromatic ring group; each of $X^p$ and $Y^p$ which are the same or different, is an oxygen atom, a sulfur atom, a carbonyl group or a group of the formula —$CHR^a$— (wherein $R^a$ is a hydrogen atom or a lower alkyl group) or —$NR^{bp}$— (wherein $R^{bp}$ is a hydrogen atom, a lower alkyl group or an imino-protecting group), or $X^p$ and $Y^p$ together represent a vinylene group or an ethynylene group; each of $R^{1p}$, $R^{2p}$, $R^{3p}$, $R^{8p}$ and $R^{9p}$ which are the same or different, is a hydrogen atom, a halogen atom, a hydroxyl group which may be protected, a lower alkyl group or a lower alkoxy group; each of $R^{4p}$ and $R^{5p}$ which are the same or different, is a hydrogen atom, a halogen atom, a nitro group, a cyano group, a lower alkoxycarbonyl group, a carbamoyl group, a lower alkylcarbamoyl group, a lower alkyl group, a lower fluoroalkyl group, a lower alkoxy group or a hydroxyl, amino, carboxyl or lower hydroxyalkyl group which may be protected; $R^6$ is a lower alkyl group; and $R^7$ is a hydrogen atom or a lower alkyl group, provided that when one of $X^p$ and $Y^p$ is an oxygen atom, a sulfur atom or a group of the formula —$NR^{bp}$— (wherein $R^{bp}$ is as defined above), the other is a carbonyl group or a group of the formula —$CHR^a$— (wherein $R^a$ is as defined above), with a carboxylic acid of the formula (III) or its reactive derivative:

$$HO-\underset{\underset{O}{\|}}{C}-A^p-COOR^p \qquad (III)$$

wherein $A^p$ is a $C_{2-8}$ saturated or unsaturated aliphatic hydrocarbon group which may have substituent(s) selected from the group consisting of a lower alkyl group, a lower alkoxy group, an aryl group, an aralkyl group, and hydroxyl, lower hydroxyalkyl, carboxyl and lower carboxyalkyl groups which may be protected; and $R^p$ is a hydrogen atom or a carboxyl-protecting group, to obtain a compound of the formula (IV):

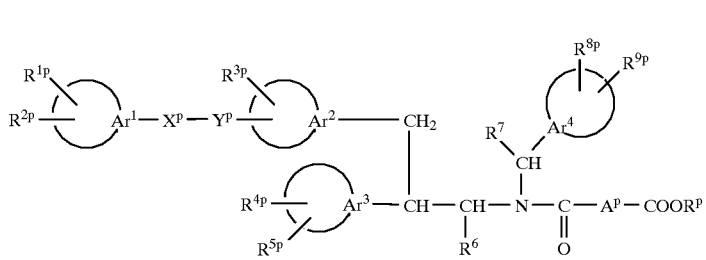

(IV)

wherein

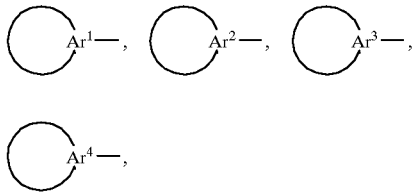

$A^p, X^p, Y^p, R^{1p}, R^{2p}, R^{3p}, R^{4p}, R^{5p}, R^6, R^7, R^{8p}, R^{9p}$ and $R^p$ are as defined above, and, if necessary, removing any protecting group.

As the reactive derivative of the carboxylic acid of the formula (III), an acid halide, a mixed acid anhydride, an active ester or an active amide may, for example, be used.

When the carboxylic acid of the formula (III) is used, it is preferred to conduct the reaction in the presence of a condensing agent such as N,N'-dicyclohexylcarbodiimide, 1-ethyl-3-(3-dimethylaminopropyl)carbodiimide or 2-chloro-1,3-dimethylimidazolyl chloride.

The reaction of the compound of the formula (II) with the carboxylic acid of the formula (III) or its reactive derivative, is conducted usually by using 1 mol or an excess molar amount, preferably from 1 to 5 mols, of the carboxylic acid of the formula (III) or its reactive derivative, per mol of the compound of the formula (II).

The reaction is conducted usually in an inert solvent. The inert solvent may, for example, be a halogenated hydrocarbon such as methylene chloride, chloroform, carbon tetrachloride, dichloroethane or trichloroethylene; an ether such as ethyl ether, tetrahydrofuran or dioxane; an aromatic hydrocarbon such as benzene, toluene, chlorobenzene or xylene; an aprotic polar solvent such as dimethylformamide, acetonitrile, acetone, ethyl acetate or hexamethylphosphoric triamide, or a mixture of such solvents.

The reaction temperature is usually from −70° C. to the boiling point of the solvent used for the reaction, preferably from −20° C. to 100° C.

The reaction time is usually from 5 minutes to 7 days, preferably from 10 minutes to 24 hours.

The above reaction can be conducted in the presence of a base to facilitate the reaction.

As such a base, it is preferred to conduct the reaction in the presence of an inorganic base such as sodium hydroxide, potassium hydroxide, calcium hydroxide, sodium carbonate, potassium carbonate or sodium hydrogencarbonate, or an organic base such as triethylamine, N-ethyldiisopropylamine, pyridine, 4-dimethylaminopyridine or N,N-dimethylaniline.

Such a base is used usually in an amount of 1 mol or an excess molar amount, preferably from 1 to 5 mols, per mol of the reactive derivative of the carboxylic acid of the formula (III).

The acid halide of the compound of the formula (III) can be obtained by reacting the carboxylic acid of the formula (III) with a halogenating agent in accordance with a conventional method. As the halogenating agent, thionyl chloride, phosphorus trichloride, phosphorus pentachloride, phosphorus oxychloride, phosphorus tribromide, oxalyl chloride or phosgene may, for example, be used.

The mixed acid anhydride of the compound of the formula (III) can be obtained by reacting the carboxylic acid of the formula (III) with an alkyl chlorocarbonate such as ethyl chlorocarbonate or with an aliphatic carboxylic acid chloride such as acetyl chloride, in accordance with a conventional method. Further, an intramolecular acid anhydride may be formed between carboxyl groups at both terminals, or when in the formula (III), a carboxyl group is present on the saturated or unsaturated aliphatic hydrocarbon group for $A^p$, an intramolecular acid anhydride may be formed between such a carboxyl group and a carboxyl group to be involved in the reaction, to constitute a reactive derivative of the carboxylic acid.

The active ester of the compound of the formula (III) can be prepared by reacting the carboxylic acid of the formula (III) with an N-hydroxy compound such as N-hydroxysuccinimide, N-hydroxyphthalimide or 1-hydroxybenzotriazole, or a phenol compound such as a 4-nitrophenol, 2,4-dinitrophenol, 2,4,5-trichlorophenol or pentachlorophenol, in the presence of a condensing agent such as N,N'-dicyclohexylcarbodiimide or 1-ethyl-3-(3-dimethylaminopropyl)carbodiimide in accordance with a conventional method.

The active amide of the compound of the formula (III) can be prepared by reacting the carboxylic acid of the formula (III) with e.g. 1,1'-carbonyldiimidazole or 1,1'-carbonylbis (2-methylimidazole) in accordance with a conventional method.

When a hydroxyl group is present on the group of the formula

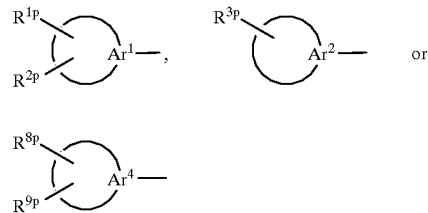

when a hydroxyl group, a lower hydroxyalkyl group, a carboxyl group or a lower carboxyalkyl group is present on the saturated or unsaturated aliphatic hydrocarbon group represented by $A^p$, and when a hydroxyl group, an amino group, a carboxyl group or a lower hydroxyalkyl group is present on the group of the formula

it is preferred to conduct the reaction after protecting such a hydroxyl group, a lower hydroxyalkyl group, an amino group, a carboxyl group or a lower carboxyalkyl group appropriately by a hydroxyl-protecting group, an amino-protecting group or a carboxyl-protecting group and removing the protecting group after the reaction. Further, in a case where one of $X^p$ and $Y^p$ is a group of the formula —$NR^{bp}$— (wherein $R^{bp}$ is as defined above), and the other is a group of the formula —$CHR^a$— (wherein $R^a$ is as defined above), $R^{bp}$ is preferably a lower alkyl group or an imino-protecting group, and when $R^{bp}$ is an imino-protecting group, it is preferred to remove such a protecting group after the reaction.

The hydroxyl-protecting group may, for example, be a lower alkylsilyl group such as a trimethylsilyl group or a tert-butyldimethylsilyl group; a lower alkoxymethyl group such as a methoxymethyl group or a 2-methoxyethoxymethyl group; a tetrahydropyranyl group; an aralkyl group such as a benzyl group, a p-methoxybenzyl group, a p-nitrobenzyl group or a trityl group; or an acyl group such as a formyl group or an acetyl group. Particularly preferred is a methoxymethyl group, a tetrahydropyranyl group, a trityl group, a tert-butyldimethylsilyl group or an acetyl group.

The amino- or imino-protecting group may, for example, be an aralkyl group such as a benzyl group, a p-methoxybenzyl group, a p-nitrobenzyl group, a benzhydryl group or a trityl group; a lower alkanoyl group such as a formyl group, an acetyl group, a propionyl group, a butyryl group or a pivaloyl group; a lower haloalkanoyl group such as a trifluoroacetyl group; a lower alkoxycarbonyl group such as a methoxycarbonyl group, an ethoxycarbonyl group, a propoxycarbonyl group or a tert-butoxycarbonyl group; a lower haloalkoxycarbonyl group such as a 2,2,2-trichloroethoxycarbonyl group; an alkenyloxycarbonyl group such as a 2-propenyloxycarbonyl group; an aralkyloxycarbonyl group such as a benzyloxycarbonyl group or a p-nitrobenzyloxycarbonyl group; or a lower alkylsilyl group such as a trimethylsilyl group or a tert-butyldimethylsilyl group. Further, the amino-protecting group may, for example, be an aralkylidene group such as a benzylidene group, a p-chlorobenzylidene group or a p-nitrobenzylidene group. Particularly preferred is an acetyl group, a trifluoroacetyl group, a tert-butoxycarbonyl group or a benzyloxycarbonyl group.

The carboxyl-protecting group may, for example, be a lower alkyl group such as a methyl group, an ethyl group, a propyl group, an isopropyl group or a tert-butyl group; a lower haloalkyl group such as a 2,2,2-trichloroethyl group; a lower alkenyl group such as 2-propenyl group; or an aralkyl group such as a benzyl group, a p-methoxybenzyl group, a p-nitrobenzyl group, a benzhydryl group or trityl group. Particularly preferred is a methyl group, an ethyl group, a tert-butyl group, a 2-propenyl group, a benzyl group, a p-methoxybenzyl group or a benzhydryl group.

After completion of the reaction, conventional treatment is conducted to obtain a crude product of the compound of the formula (IV). The compound of the formula (IV) may or may not be purified in accordance with a conventional method, and if necessary, reactions for removing protecting groups such as a hydroxyl group, an amino group and a carboxyl group, are appropriately conducted to obtain a compound of the formula (I).

Removal of protecting groups may vary depending upon their types, but can be conducted in accordance with the methods disclosed in a literature (Protective Groups in Organic Synthesis, T. W. Greene, John Wiley & Sons (1981)) or methods similar thereto, for example by solvolysis employing an acid or a base, by chemical reduction employing a metal hydride complex or by catalytic reduction employing a palladium-carbon catalyst or Raney nickel.

Process 2

A compound of the formula (I-a):

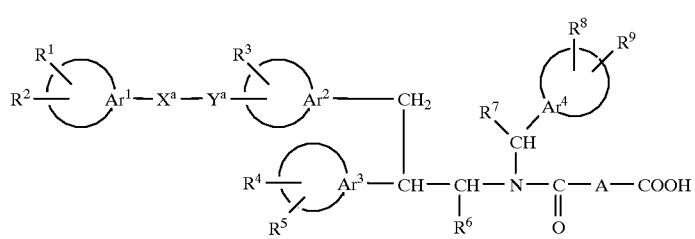

wherein

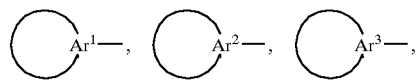

A, $R^1$, $R^2$, $R^3$, $R^4$, $R^5$, $R^6$, $R^7$, $R^8$ and $R^9$ are as defined above, and $X^a$ and $Y^a$ are as defined below, can be prepared by reacting a compound of the formula (V):

wherein $X^a$ is a carbonyl group or a group of the formula —$CHR^a$— (wherein $R^a$ is as defined above), Z is a leaving group; and

$R^{1p}$ and $R^{2p}$ are as defined above, with a compound of the formula (VI):

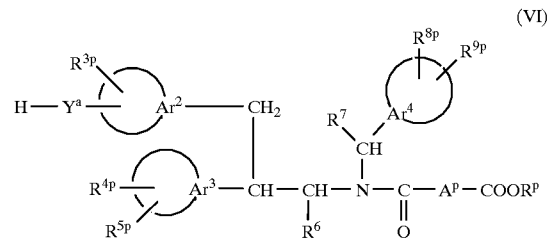

wherein $Y^a$ is an oxygen atom, a sulfur atom or a group of the formula —$NR^b$— (wherein $R^b$ is as defined above); and

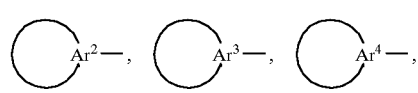

$A^p$, $R^{3p}$, $R^{4p}$, $R^{5p}$, $R^6$, $R^7$, $R^{8p}$, $R^{9p}$ and $R^p$ are as defined above, to obtain a compound of the formula (IV-a):

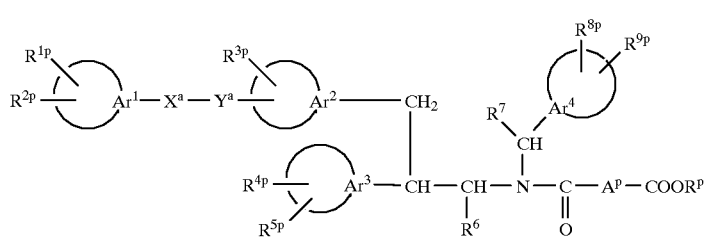

(IV-a)

wherein

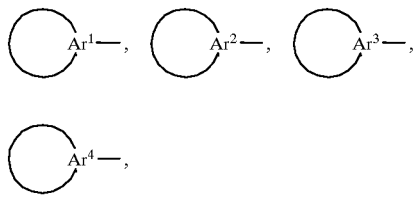

$A^p$, $X^a$, $Y^a$, $R^{1p}$, $R^{2p}$, $R^{3p}$, $R^{4p}$, $R^{5p}$, $R^6$, $R^7$, $R^{8p}$, $R^{9p}$ and $R^p$ are as defined above, and, if necessary, removing any protecting group.

Process 2 is a process for preparing a compound of the formula (I) wherein —X—Y— is a group of the formula —COO—, —COS—, —CONR$^b$—, —CHR$^a$O—, —CHR$^a$S— or —CHR$^a$NR$^b$— (wherein R$^a$ and R$^b$ are as defined above) i.e. a compound of the formula (I-a).

The reaction of the compound of the formula (V) with a compound of the formula (VI) is carried out usually by using 1 mol or an excess molar amount, preferably from 1 to 3 mols, of the compound of the formula (V), per mol of the compound of the formula (VI).

The reaction is conducted usually in an inert solvent. The inert solvent may, for example, be a halogenated hydrocarbon such as methylene chloride, chloroform, carbon tetrachloride, dichloroethane or trichloroethylene; an ether such as ethyl ether, tetrahydrofuran or dioxane; an aromatic hydrocarbon such as benzene, toluene, chlorobenzene or xylene; an aprotic polar solvent such as dimethylformamide, acetonitrile, acetone, ethyl acetate or hexamethylphosphoric triamide, or a mixture of such solvents.

The reaction temperature is usually from −70° C. to the boiling point of the solvent used for the reaction, preferably from −20° C. to 100° C.

The reaction time is usually from 5 minutes to 7 days, preferably from 10 minutes to 24 hours.

The above reaction is preferably conducted in the presence of a base to facilitate the reaction. Especially when Y$^a$ in the formula (VI) is not a group of the formula —NR$^b$—, it is necessary to carry out the reaction in the presence of an inorganic base such as sodium hydride, n-butyl lithium, sodium hydroxide, potassium hydroxide, calcium hydroxide, sodium carbonate, potassium carbonate or sodium hydrogencarbonate, or an organic base such as triethylamine, N-ethyldiisopropylamine, pyridine, 4-dimethylaminopyridine or N,N-dimethylaniline.

The base is used usually in an amount of 1 mol or an excess molar amount, preferably from 1 to 5 mols, per mol of the compound of the formula (V).

The leaving group represented by Z in the formula (V) may, for example, be a halogen atom such as a chlorine atom, a bromine atom or an iodine atom, or an organic sulfonyloxy group such as a methanesulfonyloxy group, a p-toluenesulfonyloxy group or a benzenesulfonyloxy group.

When a hydroxyl group is present on the group of the formula

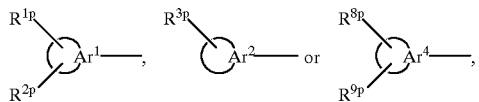

when a hydroxyl group, a lower hydroxyalkyl group, a carboxyl group or a lower carboxyalkyl group is present on the saturated or unsaturated aliphatic hydrocarbon group represented by A$^p$, and when a hydroxyl group, an amino group, a carboxyl group or a lower hydroxyalkyl group is present on the group of the formula

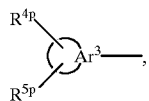

it is preferred to conduct the reaction after protecting such a hydroxyl group, a lower hydroxyalkyl group, an amino group, a carboxyl group or a lower carboxyalkyl group appropriately by a hydroxyl-protecting group, an amino-protecting group or a carboxyl-protecting group and removing any protecting group after the reaction.

The hydroxyl-protecting group, the amino-protecting group and the carboxyl-protecting group may be the protecting groups mentioned above with respect to process 1.

After completion of the reaction, a usual treatment is carried out to obtain a crude product of the compound of the formula (IV-a). The compound of the formula (IV-a) thus obtained may or may not be purified by a conventional method, and if necessary, reactions for removing the hydroxyl-, amino- and carboxyl-protecting groups may be carried out in a proper combination to obtain a compound of the formula (I-a).

The method for removing a protecting group varies depending upon the type of the protecting group and the stability of the desired compound (I-a). However, removal of protecting groups can be appropriately conducted in accordance with the methods disclosed in the above-mentioned literature or methods similar thereto.

Process 3

A compound of the formula (I-b):

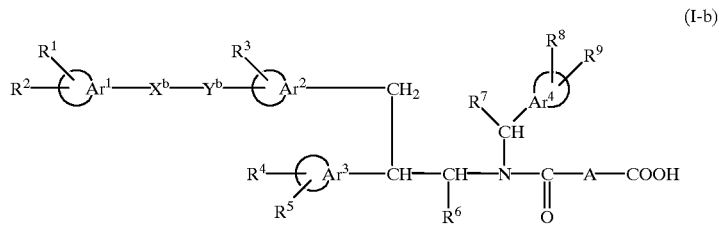
(I-b)

wherein

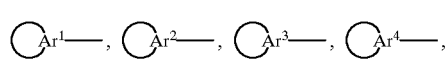

A, $R^1$, $R^2$, $R^3$, $R^4$, $R^5$, $R^6$, $R^7$, $R^8$ and $R^9$ are as defined above, and $X^b$ and $Y^b$ are as defined below, can be prepared by reacting a compound of the formula (VII):

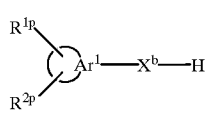
(VII)

wherein $X^b$ is an oxygen atom, a sulfur atom or a group of the formula —$NR^b$— (wherein $R^b$ is as defined above); and

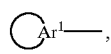

$R^{1p}$ and $R^{2p}$ are as defined above, with a compound of the formula (VIII):

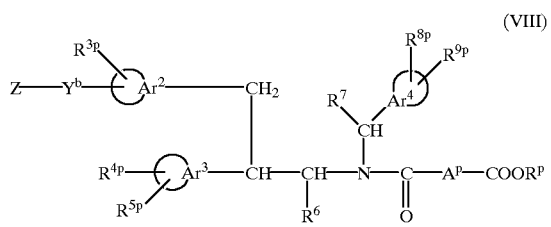
(VIII)

wherein $Y^b$ is a carbonyl group or a group of the formula —$CHR^a$— (wherein $R^a$ is as defined above); and

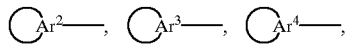

$A^p$, Z, $R^{3p}$, $R^{4p}$, $R^{5p}$, $R^6$, $R^7$, $R^{8p}$, $R^{9p}$ and $R^p$ are as defined above, to obtain a compound of the formula (IV-b):

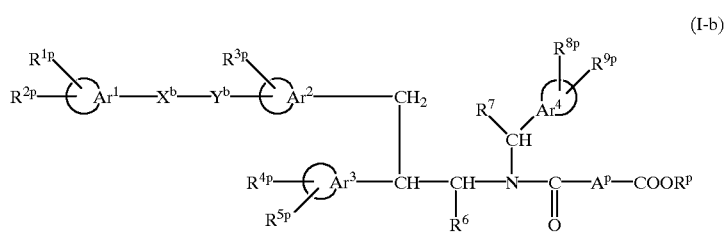
(I-b)

wherein

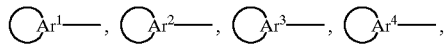

$A^p$, $X^b$, $Y^b$, $R^{1p}$, $R^{2p}$, $R^{3p}$, $R^{4p}$, $R^{5p}$, $R^6$, $R^7$, $R^{8p}$, $R^{9p}$ and $R^p$ are as defined above, and, if necessary, removing any protecting group.

Process 3 is a process for preparing a compound of the formula (I) wherein —X—Y— is a group of the formula —OCO—, —SCO—, —$NR^bCO$—, —$OCHR^a$—, —$SCHR^a$— or —$NR^bCHR^a$— (wherein $R^a$ and $R^b$ are as defined above) i.e. a compound of the formula (I-b).

This process can be conducted usually in an inert solvent, preferably in the presence of a base, by using 1 mol or an excess molar amount, preferably from 1 to 3 mols, of the compound of the formula (VII), per mol of the compound of the formula (VIII). The types of the inert solvent and the base as well as the reaction conditions may be the same as described above with respect to process 2. Accordingly, the reaction and the post-treatment after the reaction may preferably be carried out all in accordance with process 2.

Further, in the above processes 2 and 3, when $X^a$ or $Y^b$ is a carbonyl group, a compound wherein the group corresponding to Z is a hydroxyl group i.e. a compound wherein Z and the adjacent $X^a$ or $Y^b$ together represents a carboxyl group, can be used. In such a case, the reaction conditions, etc. are preferably in accordance with the reaction conditions for the reaction of the compound of the formula (II) with the compound of the formula (III) in the above process 1.

Process 4

A compound of the formula (I-c):

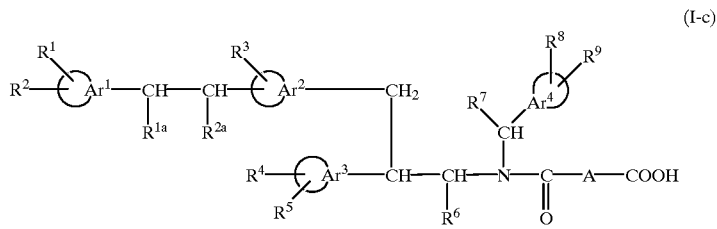

wherein

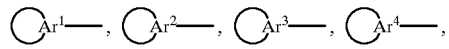

A, $R^1$, $R^2$, $R^3$, $R^4$, $R^5$, $R^6$, $R^7$, $R^8$ and $R^9$ are as defined above, and $R^{1a}$ and $R^{2a}$ are as defined below, can be prepared by reacting a compound of the formula (IX):

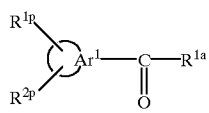

wherein $R^{1a}$ is a hydrogen atom or a lower alkyl group; and

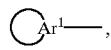

$R^{1p}$ and $R^{2p}$ are as defined above, with a compound of the formula (X):

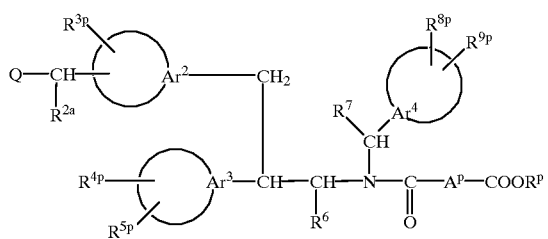

wherein Q is a triphenylphosphonio group, a dimethoxyphosphoryl group or a diethoxyphosphoryl group; $R^{2a}$ is a hydrogen atom or a lower alkyl group; and

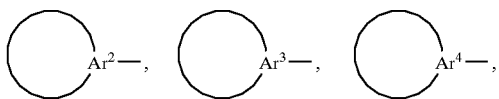

$A^p$, $R^{3p}$, $R^{4p}$, $R^5$, $R^6$, $R^7$, $R^{8p}$, $R^{9p}$ and $R^p$ are as defined above, to obtain a compound of the formula (XI):

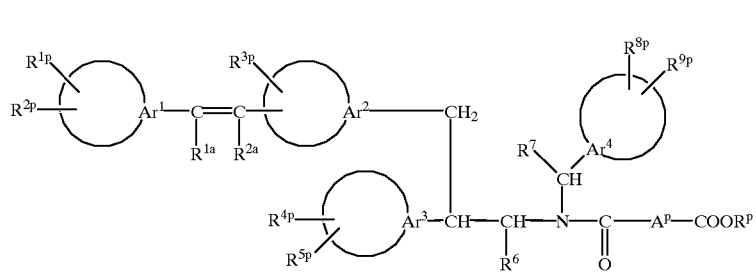

wherein

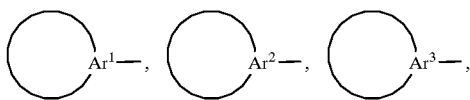

-continued

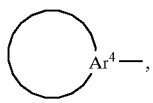

$A^p$, $R^{1p}$, $R^{2p}$, $R^{3p}$, $R^{4p}$, $R^{5p}$, $R^6$, $R^7$, $R^{8p}$, $R^{9p}$, $R^p$, $R^{1a}$ and $R^{2a}$ are as defined above, and, if necessary, removing any protecting group.

Process 4 is a process for preparing a compound of the formula (I) wherein —X—Y— is —CHR$^{1a}$CHR$^{2a}$— (wherein each of $R^{1a}$ and $R^{2a}$ which are the same or different, is a hydrogen atom or a lower alkyl group) i.e. a compound of the formula (I-c).

The reaction of the compound of the formula (IX) with a compound of the formula (X) is carried out usually by employing equimolar amounts of the two reactants or using a slightly excess amount of one of them.

The reaction is carried out usually in an inert solvent. Such an inert solvent may, for example, be an ether such as ethyl ether, tetrahydrofuran or dioxane; an aromatic hydrocarbon such as benzene, toluene, chlorobenzene or xylene; an aprotic polar solvent such as dimethylformamide, acetonitrile, acetone, ethyl acetate or hexamethylphosphoric triamide; or a mixture of such solvents.

The reaction temperature is usually from –100° C. to the boiling point of the solvent used for the reaction, preferably from –70° C. to 50° C.

The reaction time is usually from 5 minutes to 7 days, preferably from 10 minutes to 24 hours.

Further, the above reaction can be conducted in the presence of a base to facilitate the reaction. Especially when Q in the formula (X) is a triphenylphosphonio group, the reaction is preferably conducted in the presence of a base such as sodium hydride, n-butyl lithium, sodium methoxide, potassium tert-butoxide, sodium hydroxide or potassium hydroxide.

Such a base is used in an amount of 1 mol or an excess molar amount, preferably from 1 to 5 mols per mol of the compound wherein Q is a triphenylphosphonio group.

The reaction of reducing the compound of the formula (XI) obtained in the above step is usually preferably conducted by catalytic reduction employing a palladium-carbon catalyst, a Raney nickel catalyst or a platinum catalyst in an inert solvent.

The inert solvent may, for example, be an alcohol such as methanol, ethanol or propanol, or acetic acid.

The reaction temperature is usually from –20° C. to 100° C., preferably from 0° C. to room temperature.

The reaction time is usually from 5 minutes to 7 days, preferably from 10 minutes to 24 hours.

The hydrogen pressure in the catalytic reduction reaction is usually preferably from atmospheric pressure to 5 atm, and the amount of the catalyst is usually from 0.01 to 1 mol, preferably from 0.05 to 0.2 mol, per mol of the starting material compound (XI).

After completion of the reaction, the product is subjected to a usual treatment after removing any protecting group if such a protecting group is present or directly if no such protecting group is present, to obtain a compound of the formula (I-c).

Removal of the protecting group and the post treatment may be conducted by the methods described with respect to the above process 1.

Process 5

A compound of the formula (I-c):

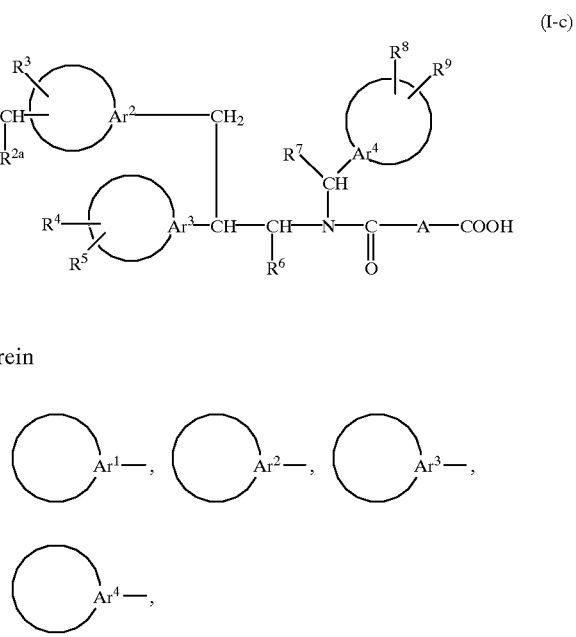

(I-c)

wherein

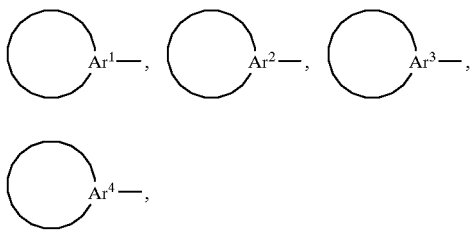

A, $R^1$, $R^2$, $R^3$, $R^4$, $R^5$, $R^6$, $R^7$, $R^8$, $R^9$, $R^{1a}$ and $R^{2a}$ are as defined above, can be obtained by reacting a compound of the formula (XII):

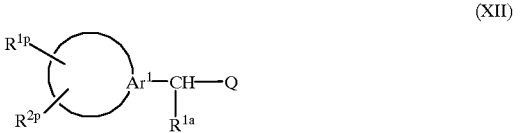

(XII)

wherein

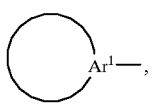

Q, $R^{1p}$, $R^{2p}$ and $R^{1a}$ are as defined above, with a compound of the formula (XIII):

(XIII)

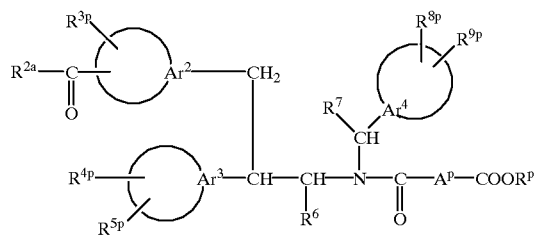

wherein

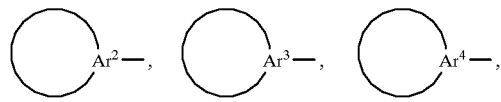

$A^p$, $R^{3p}$, $R^{4p}$, $R^{5p}$, $R^6$, $R^7$, $R^{8p}$, $R^{9p}$, $R^p$ and $R^{2a}$ are as defined above, to obtain a compound of the formula (XI):

(XI)

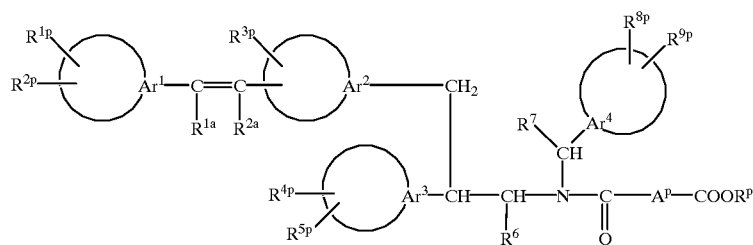

-continued

$A^p$, $R^{1p}$, $R^{2p}$, $R^{3p}$, $R^{4p}$, $R^{5p}$, $R^6$, $R^7$, $R^{8p}$, $R^{9p}$, $R^p$, $R^{1a}$ and $R^{2a}$ are as defined above, then reducing the compound of the formula (XI), and, if necessary, removing any protecting group.

Like process 4, process 5 is a process for producing a compound of the formula (I) wherein —X—Y— is —CHR$^{1a}$CHR$^{2a}$— (wherein $R^{1a}$ and $R^{2a}$ are as defined above) i.e. a compound of the formula (I-c).

Process 5 is equal to the reaction of process 4 wherein staring material compounds (IX) and (X) are replaced by the compounds (XIII) and (XII), respectively. Accordingly, the manner and conditions of the reaction may be all in accordance with process 4.

Further, a compound of the formula (I-d):

(I-d)

wherein

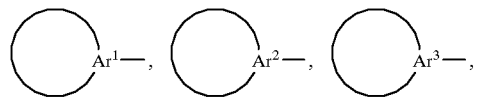

wherein

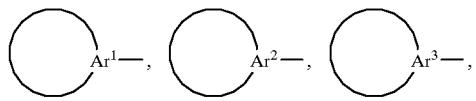

-continued

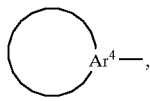

A, $R^1$, $R^2$, $R^3$, $R^4$, $R^5$, $R^6$, $R^7$, $R^8$ and $R^9$ are as defined above, can be obtained by removing a protecting group, as the case requires, from a compound of the formula (XI-a):

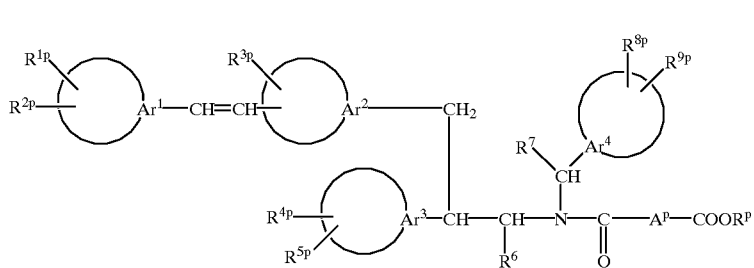

(XI-a)

wherein

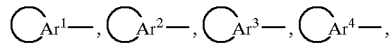

$A^p$, $R^{1p}$, $R^{2p}$, $R^{3p}$, $R^{4p}$, $R^{5p}$, $R^6$, $R^7$, $R^{8p}$, $R^{9p}$ and $R^p$ are as defined above, i.e. a compound of the formula (XI) wherein both $R^{1a}$ and $R^{2a}$ are hydrogen atoms, among compounds of the formula (XI) obtainable as intermediates in the above processes 4 and 5.

Process 6

A compound of the formula (I-e):

wherein

X, Y, $R^1$, $R^2$, $R^3$, $R^4$, $R^5$, $R^6$, $R^7$, $R^8$, $R^9$, $R^{12}$, $R^{13}$, p, q and r are as defined above, can be prepared by oxidizing a compound of the formula (IV-e):

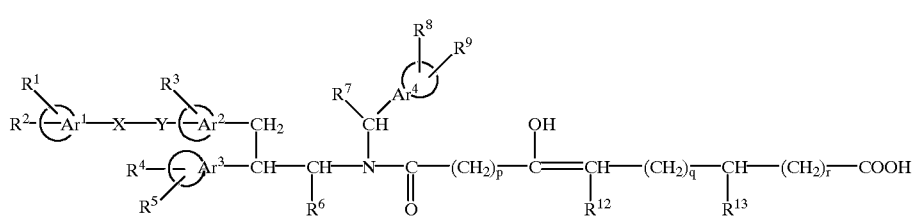

(I-e)

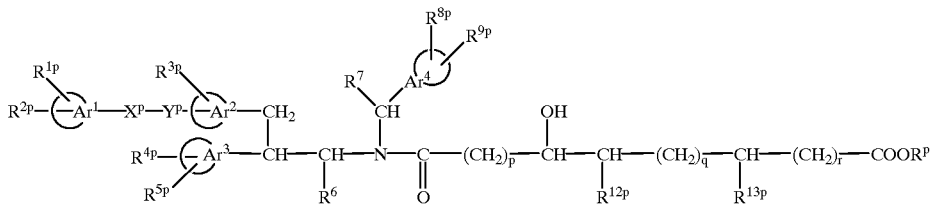

(IV-e)

wherein $R^{12p}$ is a hydrogen atom or a lower hydroxyalkyl or carboxyl group which may be protected, $R^{13p}$ is a hydrogen atom or a hydroxyl or carboxyl group which may be protected; and

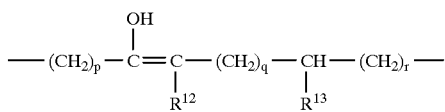

$X^p$, $Y^p$, $R^{1p}$, $R^{2p}$, $R^{3p}$, $R^{4p}$, $R^{5p}$, $R^6$, $R^7$, $R^{8p}$, $R^{9p}$, $R^p$, p, q and r are as defined above, and, if necessary, removing any protecting group.

Process 6 is a process for preparing a compound of the formula (I) wherein A is a group of the formula (b):

$$—(CH_2)_p—\underset{R^{12}}{C}=\underset{R^{13}}{\overset{OH}{C}}—(CH_2)_q—CH—(CH_2)_r—$$

(b)

wherein $R^{12}$, $R^{13}$, p, q and r are as defined above, i.e. a compound of the formula (I-e).

The reaction of oxidizing the compound of the formula (IV-e) is usually preferably carried out in an inert solvent by using so-called Dess-Martin oxidation employing 12-I-5 triacetoxyperiodinane; so-called Swern oxidation employing oxalyl chloride and dimethyl sulfoxide; a sulfur trioxide-pyridine complex; pyridinium chlorochromate; active manganese dioxide; or tetra-n-propylammonium perruthenate.

The inert solvent may, for example, be a halogenated hydrocarbon such as methylene chloride, chloroform or dichloroethane; an ether such as ethyl ether, tetrahydrofuran or dioxane; an aprotic polar solvent such as acetonitrile, acetone, ethyl acetate or dimethyl sulfoxide; or a mixture of such solvents.

The reaction temperature varies depending upon the type of the oxidizing agent, etc. However, it is usually from −100° C. to the boiling point of the solvent used for the reaction, preferably from −70° C. to 100° C.

The reaction time is usually from 5 minutes to 7 days, preferably from 10 minutes to 24 hours.

After completion of the reaction, the product is subjected to usual treatment after removing a protecting group when such a protecting group is present, or directly when no such protecting group is present, to obtain the compound of the formula (I-e).

The removal of the protecting group and the post-treatment may be conducted in the same manner as described above with respect to process 1.

Further, a compound corresponding to the compound of the formula (IV-e) to be used as the starting material in the above process 6, can be prepared, for example, by hydrolyzing a compound of the formula (IV-e-1):

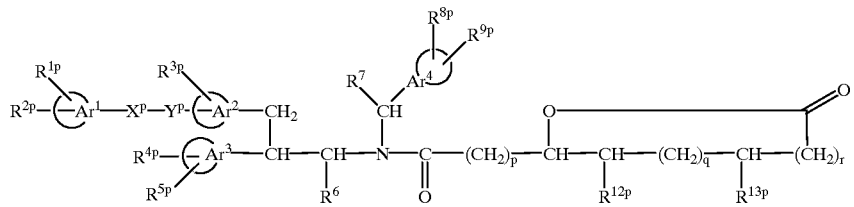

(IV-e-1)

wherein $$\bigcirc Ar^1—, \bigcirc Ar^2—, \bigcirc Ar^3—, \bigcirc Ar^4—,$$

$X^p$, $Y^p$, $R^{1p}$, $R^{2p}$, $R^{3p}$, $R^{4p}$, $R^{5p}$, $R^6$, $R^7$, $R^{8p}$, $R^{9p}$, $R^{12p}$, $R^{13p}$, p, q and r are as defined above, in the presence of a base, to obtain a compound of the formula (IV-e-2):

(IV-e-2)

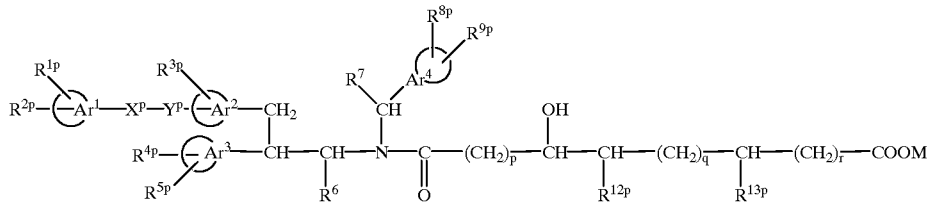

wherein M is a hydrogen atom or an alkali metal atom; and

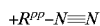

$X^p, Y^p, R^{1p}, R^{2p}, R^{3p}, R^{4p}, R^{5p}, R^6, R^7, R^{8p}, R^{9p}, R^{12p}, R^{13p}$, p, q and r are as defined above, then reacting thereto a diazo compound of the formula $+R^{pp}-N\equiv N$ wherein $R^{pp}$ is a lower alkyl group, a lower alkenyl group, an aralkyl group or a lower alkoxycarbonylalkyl group, or an alkylating agent of the formula $R^{pp}-Z^1$ wherein $R^{pp}$ and $Z^1$ are as defined above.

Isolation and purification of the compound of the formula (I), (I-a), (I-b), (I-c), (I-d) or (I-e), obtained by the above process can be conducted by a single use or a proper combination of conventional separating means such as column chromatography employing silica gel, adsorbent resin, etc., liquid chromatography, solvent extraction and recrystallization-reprecipitation.

The compound of the formula (I), (I-a), (I-b), (I-c), (I-d) or (I-e) can be converted to a pharmaceutically acceptable salt or ester by a conventional method. Reversely, the conversion from the salt or ester to a free carboxylic acid can also be conducted by a conventional method.

The compounds of the formulas (II), (III), (V), (VI), (VII), (VIII), (IX), (X), (XII) and (XIII) may be commercially available or can be prepared in accordance with the methods disclosed in literatures (J. Med. Chem., 10, 717 (1967); ibid., 725; J. Chem. Soc. Perkin I, 1636 (1978); Chem. Lett., 191 (1980); ibid., 375 (1984); J.

Chem. Soc. Chem. Commun., 579 (1984); J. Am. Chem. Soc., 104, 5716 (1982)) or methods similar thereto, or in accordance with the following processes or the methods disclosed in Reference Examples.

Process A

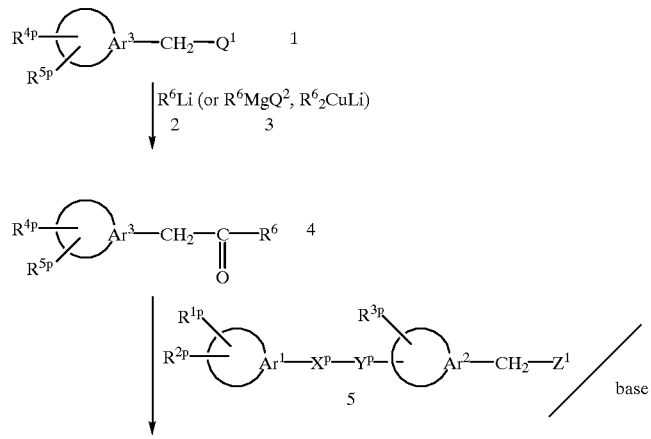

-continued

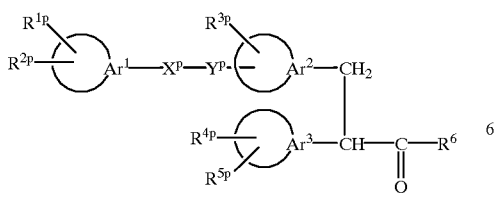

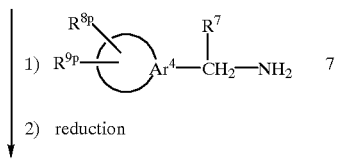 6

1) 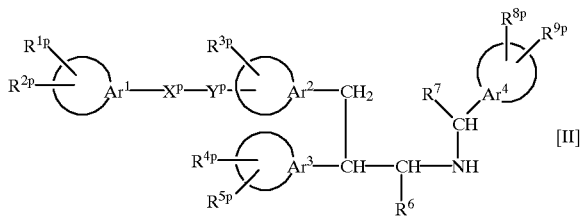 7

2) reduction

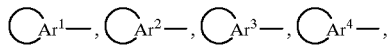 [II]

In the above formulas, $Q^1$ is a cyano group, a carboxyl group, a lower alkoxycarbonyl group, a chloroformyl group or an N-methoxy-N-methylcarbamoyl group; $Q^2$ is a halogen atom; $Z^1$ is a leaving group selected from the group consisting of a chlorine atom, a bromine atom, an iodine atom, a trifluoroacetoxy group, a methanesulfonyloxy group, a trifluoromethanesulfonyloxy group and a p-toluenesulfonyloxy group; and $$\bigcirc Ar^1-, \bigcirc Ar^2-, \bigcirc Ar^3-, \bigcirc Ar^4-,$$

$X^p$, $Y^p$, $R^{1p}$, $R^{2p}$, $R^{3p}$, $R^{4p}$, $R^{5p}$, $R^6$, $R^7$, $R^{8p}$ and $R^{9p}$ are as defined above.

By this process, the desired compound (II) can be prepared by reacting a nitrile or a carboxylic acid derivative of the formula 1 with an alkyl lithium of the formula 2 or an alkyl Grignard reagent (or an alkyl Gilman reagent) of the formula 3 to obtain a ketone compound 4, then reacting an alkylating agent of the formula 5 to the ketone compound 4 to produce a compound of the formula 6, then reacting the compound 6 with an amine compound of the formula 7, followed by reduction.

The above reaction steps will be described in detail referring to suitable reaction conditions, etc.

The first step of preparing the ketone compound 4 is conducted usually by reacting 1 mol or an excess molar amount, preferably from 1 to 5 mols of the alkyl lithium reagent 2 or the alkyl Grignard reagent (or the alkyl Gilman reagent in the case where the substituent $Q^1$ of the compound 1 is a chloroformyl group) 3 to 1 mol of the starting material compound 1 in a solvent inert to the reaction such as tetrahydrofuran, ethyl ether or benzene, if necessary followed by hydrolysis under an acidic condition.

The reaction temperature is usually from −80° C. to the boiling point of the solvent used for the reaction, preferably from −70° C. to 50° C. The reaction time is usually from 5 minutes to 48 hours, preferably from 30 minutes to 24 hours.

When the substituent $Q^1$ in the formula of the starting material compound 1 is a cyano group, it may be necessary to conduct a hydrolytic reaction under an acidic condition after completion of the reaction, and such a hydrolytic reaction is conducted in e.g. methanol, ethanol, tetrahydrofuran or a solvent mixture thereof with water in the presence of an acid such as hydrochloric acid, sulfuric acid or p-toluenesulfonic acid.

The reaction temperature is usually from 0° C. to the boiling point of the solvent used for the reaction, and the reaction time is from 30 minutes to 24 hours.

The step of preparing the compound of the formula 6 from the ketone compound 4, can be conducted by reacting an equimolar amount or an excess molar amount, preferably from 1 to 2 mols, of the alkylating agent of the formula 5 to the ketone compound 4 in the presence of a base in an inert solvent which does not adversely affect the reaction or without using any solvent.

The inert solvent may, for example, be an ether such as ethyl ether, tetrahydrofuran or dioxane; an aromatic hydrocarbon such as benzene, toluene or xylene; an aprotic polar solvent such as dimethylformamide, dimethyl sulfoxide or hexamethylphosphoric triamide, or a mixture of such solvents.

The base to be used for this reaction, may, for example, be an alkali metal hydride such as sodium hydride, lithium hydride or potassium hydride; a lithium amide such as lithium amide, lithium diisopropylamide or lithium bis(trimethylsilyl)amide; an alkyl lithium such as methyl lithium, butyl lithium or tert-butyl lithium; an alkali metal alkoxide such as sodium methoxide, sodium ethoxide or potassium tert-butoxide; or an alkali metal hydroxide such as sodium hydroxide, potassium hydroxide or lithium hydroxide.

The base is used usually in an amount of 1 mol or an excess molar amount, preferably from 1 to 5 mols, per mol of the starting material alkylating agent 5.

The reaction temperature is usually from −100° C. to the boiling point of the solvent used for the reaction, preferably from −80° C. to 100° C. The reaction time is usually from 10 minutes to 48 hours, preferably from 30 minutes to 24 hours.

The step of preparing the desired compound (II) from the compound of the formula 6 can be conducted usually in an inert solvent such as methanol, ethanol, benzene, ethyl ether or tetrahydrofuran by reacting 1 mol or an excess molar amount, preferably from 1 to 2 mols, of the amine compound of the formula 7 to 1 mol of the compound of the formula 6 to preliminarily form an imine, which is subsequently reduced.

The reaction temperature in the process for forming the above imine is usually from 0° C. to the boiling point of the solvent used for the reaction, preferably from room temperature to 100° C. The reaction time is usually from 5 minutes to 48 hours, preferably from 30 minutes to 24 hours. After the formation of the imine, the reaction solution may be used as it is to the subsequent step of the reduction reaction, or the reaction solution may be distilled or subjected to a conventional separation means to isolate the imine compound, which is then subjected to the subsequent reduction.

The reduction can be carried out by using a metal hydride complex such as sodium borohydride, sodium cyanoborohydride or lithium aluminum hydride, or by catalytic reduction employing a palladium-carbon catalyst or a Raney nickel catalyst.

When a metal hydride complex is used as a reducing agent, the reducing agent is used usually in an amount of 1 mol or an excess molar amount, preferably from 1 to 5 mols, per mol of the above imine.

For the reduction, an inert solvent, for example, an alcohol such as methanol or ethanol; an ether such as dimethyl ether, ethyl ether, diisopropyl ether, dibutyl ether, dimethoxyethane, dioxane, tetrahydrofuran or diglyme; an aliphatic hydrocarbon such as pentane, hexane, heptane or cyclohexane; or an aromatic hydrocarbon such as benzene or toluene; or a mixture of such solvents, can be used appropriately as a solvent depending upon the type of the reducing agent.

The reaction temperature is usually from 0° C. to room temperature, and the reaction time is usually from 1 hour to 6 hours.

Further, in this process, it is also possible to react an alkylating agent of the formula 5 to the nitrile or carboxylic acid derivative of the formula 1 to preliminarily produce an alkyl compound and then to react an alkyl lithium of the formula 2 or an alkyl Grignard reagent (or an alkyl Gilman reagent) of the formula 3 to the alkyl compound to obtain a compound of the formula 6. Such a reaction can be conducted under the conditions similar to the above Process A. Accordingly, the reaction conditions described for the above Process A may all be used as the reaction conditions for this reaction.

The compounds of the formulas 1, 2, 3, 5 and 7 may be commercially available or can be produced by a proper combination, as the case requires, of the methods disclosed in Reference Examples, or conventional methods or methods similar thereto.

Process B

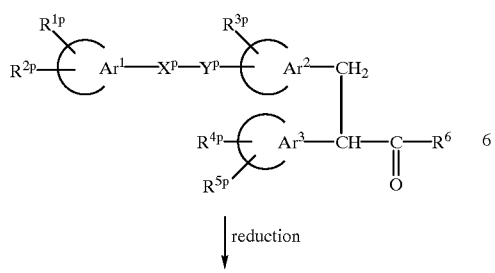

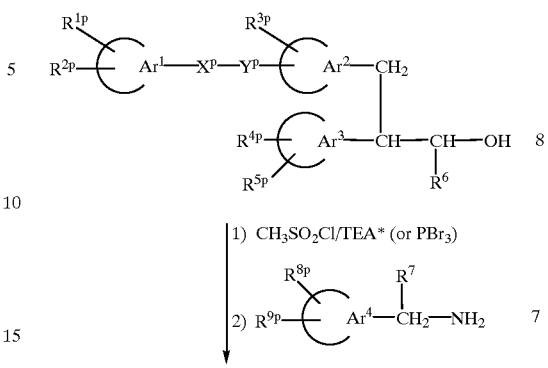

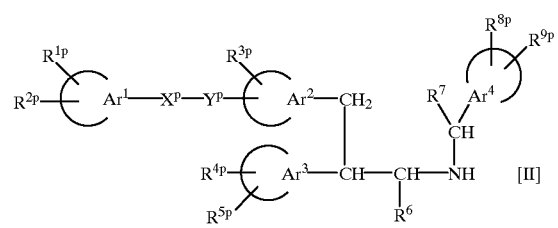

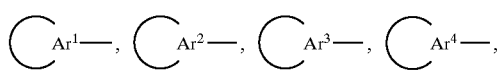

* triethylamine

In the above formulas, $X^p$, $Y^p$, $R^{1p}$, $R^{2p}$, $R^{3p}$, $R^{4p}$, $R^{5p}$, $R^6$, $R^7$, $R^{8p}$ and $R^{9p}$ are as defined above.

According to this process, the desired compound (II) can be prepared by reacting a reducing agent such as a metal hydride complex to a compound of the formula 6 to obtain an alcohol compound 8 and reacting an amine compound of the formula 7 to the alcohol compound 8.

The above reaction steps will be described in detail referring to suitable reaction conditions, etc.

The reaction for reducing the compound of the formula 6 to the alcohol compound 8 can be conducted usually by using a metal hydride complex such as sodium borohydride, diisobutyl aluminum hydride, lithium aluminum hydride or lithium tri-sec-butylborohydride (L-selectride™), or by catalytic reduction employing e.g. a palladium-carbon catalyst or a Raney nickel catalyst, in an inert solvent which does not adversely affect the reaction.

When the metal hydride complex is used as the reducing agent, such a reducing agent is used usually in an amount of 1 mol or an excess molar amount, preferably from 1 to 5 mols, per mol of the starting material compound 6.

The inert solvent to be used in this reaction may be suitably selected depending upon the type of the reducing agent.

For example, when the reducing agent is sodium borohydride, an inert solvent, such as an alcohol such as methanol or ethanol; an ether such as dimethoxyethane, dioxane, tetrahydrofuran or diglyme; an aprotic polar solvent such as dimethylformamide or dimethylacetamide, or water, or a solvent mixture thereof, may be used, and particularly preferred is an alcohol such as methanol or ethanol.

For example, when the reducing agent is diisobutyl aluminum hydride, an inert solvent, such as an ether such as dimethyl ether, ethyl ether, diisopropyl ether, dibutyl ether, dimethoxyethane, dioxane, tetrahydrofuran or diglyme; an aliphatic hydrocarbon such as pentane, hexane, heptane or cyclohexane; an aromatic hydrocarbon such as benzene or toluene; methylene chloride, or a solvent mixture thereof, may be used, and particularly preferred is toluene or methylene chloride.

For example, when the reducing agent is lithium aluminum hydride or lithium tri-sec-butylborohydride, an inert solvent, such as an ether such as dimethyl ether, ethyl ether, diisopropyl ether, dibutyl ether, dimethoxyethane, dioxane, tetrahydrofuran or diglyme; an aliphatic hydrocarbon such as pentane, hexane, heptane or cyclohexane; or an aromatic hydrocarbon such as benzene or toluene, or a solvent mixture thereof, may be used, and particularly preferred is ethyl ether or tetrahydrofuran.

For the catalytic reduction, the solvent is preferably an alcohol such as methanol or ethanol.

The reaction temperature and the reaction time vary depending upon the stability and the susceptibility to the reduction reaction of the starting material ketone compound 6, the type of the reducing agent and the type of the solvent. However, the reaction temperature is usually from −80° C. to 100° C., preferably from −70° C. to 40° C., and the reaction time is usually from 5 minutes to 2 days, preferably from 30 minutes to 24 hours.

The step of preparing the desired compound (II) from a compound of the formula 8 can be carried out by reacting a sulfonating agent such as methanesulfonyl chloride to the alcohol compound of the formula 8 in the presence of a base, or reacting a halogenating agent such as thionyl chloride or phosphorus tribromide thereto, to convert the hydroxyl group in the formula to a leaving group, followed by reacting an amine compound of the formula 7.

The reaction for introducing the leaving group can be conducted usually by reacting 1 mol or an excess molar amount, preferably from 1 to 2 mols, of a sulfonating agent and a base such as triethylamine to 1 mol of the alcohol compound 8 in an inert solvent such as methylene chloride, chloroform, benzene, tetrahydrofuran or ethyl acetate, or using 1 mol or an excess molar amount, preferably from 1 to 5 mols, of a halogenating agent.

The reaction temperature is usually from −70° C. to the boiling point of the solvent used for the reaction, preferably from −20° C. to 80° C., and the reaction time is usually from 5 minutes to 48 hours, preferably from 30 minutes to 24 hours.

Then, the step of reacting an amine compound 7 to the compound having the leaving group introduced, obtained by the above reaction, can be conducted usually by employing 1 mol or an excess molar amount, preferably from 1 to 50 mols, of the amine compound 7 per mol of the starting compound having the leaving group, in an inert solvent such as methylene chloride, chloroform, benzene, ethyl ether or tetrahydrofuran.

If necessary, this reaction can be conducted in the presence of a base other than the amine compound of the formula 7.

As such a base, an inorganic base such as sodium hydroxide, potassium hydroxide, calcium hydroxide, sodium carbonate, potassium carbonate or sodium hydrogencarbonate, or an organic base such as triethylamine, N-ethyldiisopropylamine, pyridine or N,N-dimethylaniline may, for example, be mentioned.

Such a base is used usually in an amount of 1 mol or an excess molar amount, preferably from 1 to 5 mols, per mol of the starting material compound.

The reaction temperature is usually from −50° C. to 150° C., preferably from −20° C. to 100° C., and the reaction time is usually from 5 minutes to 7 days, preferably from 10 minutes to 24 hours.

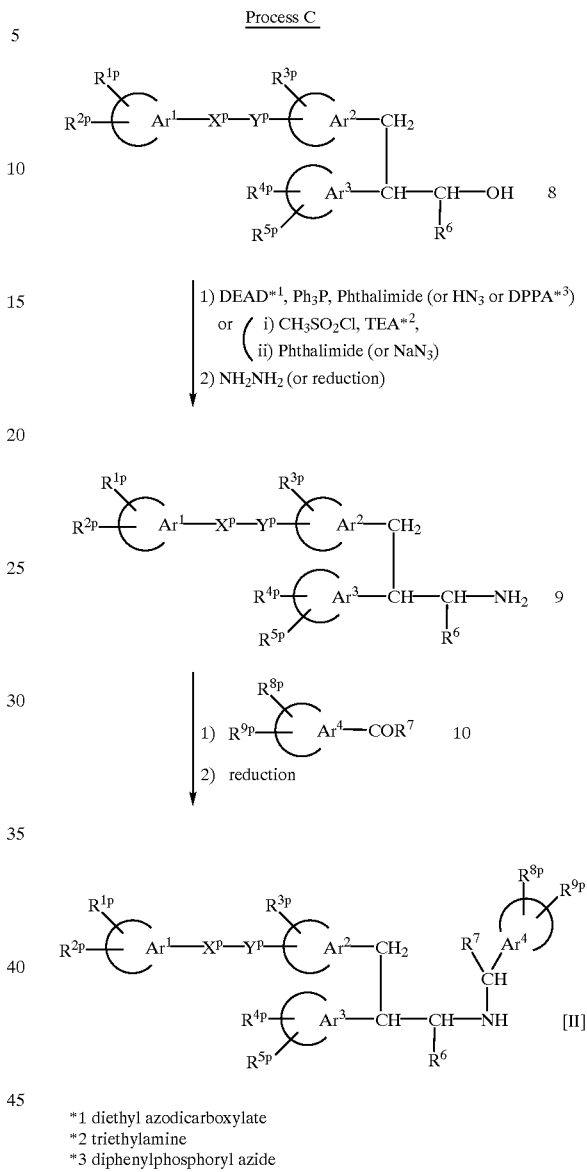

*1 diethyl azodicarboxylate
*2 triethylamine
*3 diphenylphosphoryl azide

In the above formulas,

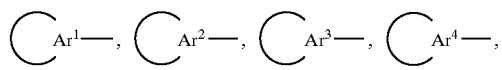

$X^p$, $Y^p$, $R^{1p}$, $R^{2p}$, $R^{3p}$, $R^{4p}$, $R^{5p}$, $R^6$, $R^7$, $R^{8p}$ and $R^{9p}$ are as defined above.

According to this process, the desired compound (II) can be prepared by firstly reacting diethyl azodicarboxylate, triphenylphosphine and phthalimide (or hydrogen azide or diphenylphosphoryl azide) or reacting a sulfonylation agent such as methanesulfonyl chloride in the presence of a base such as triethylamine, then reacting phthalimide (or sodium azide) in the presence of a base, to the alcohol compound of the formula 8, to obtain a phthalimide-protected form (or an azide compound) of the amine compound 9, then reacting hydrazine (or a reducing agent) to remove the phthalimide group (or reduce the azide group) to obtain an amine product of the formula 9, and finally reacting a compound of the formula 10 to the compound 9, followed by reduction.

The above reaction steps will be described in detail referring to suitable reaction conditions, etc.

For the step of producing the amine compound of the formula 9 from the alcohol compound 8, various synthetic methods and reaction conditions well known in organic synthetic chemistry for converting alcohol compounds to amines, may be employed. For example, it is preferred to employ a Mitsunobu reaction using diethyl azodicarboxylate, triphenylphosphine and phthalimide (or hydrogen azide or diphenylphosphoryl azide) or a method which comprises sulfonylation with a sulfonylation agent such as methanesulfonyl chloride in the presence of a base such as triethylamine, then reacting phthalimide (or sodium azide) in the presence of a base, and then treating the obtained phthalimide compound with hydrazine (or reducing the azide compound).

The above reactions are conducted usually in a solvent inert to the reaction. The inert solvent may, for example, preferably be tetrahydrofuran, dimethoxyethane, benzene or toluene in the case of the above-mentioned Mitsunobu reaction; methylene chloride, chloroform, tetrahydrofuran, benzene, ethyl acetate or dimethylformamide in the case of the sulfonylation followed by the reaction with phthalimide (or sodium azide); an alcohol such as methanol or ethanol in the next step of the phthalimide-removing reaction with hydrazine; an ether such as ethyl ether or tetrahydrofuran in the case where a metal hydride complex is used as the reducing agent in the reduction reaction of the azide compound; water-containing tetrahydrofuran in the case where phosphine reduction is conducted with triphenylphosphine or the like; and an alcohol such as methanol or ethanol in the reduction by catalytic reduction.

With respect to the amounts of the reagents to be used, in the above Mitsunobu reaction, each of diethyl azodicarboxylate, triphenylphosphine and phthalimide (or hydrogen azide or diphenylphosphoryl azide) is used in an amount of 1 mol or an excess molar amount, preferably from 1 to 5 mols, per mol of the starting material alcohol compound 8. In the reaction with the phthalimide (or sodium azide) after the sulfonylation, the sulfonylation agent such as methanesulfonyl chloride is used in an amount of 1 mol or an excess molar amount, preferably from 1 to 2 mols, per mol of the alcohol compound 8, and the base such as triethylamine used at that time is usually in an amount of 1 mol or an excess molar amount, preferably from 1 to 2 mols, per mol of the sulfonylation agent. In the next step of the reaction with phthalimide (or sodium azide) in the presence of a base, 1 mol or an excess molar amount, preferably from 1 to 5 mols of each of phthalimide and the base (or sodium azide) is used per mol of the starting material sulfonylation agent. Here, the base to be used together with phthalimide is preferably sodium carbonate or potassium carbonate. Otherwise, without using such a base, a sodium salt or a potassium salt of phthalimide may be used by itself. Then, in the reaction for removing the phthalimide group with hydrazine, hydrazine is used in an amount of 1 mol or an excess molar amount, preferably from 1 to 10 mols, per mol of the phthalimide compound as the starting material compound. In the reduction of the azide compound with a metal hydride complex or with triphenylphosphine, the reducing agent is used usually in an amount of 1 mol or an excess molar amount, preferably from 1 to 2 mols, per mol of the azide compound.

In the case of the above Mitsunobu reaction, the reaction temperature is usually from −70° C. to 100° C., preferably from −20° C. to 50° C., and the reaction time is usually from 5 minutes to 48 hours, preferably from 30 minutes to 24 hours. In the reaction for removing the phthalimide group by hydrazine, the reaction temperature is usually from 0° C. to the boiling point of the solvent used for the reaction, preferably from room temperature to 100° C., and the reaction time is usually from 5 minutes to 48 hours, preferably from 30 minutes to 24 hours. In the reaction for converting the azide compound to the amine compound by reduction, when a metal hydride complex is used as the reducing agent, the reaction temperature is usually from −70° C. to 150° C., preferably from −20° C. to 50° C., and the reaction time is usually from 5 minutes to 48 hours, preferably from 10 minutes to 10 hours. When triphenylphosphine is used as the reducing agent, the reaction temperature is usually from room temperature to the boiling point of the solvent used for the reaction, preferably from 30° C. to 100° C., and the reaction time is usually from 10 minutes to 48 hours, preferably from 30 minutes to 24 hours. Further, in the case of the reduction by catalytic reduction, the reaction temperature is usually from 0° C. to 100° C., preferably from room temperature to 50° C., and the reaction time is usually from 10 minutes to 48 hours, preferably from 10 minutes to 24 hours.

The step for producing the desired compound (II) from the compound of the formula 9 is carried out usually by preliminarily forming an imine by reacting 1 mol or an excess molar amount, preferably from 1 to 2 mols of the compound of the formula 10 to 1 mol of the compound of the formula 9 in an inert solvent such as methanol, ethanol, benzene, ethyl ether or tetrahydrofuran, and then reducing it.

This step can be carried out in the same manner as the step for producing the desired compound (II) from the compound of the formula 6 in the above process A. Accordingly, with respect to the reaction conditions, etc., similar conditions may be employed.

Further, the compound of the formula 10 may be commercially available or can be produced by a proper combination, as the case requires, of the methods disclosed in Reference Examples, or conventional methods or methods similar thereto.

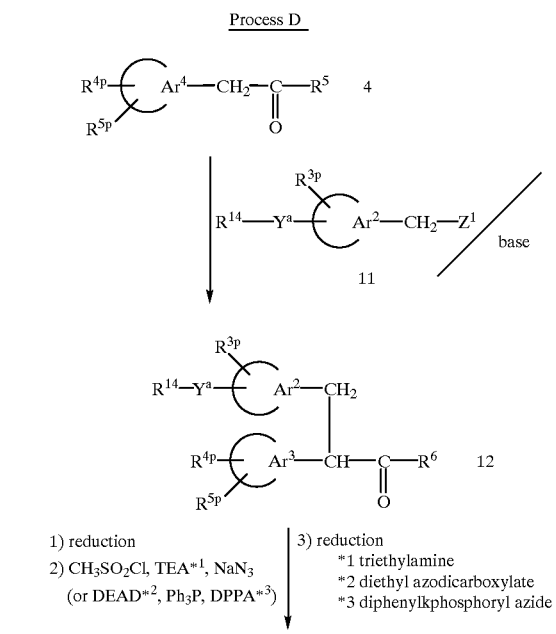

-continued

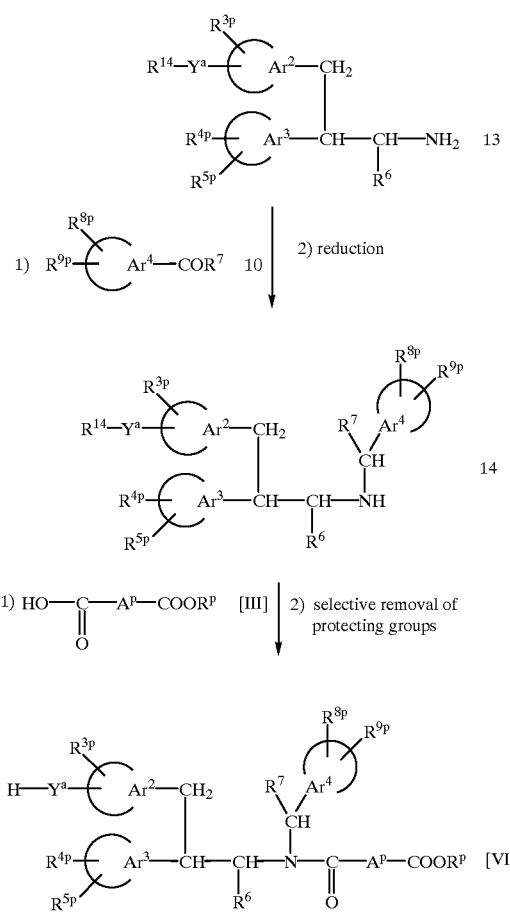

In the above formulas, $R^{14}$ means a hydroxyl-protecting group when $Y^a$ is an oxygen atom; a mercapto-protecting group when $Y^a$ is a sulfur atom; or an amino- or imino-protecting group when $Y^a$ is a group of the formula $-NR^b-$ (wherein $R^b$ is as defined above); and

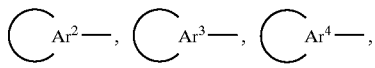

$A^p$, $Y^a$, $Z^1$, $R^{3p}$, $R^{4p}$, $R^{5p}$, $R^6$, $R^7$, $R^{8p}$, $R^{9p}$ and $R^p$ are as defined above.

According to this process, the desired compound (VI) can be prepared by firstly reacting an alkylating agent of the formula 11 to a ketone compound of the formula 4 to obtain a compound of the formula 12, reacting a reducing agent such as a metal hydride complex to the compound 12 to obtain an alcohol compound, then reacting diethyl azodicarboxylate, triphenylphosphine and phthalimide (or hydrogen azide or diphenylphosphoryl azide) or reacting a sulfonylation agent such as methanesulfonyl chloride in the presence of a base such as triethylamine, and then reacting phthalimide (or sodium azide) in the presence of a base, to obtain a phthalimide-protected form (or an azide compound) of the amine compound 13, then reacting hydrazine (or a reducing agent) to remove the phthalimide group (or reduce the azide group) to obtain an amine compound of the formula 13, reacting a compound of the formula 10 to the compound 13, followed by reduction to obtain a compound of the formula 14, reacting a carboxylic acid of the formula (III) or its reactive derivative to the compound 14, and finally selectively removing the protecting group represented by $R^{14}$.

The step of producing a compound of the formula 12 from a ketone compound of the formula 4, can be carried out in the same manner as the step of producing the compound of the formula 6 from the ketone of the formula 4 in the above process A. Accordingly, with respect to the reaction conditions, etc., similar conditions may be employed.

When $R^{14}$ is a hydroxyl-protecting group, such a hydroxyl-protecting group may be the one disclosed above with respect to process 1.

When $R^{14}$ is a mercapto-protecting group, the hydroxyl-protecting group disclosed above with respect to process 1 can be used as such a mercapto-protecting group.

When $R^{14}$ is an amino- or imino-protecting group, such an amino- or imino-protecting group may be the amino- or imino-protecting group disclosed above with respect to process 1.

In the step of producing the amine compound of the formula 13 after reacting a reducing agent such as a metal hydride complex to the compound of the formula 12 to obtain an alcohol compound, the step of converting the compound of the formula 12 to the alcohol compound can be carried out in the same manner as the step of reducing the compound of the formula 6 to the alcohol compound 8 in the above process B. Accordingly, with respect to the reaction conditions, etc., similar conditions may be employed. Further, the step of producing an amine compound of the formula 13 from the obtained alcohol, can be carried out in the same manner as in the step of producing the amine compound 9 from the alcohol compound of the formula 8 in the above process C. Accordingly, with respect to the reaction conditions, etc., similar conditions may be employed.

The step of producing a compound of the formula 14 from the amine compound of the formula 13, can be carried out in the same manner as in the step of producing a compound of the formula (II) from the amine of the formula 9 in the above process C. Accordingly, with respect to the reaction conditions, etc., similar conditions may be employed.

In the step of producing the desired compound (VI) from the compound of the formula 14, the reaction of the compound of the formula 14 with the carboxylic acid of the formula (III) or its reactive derivative, can be carried out in the same manner as the reaction of the compound of the formula (II) with the carboxylic acid of the formula (III) or its reactive derivative in the above process 1. Accordingly, with respect to the reaction conditions, etc., similar conditions may be employed.

For the step of selectively removing the protective group represented by $R^{14}$ from the compound obtained by the above reaction, various methods may suitably be selected depending upon the type and the characteristics of the protecting group. Namely, utilizing the difference in the stability against an acid, a base or reduction between $R^{14}$ and other protecting groups, the protecting group can selectively be removed by a conventional means such as an acid, a base or reduction. With respect to specific conditions for such a reaction, the methods disclosed in known literatures, such as "Protective Groups in Organic Synthesis, T. W. Greene, John Siley & Sons (1981)", may, for example, be used.

Further, the compound of the formula 11 may be commercially available, or may be produced by a proper combination, as the case requires, of the methods disclosed in Reference Examples, or conventional methods or methods similar thereto.

Process E

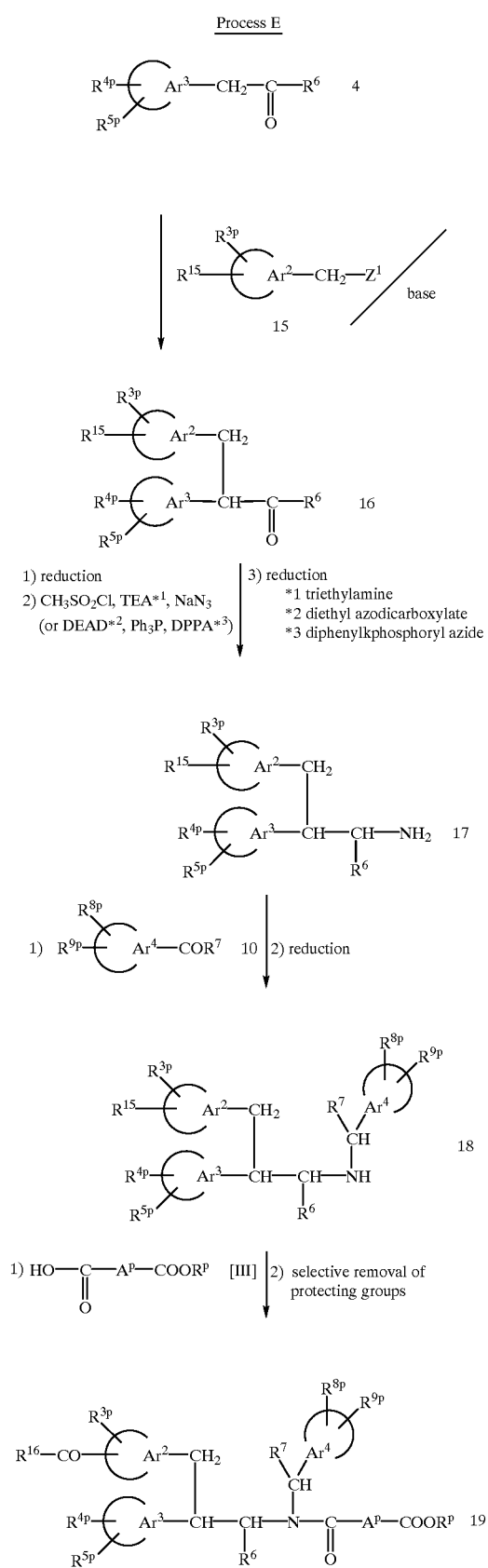

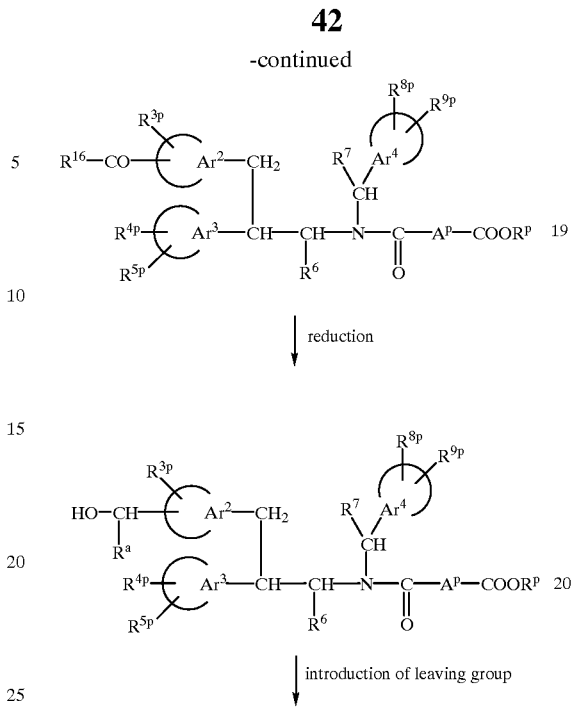

In the above formulas, $R^{15}$ is a protected carboxyl group or a group of the formula $R^a$—$C(OR^{p1})(OR^{p2})$— (wherein each of $R^{p1}$ and $R^{p2}$ which are the same or different, is a methyl group or an ethyl group, or $R^{p1}$ and $R^{p2}$ together represent an ethylene group, and $R^a$ is as defined above); $R^{16}$ is a hydroxyl group or a group of the formula $R^a$ (wherein $R^a$ is as defined above); and

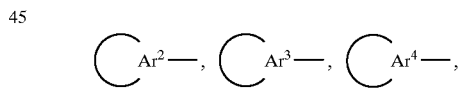

$A^p$, $Z$, $Z^1$, $R^{3p}$, $R^{4p}$, $R^{5p}$, $R^6$, $R^7$, $R^{8p}$, $R^{9p}$, $R^a$ and $R^p$ are as defined above.

According to this process, the desired compound (VIII-a) can be prepared by firstly reacting an alkylating agent of the formula 15 to a ketone compound of the formula 4 to obtain a compound of the formula 16, reacting a reducing agent such as a metal hydride complex to the compound 16 to obtain an alcohol compound, then reacting diethyl azodicarboxylate, triphenylphosphine and phthalimide (or hydrogen azide or diphenylphosphoryl azide), or reacting a sulfonylation agent such as methanesulfonyl chloride in the presence of a base such as triethylamine and then reacting phthalimide (or sodium azide) in the presence of a base, to obtain a phthalimide-protected form (or an azide compound) of the amine compound 17, then reacting hydrazine (or a reducing agent) to remove the phthalimide group (or reduce the azide group) to obtain an amine compound of the formula 17, reacting a compound of the formula 10 to the compound 17, followed by reduction to obtain a compound of the formula 18, reacting a carboxylic acid of the formula (III) or its reactive derivative to the compound 18, then selectively removing the protecting group at $R^{15}$ to obtain a compound of the formula 19, reacting a reducing agent to the compound 19 to obtain a compound of the formula 20, and finally introducing a leaving group to the compound 20.

The respective steps up to the production of the compound of the formula 19 from the ketone compound of the formula 4 can be carried out in the same manner as the respective steps for the production of the compound of the formula (VI) from the ketone compound of the formula 4 in the above process D. Accordingly, with respect to the reaction conditions, etc., the same conditions as in the corresponding respective steps can be employed.

The step of reacting a reducing agent to the compound of the formula 19 to obtain the compound of the formula 20, can be conducted in the same manner as the reduction method employing e.g. sodium borohydride as a reducing agent in the step of reducing the compound of the formula 6 to an alcohol compound 8 in the above process B. Accordingly, with respect to the reaction conditions, etc., similar conditions can be employed.

The step of producing the desired compound (VIII-a) by introducing a leaving group to the compound of the formula 20 can be carried out in the same manner as in the method of introducing a leaving group to the compound of the formula 8 in the above process B by using, for example, a halogenating agent such as thionyl chloride, phosphorus trichloride, phosphorus pentachloride, phosphorus oxychloride, phosphorus tribromide, oxalyl chloride or phosgene, or a sulfonating agent such as methanesulfonyl chloride, p-toluenesulfonyl chloride or benzenesulfonyl chloride. Accordingly, with respect to the reaction conditions, etc., similar conditions may be employed.

Further, the compound of the formula 15 may be commercially available, or can be produced by a proper combination, as the case requires, of the methods disclosed in Reference Examples, or conventional methods or methods similar thereto.

Process F

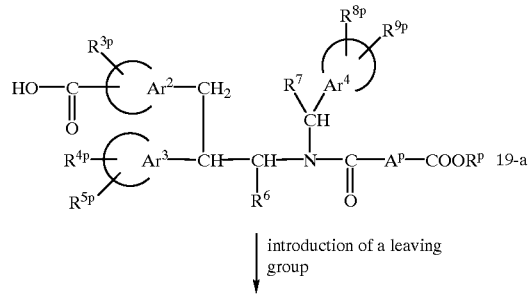

introduction of a leaving group

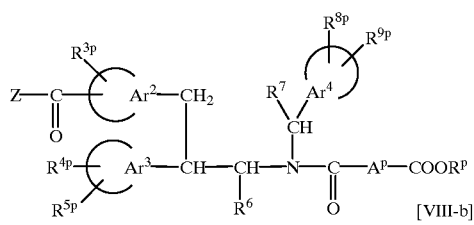

In the above formulas,

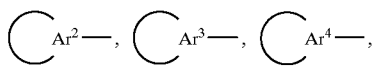

$A^p$, Z, $R^{3p}$, $R^{4p}$, $R^{5p}$, $R^6$, $R^7$, $R^{8p}$, $R^{9p}$ and $R^p$ are as defined above.

According to this process, the desired compound (VIII-b) can be prepared by introducing a leaving group to the compound of the formula 19-a in the same manner and conditions as the method of introducing a leaving group to the compound of the formula 20 in the above process E.

Process G

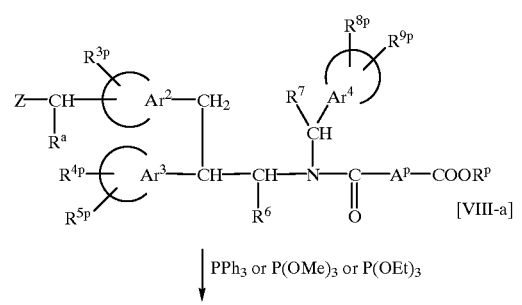

PPh₃ or P(OMe)₃ or P(OEt)₃

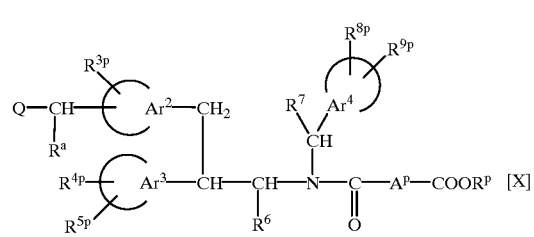

In the above formulas,

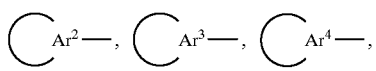

$A^p$, Q, Z, $R^{3p}$, $R^{4p}$, $R^{5p}$, $R^6$, $R^7$, $R^{8p}$, $R^{9p}$, $R^a$ and $R^p$ are as defined above.

According to this process, the desired compound (X) can be prepared by reacting triphenylphosphine, trimethyl phosphite or triethyl phosphite, to the compound of the formula (VIII-a).

When a triphenylphosphine is reacted, the above reaction is carried out usually in an inert solvent which does not affect the reaction. As such an inert solvent, toluene or xylene is, for example, preferred.

The triphenylphosphine is used usually in an amount of 1 mol or an excess molar amount, preferably from 1 to 5 mols, per mol of the compound (VIII-a).

The reaction temperature is usually from room temperature to the boiling point of the solvent used for the reaction, preferably from 80° C. to 150° C. The reaction time is usually from 5 minutes to 7 days, preferably from 1 hour to 24 hours.

Likewise, when trimethyl phosphite or triethyl phosphite is reacted to the compound (VIII-a), the above reaction is conducted usually in an inert solvent which does not affect the reaction, or more preferably, an excess trimethyl phosphite or triethyl phosphite is used as both the solvent and the reactant.

The reaction temperature is usually from room temperature to the boiling point of the solvent for the reaction, preferably from 80° C. to 150° C., and the reaction time is usually from 5 minutes to 7 days, preferably from 1 hour to 24 hours.

A compound of the formula (XII):

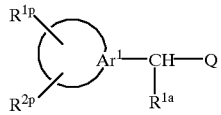
(XII)

wherein

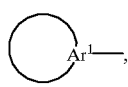

Q, $R^{1p}$, $R^{2p}$ and $R^{1a}$ are as defined above, can be prepared from a compound of the formula (XIV):

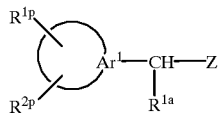
(XIV)

wherein

Z, $R^{1p}$, $R^{2p}$ and $R^{1a}$ are as defined above, in accordance with process G.

Further, the compound of the formula (XIV) may be commercially available, or can be prepared by a proper combination, as the case requires, of the methods disclosed in Reference Examples, or conventional methods or methods similar thereto.

Further, the formula (XIII):

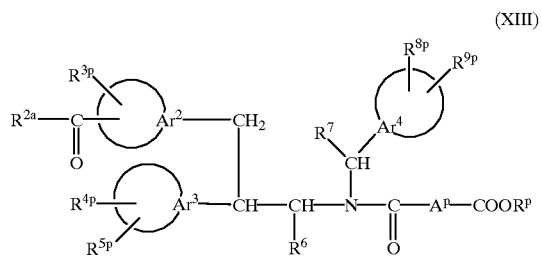
(XIII)

wherein

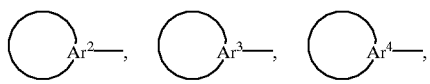

$A^p$, $R^{3p}$, $R^{4p}$, $R^{5p}$, $R^6$, $R^7$, $R^{8p}$, $R^{9p}$, $R^p$ and $R^{2a}$ are as defined above, is substantially the same as the formula 19 in the above process E, wherein $R^{16}$ is a group of the formula $R^a$.

Accordingly, the compound of the formula (XIII) can be prepared by the above process E.

Process H

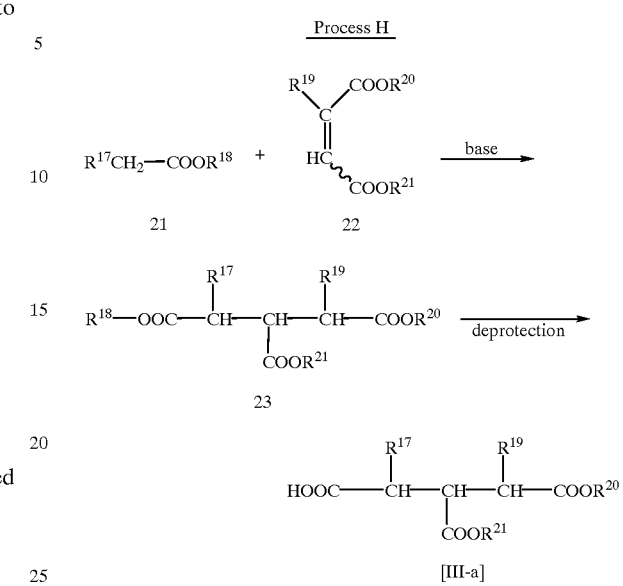

[III-a]

In the above formulas, each of $R^{17}$ and $R^{19}$ which are the same or different, is a hydrogen atom, a lower alkyl group, an aryl group or an aralkyl group; each of $R^{20}$ and $R^{21}$ which are the same or different, is a carboxyl-protecting group; and $R^{18}$ is a tert-butyl group, a benzyl group, a benzhydryl group or a trityl group.

Process H is a process for preparing a carboxylic acid derivative of the formula (III-a) among the compounds of the above formula (III).

According to this process, the desired carboxylic acid derivative (III-a) can be prepared by conducting a so-called Michael addition reaction which comprises reacting a maleic acid derivative or a fumaric acid derivative of the formula 22 to an ester derivative having a readily removable carboxyl-protecting group $R^{18}$, represented by the formula 21, in the presence of a base, and then removing the carboxyl-protecting group $R^{18}$ from the obtained Michael addition product 23 under a mild condition.

As the carboxyl-protecting group for $R^{20}$ and $R^{21}$, a lower alkyl group such as a tert-butyl group, or a benzhydryl group, is preferred.

The protecting group $R^{18}$ is preferably the one which can readily be removed under a mild condition of catalytic reduction or weakly acidic condition and which is stable under the Michael addition reaction condition, such as a tert-butyl group, a benzyl group, a benzhydryl group or a trityl group.

The above Michael addition reaction can be conducted by reacting the compound of the formula 22 in an amount of 1 mol or an excess molar amount, preferably from 1 to 2 mols, to 1 mol of the compound of the formula 21 in the presence of a base such as sodium hydride, butyl lithium, lithium diisopropylamide or lithium bis(trimethylsilyl)amide usually in an inert solvent such as benzene, ethyl ether or tetrahydrofuran.

Such a base is used usually in an amount of 1 mol or a slightly excess molar amount, preferably from 1 to 1.5 mols, per mol of the compound of the formula 22.

The reaction temperature is usually from −100° C. to 100° C., preferably from −80° C. to room temperature, and the reaction time is usually from 5 minutes to 24 hours, preferably from 10 minutes to 10 hours.

The reaction conditions for the reaction for removing the protecting group from the compound of the formula 23 to form the desired carboxylic acid derivative (III-a), vary depending upon the type of the protecting group, etc. For example, when the protecting group is a tert-butyl group, a benzhydryl group or a trityl group, a method may be employed wherein the compound is treated with an acid such as acetic acid, formic acid, trifluoroacetic acid or hydrochloric acid, preferably within a temperature range of from −20° C. to 50° C. for from 10 minutes to 24 hours in the absence of a solvent or usually in an inert solvent such as methylene chloride, anisole, tetrahydrofuran, methanol or ethanol or a solvent mixture thereof with water.

For example, when the protecting group is a benzyl group, a benzhydryl group or a trityl group, a method may be employed wherein the compound is catalytically reduced with a catalyst such as a palladium-carbon catalyst or a Raney nickel catalyst preferably under a hydrogen pressure of from 1 to 20 kg/cm² preferably within a temperature range of from 0° C. to 40° C. for from 10 minutes to 24 hours usually in an inert solvent such as methanol, ethanol, dioxane, water or acetic acid, or a solvent mixture thereof.

Among compounds of the formula (III-a), an optically active compound of the formula (III-b¹):

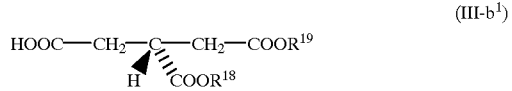

(III-b¹)

or the formula (III-b²):

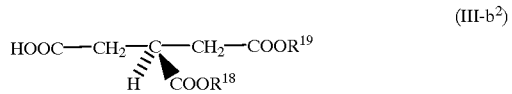

(III-b²)

wherein each of $R^{18}$ and $R^{19}$ which are the same or different, is a carboxyl-protecting group, can be obtained by reacting a racemic mixture of the compound of the formula (III-b):

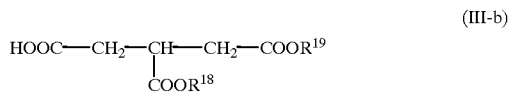

(III-b)

wherein $R^{18}$ and $R^{19}$ are as defined above, with cinchonidine or quinine to obtain a mixture of two diastereomers, then separating and collecting either one of the diastereomers by utilizing the difference in the solubility as between the two diastereomers, followed by recovering the free carboxylic acid by treating with an acid.

Separation of the diastereomer mixture may be conducted in an organic solvent such as carbon tetrachloride or iso-propyl ether. Usually, the mixture of the diastereomers is dissolved in a solvent in a hot state, and the solution is gradually cooled to utilize the solubility difference for separation of the diastereomers.

Further, either one of the diastereomers thus obtained is treated with an acid such as hydrochloric acid to obtain an optically active compound of the formula (III-b¹) or (III-b²).

The compounds of the formula 21 and 22 may be commercially available or can be produced by a proper combination, as the case requires, of the methods disclosed in Reference Examples, or conventional methods or methods similar thereto.

Process I

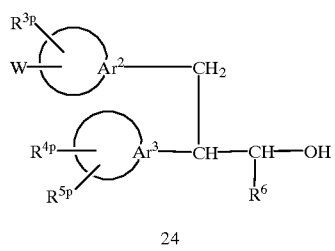

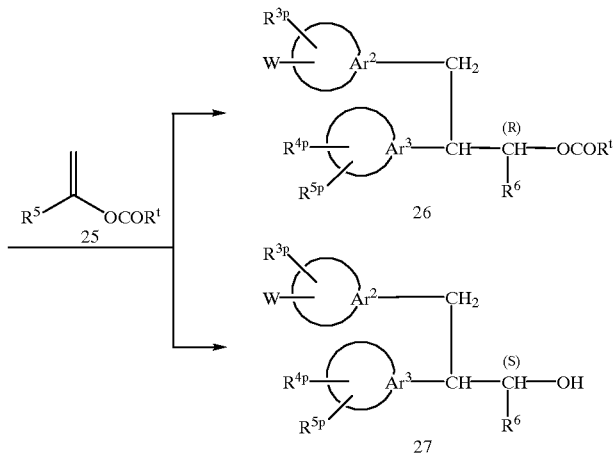

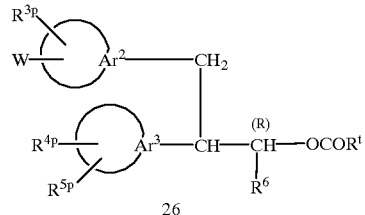

hydrolysis

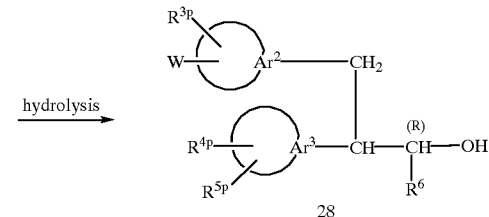

In the above formulas, W is

(wherein

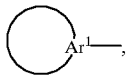

$X^p$, $Y^p$, $R^{1p}$ and $R^{2p}$ are as defined above), $R^{14}$—$Y^a$— (wherein $Y^a$ and $R^{14}$ are as defined above) or $R^{15}$ (wherein $R^{15}$ is as defined above); $R^s$ is a hydrogen atom or a methyl group; $R^t$ is a lower alkyl group, an aryl group or a lower alkenyl group; and

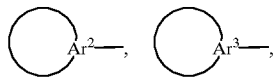

$R^{3p}$, $R^{4p}$, $R^{5p}$ and $R^6$ are as defined above.

Process I is a process for preparing an optically active substance 27 or 28 of an alcohol compound 24 obtainable as the above formula 8 or a reduction product of the formula 12 or 16.

According to this process, the desired optically active alcohol compounds 27 and 28 can be prepared by reacting a vinyl ester derivative of the formula 25 to a racemic alcohol derivative of the formula 24 in the presence of a lipase, separating the obtained optically active ester derivative 26 and the optically active alcohol derivative, and then hydrolyzing the ester group with respect to the optically active ester derivative 26.

$R^t$ of the vinyl ester derivative of the formula 25 is preferably a lower alkyl group such as a methyl group or an ethyl group; an aryl group such as a phenyl group or a naphthyl group; or an aralkyl group such as a benzyl group or a 2-phenylethyl group. Particularly preferred is a methyl group, i.e. a case wherein the compound of the formula 25 is vinyl acetate or isopropenyl acetate.

The above optical resolution reaction by lipase can be conducted usually in an inert solvent such as methylene chloride, chloroform, ethyl ether, tetrahydrofuran, benzene, toluene, hexane, heptane or acetonitrile, or by using the starting material vinyl ester derivative of the formula 25 itself as the solvent.

The vinyl ester derivative 25 is used usually in an amount of 1 mol or in a large excess molar amount, preferably from 1 to 100 mols, per mol of the starting material compound 24, and the amount of the lipase as the catalyst is from 0.01 to 100%, preferably from 0.1 to 20%, by weight, relative to the compound 24.

The type of the lipase is preferably a lipase derivative from Pseudomonas sp. such as Toyothium LIP™ (manufactured by Toyobo).

Further, the above enzymatic reaction tends to be accelerated, when the reaction is carried out in the presence of a base. As a base to be used for this purpose, an organic base such as triethylamine or diisopropylethylamine, is preferred.

The base is used usually in an amount of 0.01 mol or a slightly excess molar amount, preferably from 0.1 to 1.5 mols, relative to the starting material compound 24.

The reaction temperature is usually from 0° C. to 50° C., preferably from room temperature to 40° C. The reaction time is usually from 30 minutes to 7 days, preferably from 1 hour to 48 hours.

The hydrolytic reaction of the ester of the formula 26 can be conducted by a common method well known in the organic synthetic chemistry under an acidic or basic condition.

To demonstrate the usefulness of the compounds of the present invention, 50% inhibitory concentrations ($IC_{50}$ values) of the compounds of the present invention against the protein-farnesyl transferase (PFT) activities, were obtained.

Inhibitory Activities Against Protein-Farnesyl Transferase (1) Preparation of PFT PFT was separated in such a manner that a soluble fraction of rat's brain was fractionated by means of 30%–50% saturated ammonium sulfate, further dialyzed and then subjected to column chromatography by Q-cephalose™ (manufactured by Pharmacia) (Reiss et al, Cell, vol. 62, p. 81–88 (1990)).

(2) Method for measuring PFT activities

Measurement of PFT activities was conducted by using, as a prenyl acceptor, H-ras protein or a substance that biotin was added to N-terminal of a peptide corresponding to a 7 amino acid residue at C terminal of K-rasB protein (biotin-added Lys-Thr-Ser-Cys-Val-Ile-Met) and, as a prenyl doner, [$^3$H]-labeled farnesylpyrophosphate (FPP) (Reiss et al, Methods: A Companion to a Methods in Enzymology, vol. 1, No. 3, p. 241–245 (1990)).

The [$^3$H]-labeled farnesylpyrophosphate (22.5 Ci/mmol) was purchased from New England Nuclear Co. Non-labeled farnesylpyrophosphate was chemically synthesized from ditriethylammonium phosphate, trans-trans-farnesol and trichloroacetonitrile and purified by XAD-2-resin column and diethylaminoethylcellulose (Cornforth et al, Methods in Enzymology, vol. 15, p. 385–390 (1969)).

H-ras protein was expressed in *Escherichia coli* and purified (Gibbs et al, Proc. Natl. Acad. Sci., vol. 81, p. 5704–5708 (1984)).

The PFT reaction solution containing H-ras protein as the prenyl acceptor was 25 μl, and its composition was 50 mM Hepes pH7.5/50 μM $ZnCl_2$/5 mM $MgCl_2$/20 mM KCl/5mM DTT/0.6 μM all trans [$^3$H]-farnesylpyrophosphate/25 μM H-ras protein/PFT derived from rat brain (Q-sephalose fraction). The reaction temperature was 37° C., the preincubation time was 10 minutes, and the reaction time was 20 minutes.

The PFT reaction solution containing biotin-added Lys-Thr-Ser-Cys-Val-Ile-Met as the prenyl acceptor, was 25 μl, and its composition was 50 mM tris-Cl pH7.5/50 μM $ZnCl_2$/5 mM $MgCl_2$/20 mM KCl/1 mM DTT/0.2% n-octyl-β-D-glucopyranoside/0.6 μM all trans [$^3$H]-farnesylpyrophosphate/3.6 μM biotin-added Lys-Thr-Ser-Cys-Val-Ile-Met/PFT derived from rat brain (Q-sephalose fraction). The reaction temperature was 37° C., the preincubation time was 10 minutes, and the reaction time was 20 minutes.

The enzymatic reaction product containing H-ras protein as the prenyl acceptor, was analyzed by SDS-PAGE (sodium dodecylsulfate/polyacrylamide gel electrophoresis). The [$^3$H]-labeled enzymatic reaction product was boiled for 3 minutes in a buffer solution containing 2% SDS/50 mM Tris-Cl pH6.8/10% sucrose/5% 2-mercaptoethanol, then subjected to electrophoresis with a slab gel of 12% polyacrylamide, whereby the [$^3$H]-labeled H-ras protein was fluorography-enhanced by EN$^3$HANCE™ (manufactured by New England Nuclear Co.) and then visualized by autoradiography (James et al, Science, vol. 260, No. 25, p. 1937–1942 (1993)).

The measurement of PFT activities using H-ras protein as the prenyl receptor, was also analyzed by a rapid separate method. The mixed solution for measurement wherein no prenyl doner was present, was preincubated and a prenyl group transferring reaction was initiated by an addition of [$^3$H]-FPP and terminated at an appropriate time by an addition of 0.5 ml of 4% SDS. Further, 0.5 ml of 30% trichloroacetic acid was added thereto and thoroughly mixed. Then, the reaction solution was left to stand at 4° C. for 60 minutes to let H-ras protein precipitate. This reaction solution was subjected to filtration under reduced pressure by Whatman GF/B filter. The filter was washed 6 times with 2 ml of 6% trichloroacetic acid, and mixed with 8 ml of scintillation cocktail (Clearsol I™, manufactured by Nacalai Tesque Co.). Then, counting was carried out by a Beckmann TRI-CARB2500TR scintillation counter.

Measurement of PFT activities was also carried out by using biotin-added Lys-Thr-Ser-Cys-Val-Ile-Met as the prenyl acceptor. The mixed solution for measurement containing biotin-added Lys-Thr-Ser-Cys-Val-Ile-Met as the prenyl acceptor and containing no prenyl doner, was preliminarily thermally equilibrated, and then a prenyl group transferring reaction was initiated by an addition of [$^3$H]-FPP and terminated at an appropriate time by an addition of 0.2 ml of 2 mg/ml bovine serum albumin/2% sodium dodecylsulfate/ 150 mM NaCl. Further, 0.02 ml of avidin agarose (Pierce) was added thereto, and the mixture was shaked for 30 minutes to let the [$^3$H]-farnesyl group-transferred biotin-added Lys-Thr-Ser-Cys-Val-Ile-Met sufficiently bond to the avidin agarose. Then, avidin agarose was washed four times with 1 ml of 2 mg/ml bovin serum albumin (BSA)/4% sodium dodecylsulfate/150 mM NaCl, and mixed with 1 ml of scintillation cocktail (Clearsol I™, manufactured by Nacalai Tesque). Then, counting was carried out by a Beckmann TRI-CARB2500TR scintillation counter.

The biotin-added Lys-Thr-Ser-Cys-Val-Ile-Met heptapeptide used as an artificial substrate, was synthesized in a solid phase by an Applied biosystems model 431A peptide synthesizer, and an α-amino terminal of the solid phase Lys-Thr-Ser-Cys-Val-Ile-Met heptapeptide which was bound to a resin, was biotin-modified by N-hydroxysuccinimide biotin, then cut off from the resin and purified by reversed phase high performance liquid chromatography (HPLC).

The addition of the compound of the present invention to the PFT reaction system was carried out by preliminarily adding dimethyl sulfoxide in an amount of 1% by volume (0.25 μl) of the reaction solution.

The 50% inhibitory concentrations (IC$_{50}$ values) of the compounds of the present invention against PFT activities, were obtained, and the results are shown in the following Table.

TABLE 1

| 50% inhibitory concentrations against PFT activities | |
|---|---|
| Compound | IC$_{50}$ (nM) |
| Example 1 | 0.6 |
| Example 10 | 1.8 |

PHARMACOLOGICAL TEST EXAMPLE 2 (Inhibitory Activities Against Farnesyl-Modification of Ras Protein)

Using the compounds of the present invention, inhibitory activities against farnesyl-modification of Ras protein in NIH3T3 cells transformed by activated ras gene, were measured.

The NIH3T3 cells transformed by activated ras gene, were seeded on a culture plate and cultured for 3 days. Then, a compound of the preset invention in a predetermined concentration was added to the culture. In accordance with the method disclosed in J. Biol. Chem., vol. 268, p. 18415 (1993), the cells were cultured for 24 hours and then taken off from the plate, and the cells were dissolved. After centrifugal separation for 5 minutes under 12000 g, the supernatant was used as a cell extract. The cell extract was subjected to SDS polyacrylamide gel electrophoresis to separate farnesyl-modified Ras protein and non-farnesyl-modified Ras protein. The protein on the gel was transferred onto a nitrocellulose membrane, and an anti-Ras protein antibody was reacted as a probe (primary antibody reaction). An anti-primary antibody, a peroxidase inclusion (secondary antibody), was reacted, and then Ras protein was detected by a chemical fluorescence enhancing kit. The proportion of non-farnesyl-modified Ras protein was quantified by a densitometer and taken as the inhibitory activity.

The 50% inhibitory concentrations (IC$_{50}$ values) of the compounds of the present invention against farnesyl-modification of Ras protein are shown in Table 2.

TABLE 2

| 50% inhibitory concentrations against farnesyl-modification of Ras protein | |
|---|---|
| Compound | IC$_{50}$ (nM) |
| Example 25 | 21 |
| Example 29 | 4.7 |
| Example 30 | 21 |

From the forgoing results, the compounds of the present invention have excellent inhibitory activities against protein-farnesyl transferase (PFT) and thus useful as anti-tumor agents, for example, against colon cancers, pancreatic cancers, myloid leukemias, lung cancer, carcinoma cutaneum or thyroid gland cancer, particularly against pancreatic cancers.

The compound of the formula (I) of the present invention can be orally or parenterally administered, and it may be formulated into a formulation suitable for such administration, so that it can be used as an antitumor agent. To use the compound of the present invention for clinical purpose, it may be formulated into various formulations by an addition of pharmaceutically acceptable additives to meet the type of administration and then administered. As such additives, various additives which are commonly used in the field of drug formulations, may be used, including, for example, gelatin, lactose, saccharose, titanium oxide, starch, crystalline cellulose, hydroxypropylmethylcellulose, carboxymethylcellulose, corn starch, microcrystalline wax, white petrolatum, magnesium metasilicate aluminate, anhydrous calcium phosphate, citric acid, trisodium citrate, hydroxypropylcellulose, sorbitol, sorbitan fatty acid ester, polysorbate, sucrose fatty acid ester, polyoxyethylene hardened castor oil, polyvinylpyrrolidone, magnesium stearate, light silicic anhydride, talc, vegetable oil, benzyl alcohol, gum arabic, propylene glycol, polyalkylene glycol, cyclodextrin and hydroxypropylcyclodextrin, etc.

A drug formulation to be prepared as a mixture with such additives, may, for example, be a solid formulation such as a tablet, a capsule, a granule, a powder or a suppository; or a liquid formulation such as a syrup, an elixir or an injection drug. These formulations can be prepared in accordance with conventional methods commonly employed in the field of drug formulations. Further, in the case of a liquid formulation, it may be of the type which is to be dissolved or suspended in water or in other suitable medium at the time of its use. Particularly, in the case of an injection drug, it may be dissolved or suspended in a physiological saline or in a glucose solution, and a buffering agent or a preserving agent may further be added.

These formulations may contain the compound of the present invention in a proportion of from 1.0 to 100 wt %, preferably from 1.0 to 60 wt % of the total amount.

These formulations may further contain therapeutically effective other compounds.

When the compound of the present invention is used as an antitumor agent, its dose and the frequency of administration vary depending upon the sex, the age, the body weight and the diseased degree of the patient and the type and the range of the intended treating effects. However, in the case of an oral administration, it is preferred to administer from 0.01 to 20 mg/kg per day for an adult all at once or in a few times in a divided fashion. In the case of parenteral administration, it is preferred to administer from 0.002 to 10 mg/kg per day for an adult all at once or in a few times in a divided fashion.

EXAMPLES and REFERENCE EXAMPLES

Now, the present invention will be described in further detail with reference Examples and Reference Examples. However, the present invention is by no means restricted by such Examples.

Example 1

Preparation of N-[(1RS,2RS)-1-methyl-2-(4-nitrophenyl)-3-{5-(phenylcarbamoyl)-2-furyl}propyl]-N-(2-naphthylmethyl)carbamoylmethylsuccinic acid (1) Preparation of di-tert-butyl N-{(1RS,2RS)-3-(5-ethoxycarbonyl-2-furyl)-1-methyl-2-(4-nitrophenyl)propyl)-N-(2-naphthylmethyl)carbamoylmethylsuccinate 1.15 g of ethyl 5-{(2RS,3RS)-3-(2-naphthylmethylamino)-2-(4-nitrophenyl)butyl)-2-furancarboxylate obtained in Reference Example 1, 0.30 9 of 4-dimethylaminopyridine and 0.91 g of 1,2-di-tert-butyl 1,2,3-propanetricarboxylate obtained in Reference Example 2 were dissolved in 10 ml of methylene chloride, and 0.93 g of 1-ethyl-3-(3-dimethylaminopropyl)carbodiimide hydrochloride was added thereto under cooling with ice with stirring, followed by stirring at room temperature for 18 hours. The reaction solution was diluted with ethyl acetate, and then, the organic layer was sequentially washed with 1N hydrochloric acid, a saturated sodium hydrogencarbonate aqueous solution and a saturated sodium chloride aqueous solution and dried over anhydrous magnesium sulfate. The drying agent was filtered off, and then, the solvent was distilled off under reduced pressure. The residue was purified by silica gel column chromatography (hexane/ethyl acetate=7/1+5/1) to obtain 1.44 g (yield: 80%) of the above-identified compound as a slightly yellow oily substance.

(2) Preparation of di-tert-butyl N-{(1RS,2RS)-3-(5-carboxy-2-furyl)-1-methyl-2-(4-nitrophenyl)propyl}-N-(2-naphthylmethyl)carbamoylmethylsuccinate 1.44 g of di-tert-butyl N-[(1RS,2RS)-3-(5-ethoxycarbonyl-2-furyl)-1-methyl-2-(4-nitrophenyl)propyl]-N-(2-naphthylmethyl)carbamoylmethylsuccinate was dissolved in a mixed solution of 15 ml of methanol and 7 ml of tetrahydrofuran, and 6 ml of a 1N sodium hydroxide aqueous solution was added thereto, followed by stirring at 40° C. for 2 hours. The reaction solution was acidified by an addition of 2N hydrochloric acid and then extracted with ethyl acetate. The organic layer was washed with a saturated sodium chloride aqueous solution and then dried over anhydrous magnesium sulfate. The drying agent was filtered off, and then, the solvent was distilled off under reduced pressure. The residue was purified by silica gel column chromatography (methylene chloride/methanol=100/1+50/1) to obtain 1.11 g (yield: 80%) of the above-identified compound as a slightly yellow oily substance.

(3) Preparation of N-[(1RS,2RS)-1-methyl-2-(4-nitrophenyl)-3-{5-(phenylcarbamoyl)-2-furyl}propyl]-N-(2-naphthylmethyl)carbamoylmethylsuccinic acid 50 mg of di-tert-butyl N-{(1RS,2RS)-3-(5-carboxy-2-furyl)-1-methyl-2-(4-nitrophenyl)propyl}-N-(2-naphthylmethyl)carbamoylmethylsuccinate was dissolved in 10 ml of methylene chloride, and 11 mg of 4-dimethylaminopyridine, 8 mg of aniline and 17 mg of 1-ethyl-3-(3-dimethylaminopropyl)carbodiimide hydrochloride were added thereto, followed by stirring at room temperature for 18 hours. The reaction solution was diluted with ethyl acetate, and then, sequentially washed with 1N hydrochloric acid, a saturated sodium hydrogencarbonate aqueous solution and a saturated sodium chloride aqueous solution and dried over anhydrous magnesium sulfate. The drying agent was filtered off, and then, the solvent was distilled off under reduced pressure. The residue was purified by silica gel column chromatography (hexane/ethyl acetate=5/1+3/1) to obtain 55 mg (yield: quantitative) of the di-tert-butyl ester of the above-identified compound.

The ester thus obtained was dissolved in 2 ml of formic acid, followed by stirring at room temperature for 3 hours. Then, the reaction solution was evaporated to dryness under reduced pressure. Toluene was added to the residue, and the mixture was again evaporated to dryness under reduced pressure. The obtained residue was treated with methylene chloride/hexane to obtain 36 mg (yield; 76%) of the above-identified compound as a white crystalline powder.

$^1$H-NMR(CDCl$_3$+CD$_3$OD)δ:0.94–1.02(3H, m), 2.50–3.50(8H, m), 4.40–4.70(1H, m), 4.75–4.95(2H, m), 5.54 and 5.76(total 1H, each d, each J=3.4Hz), 6.81 and 6.95(total 1H, each d, each J=3.4Hz), 7.15(1H, t, J=7.2Hz), 7.30–7.60, 7.70–7.90 and 8.10–8.21(total 15H, each m)

FAB-MS;678(M+H)

Compounds of Examples 2 to 14 were prepared in the same manner as in Example 1 except that instead of ethyl 5-{(2RS,3RS)-3-(2-naphthylmethylamino)-2-(4-nitrophenyl)butyl)-2-furancarboxylate and/or aniline used as the starting material in the above reaction, the corresponding ester derivatives and/or amine compounds were employed.

Example 2

N-[(1RS,2RS)-3-(5-(3,4-dimethoxyphenylcarbamoyl)-2-furyl}-1-methyl-2-(4-nitrophenyl)propyl]-N-(2-naphthylmethyl)carbamoylmethylsuccinic acid $^1$H-NMR(CDCl$_3$+CD$_3$OD)δ:0.95–1.02(3H, m), 2.60–3.60(8H, m), 3.87–3.92(6H, m), 4.50–5.00(3H, m), 5.56–5.60 and 5.74–5.79(total 1H, each m), 6.80–7.00, 7.11–7.18 and 7.30–8.20(total 15H, each m)

FAB-MS:738(M+H)

Example 3

N-[(1RS,2RS)-3-{5-(2-hydroxyphenylcarbamoyl)-2-furyl}-1-methyl-2-(4-nitrophenyl)propyl]-N-(2-naphthylmethyl)carbamoylmethylsuccinic acid $^1$H-NMR(CD$_3$COCD$_3$)δ:0.80–1.10(3H, m), 2.60–4.00 (8H, m), 4.60–5.10(3H, m), 5.72, 5.78 and 6.05(total 1H, each d, each J=3.2Hz), 6.80–7.10, 7.35–7.65, 7.70–8.20 (total 16H, each m)8.70–8.80 and 9.05–9.15(total 1H, each m)

FAB-MS:694(M+H)

Example 4

N-[(1RS,2RS)-1-methyl-3-{5-(N-methylphenylcarbamoyl)-2-furyl)-2-(4-nitrophenyl)propyl]-N-(2-naphthylmethyl)carbamoylmethylsuccinic acid $^1$H-NMR(CD$_3$COCD$_3$)δ:0.80–1.00(3H, m), 2.50–3.70 (8H, m), 3.52 and 3.55(total 3H, each s), 4.30–5.10(3H, m), 5.50–5.55, 5.60–5.65 and 5.75–5.80(total 1H, each m), 7.10–7.30, 7.40–7.60, 7.75–8.00 and 8.10–8.20(total 17H, each m)

FAB-MS:692(M+H)

Example 5

N-[(1RS,2RS)-1-methyl-2-(4-nitrophenyl)-3-{5-(3-pyridylcarbamoyl)-2-furyl}propyl)-N- (2-naphthylmethyl)carbamoylmethylsuccinic acid hydrochloride $^1$H-NMR(CD$_3$OD)δ:0.97–1.02(3H, m), 2.50–3.85(8H, m), 4.15–5.05(3H, m), 5.79, 5.88 and 5.95(total 1H, each d, each J=3.5Hz), 6.99, 7.04 and 7.11(total 1H, each d, each J=3.5Hz), 7.30–8.20(12H, m), 8.50–8.70, 8.80–8.90 and 9.40–9.55(total 3H, each m)

FAB-MS:716(M+H)

Example 6

N-[(1RS,2RS)-1-methyl-2-(4-nitrophenyl)-3-{5-(4-pyridylcarbamoyl)-2-furyl}propyl]-N-(2-naphthylmethyl)carbamoylmethylsuccinic acid hydrochloride $^1$H-NMR(CD$_3$OD)δ:0.96–1.03(3H, m), 2.50–3.75(8H, m), 4.20–5.05(3H, m), 5.77, 5.86 and 5.98(total 1H, each d, each J=3.5Hz), 7.05, 7.12 and 7.20(total 1H, each d, each J=3.5Hz), 7.30–7.90, 8.08–8.18 and 8.45–8.64(total 15H, each m)

FAB-MS:716(M+H)

Example 7

N-[(1RS,2RS)-1-methyl-2-(4-nitrophenyl)-3-{5-(5-pyrimidinylcarbamoyl)-2-furyl}propyl]-N-(2-naphthylmethyl)carbamoylmethylsuccinic acid hydrochloride $^1$H-NMR(CD$_3$OD)δ:0.97–1.03(3H, m), 2.55–3.75(8H, m), 4.50–5.00(3H, m), 6.08(1H, d, J=3.8Hz), 7.10–7.60, 7.75–7.90 and 8.10–8.20(total 12H, each m), 8.58–8.65, 8.80–8.90 and 9.18–9.22(total 3H, each m)

FAB-MS:717(M+H)

Example 8

N-[(1RS,2RS)-1-methyl-2-(4-nitrophenyl)-3-(5-(2-thiazolylcarbamoyl)-2-furyl}propyl]-N-(2-naphthylmethyl)carbamoylmethylsuccinic acid hydrochloride $^1$H-NMR(CD$_3$OD)δ:0.97–1.03(3H, m), 2.50–3.90(8H, m), 4.50–5.00(3H, m), 5.80–6.10(1H, m), 7.07–8.16(14H, m)

FAB-MS:722(M+H)

Example 9

N-[(1RS,2RS)-2-(4-chlorophenyl)-1-methyl-3-(5-(phenylcarbamoyl)-2-furyl)propyl]-N-(2-naphthylmethyl)carbamoylmethylsuccinic acid $^1$H-NMR(CDCl$_3$)δ:0.87 and 0.89(total 3H, each d, each J=6.8Hz), 2.17–3.58(9H, m), 4.45–4.80(2H, m), 5.79(1H, d, J=3.3Hz), 6.94(1H, d, J=3.3Hz), 7.00–7.12, 7.28–7.39, 7.45–7.54 and 7.59–7.84(total 16H, each m)

FAB-MS:667(M+H)

Example 10

N-[(1RS,2RS)-2-(4-chlorophenyl)-1-methyl-3-(3-phenylcarbamoylphenyl)propyl}-N-(2-naphthylmethyl)carbamoylmethylsuccinic acid $^1$H-NMR(CDCl$_3$)δ:0.80–1.05(3H, m), 2.30–3.50(8H, m), 4.20–5.40(3H, m), 6.70–8.40(21H, m)

FAB-MS:677(M+H)

Example 11

N-[(1RS,2RS)-2-(4-chlorophenyl)-1-methyl-3-{3-(phenylcarbamoyl)-5-isoxazolyl)propyl]-N-(2-naphthylmethyl)carbamoylmethylsuccinic acid $^1$H-NMR(CD$_3$OD)δ:0.83–1.01(3H, m), 2.42–3.43(8H, m), 3.52–3.64(1H, m), 4.49–4.98(2H, m), 6.17 and 6.19 (total 1H, each s), 7.11–7.35, 7.44–7.64 and 7.74–7.89(total 14H, each m)

FAB-MS:668(M+H)

Example 12

N-[(1RS,2RS)-2-(4-chlorophenyl)-1-methyl-3-(4-(phenylcarbamoyl)-2-pyridyl)propyl]-N-(2-naphthylmethyl)carbamoylmethylsuccinic acid $^1$H-NMR(CD$_3$OD)δ:0.88–0.97(3H, m), 2.53–2.88(4H, m), 3.02–3.44(3H, m), 3.54–3.79(1H, m), 4.49–4.53(1H, m), 4.72–5.03(2H, m), 7.11–7.27, 7.34–7.55 and 7.65–7.89 (total 18H, each m), 8.45–8.50(1H, m)

FAB-MS:678(M+H)

Example 13

(2R*)-2-N-(2-benzo[b]thienylmethyl)-N-[(1RS,2RS)-1-methyl-2-(3,4-methylenedioxyphenyl)-3-{5-(phenylcarbamoyl)-2-furyl}propyl]carbamoylmethyl]succinic acid $^1$H-NMR(CD$_3$OD)δ:1.04–1.11(3H, m), 2.55–3.45(8H, m), 4.24–4.37 and 4.71–5.06(total 3H, each m), 5.67 and 5.69(total 1H, each d, each J=3.2Hz), 5.86–5.90(3H, m), 6.64–6.96(4H, m), 7.10–7.37 and 7.59–7.81(total 10H, each m)

FAB-MS:683(M+H)

Example 14

(2R*)-2-[N-(2-benzo[b]thienylmethyl)-N-[(1RS,2RS)-1-methyl-2-(3,4-methylenedioxyphenyl)-3-(5-(3-pyridylcarbamoyl)-2-furyl}propyl)carbamoylmethyl]succinic acid hydrochloride $^1$H-NMR(CD$_3$OD)δ:1.04–1.13(3H, m), 2.50–3.75(8H, m), 4.70–5.10(3H, m), 5.86 and 5.90(total 2H, each s), 5.90–

6.00(1H, m), 6.56–6.92(3H, m), 7.04–7.40, 7.57–7.82 and 8.00–8.08(total 7H, each m), 8.54–8.57, 8.67–8.70, 8.85–8.92, 9.44–9.45 and 9.53–9.57(total 3H, each m)

Example 15

Preparation of monopivaloyloxymethyl (2R*)-2-[N-(2-benzo[b]thienylmethyl)-N-[(1RS,2RS)-1-methyl-2-(3,4-methylenedioxyphenyl)-3-{5-(phenylcarbamoyl)-2-furyl}propyl]carbamoylmethyl]succinate 38 mg of (2R*)-2-[N-(2-benzo[b]thienylmethyl)-N-[(1RS,2RS)-1-methyl-2-(3,4-methylenedioxyphenyl)-3-[5-(phenylcarbamoyl)-2-furyl)propylcarbamoylmethyl]succinic acid (compound of Example 13) was dissolved in 2 ml of dimethylformamide, and 23 μl of triethylamine and 16 μl of pivaloyloxymethyl chloride were added thereto, followed by stirring at 40° C. for 7 hours. The reaction solution was poured into 0.1N hydrochloric acid and extracted with ethyl ether. Then, the organic layer was washed with a saturated sodium chloride aqueous solution and dried over anhydrous magnesium sulfate. The drying agent was filtered off, and then, the solvent was distilled off under reduced pressure. The residue was purified by silica gel column chromatography (hexane/ethyl acetate=1/3) to obtain 19 mg (yield: 43%) of the above-identified compound $^1$H-NMR(CDCl$_3$)δ:1.05–1.13(3H, m), 2.49–3.33(8H, m), 3.97–4.94(3H, m), 5.50–5.94(5H, m), 6.54–6.85(1H, m), 6.98–7.00(4H, m), 7.09–7.40(1H, m), 7.53–7.81(10H, m)

FAB-MS:797(M+H)

Compounds of Examples 16 and 17 were prepared in the same manner as in Example 1 except that instead of ethyl 5-{(2RS,3RS)-3-(2-naphthylmethylamino)-2-(4-nitrophenyl)butyl}-2-furancarboxylate used as the starting material in Example 1, the corresponding amine derivatives were employed.

Example 16

(2R*)-2-[N-{(1RS,2RS)-2-(4-methoxycarbonylphenyl)-1-methyl-3-(3-phenoxymethylphenyl)propyl}-N-(2-naphthylmethyl)carbamoylmethyl]succinic acid $^1$H-NMR(CDCl$_3$)δ:0.85–1.00(3H, m), 2.48–3.55(8H, m), 3.87(3H, s), 4.22–4.80(3H, m), 4.83–4.88(2H, m), 5.10–5.50(1H, br), 6.22–6.35, 6.72–7.20, 7.20–7.31 and 7.35–7.90(total 19H, each m)

FAB-MS:688(M+H)

Example 17

(2R*)-2-[N-[(1RS,2RS)-2-(4-methoxycarbonylphenyl)-1-methyl-3-{3-(phenoxymethyl)-5-(1,2,4-oxadiazolyl)}-propyl]-N-(2-naphthylmethyl)carbamoylmethyl]succinic acid $^1$H-NMR(CD$_3$COCD$_3$)δ:0.92–1.01(3H, m), 2.61–3.80 (9H, m), 3.85(3H, s), 4.60–5.10(2H, m), 5.20–5.35(2H, m), 7.28–7.60(7H, m), 7.77–7.96(6H, m)

FAB-MS:680(M+H)

Example 18

(2R*)-2-[N-[(1RS,2RS)-2-(4-methoxycarbonylphenyl)-1-methyl-3-{(E)-3-styrylphenyl}propyl]-N-(2-naphthylmethyl)carbamoylmethyl]succinic acid $^1$H-NMR(CDCl$_3$)δ:0.82–0.95(3H, m), 2.40–3.80(9H, m), 3.86–3.88(3H, m), 4.20–4.90(2H, m), 6.15–6.98(6H, m), 7.02–7.67(11H, m), 7.72–7.95(5H, m)

FAB-MS:684(M+H)

Example 19

(2R*)-2-[N-[(1RS,2RS)-2-(4-methoxycarbonylphenyl)-1-methyl-3-(3-(2-phenylethyl)phenyl]propyl]-N-(2-naphthylmethyl)carbamoylmethyl]succinic acid 183 mg of di-tert-butyl (2R* )-2-[N-[(1RS,2RS)-2-(4-methoxycarbonylphenyl)-1-methyl-3-{(E)-3-styrylphenyl)propyl]-N-(2-naphthylmethyl)carbamoylmethyl]succinate as a diester of the compound of Example 18, was dissolved in 5 ml of methanol, and 20 mg of a 10% palladium-carbon catalyst was added thereto, followed by catalytic reduction at room temperature under atmospheric pressure with hydrogen overnight. The reaction solution was filtered through a cerite filter, and the filtrate was concentrated under reduced pressure. Then, the residue was purified by silica gel column chromatography (hexane/ethyl acetate=1/1) to obtain 125 mg (yield: 68%) of a di-tert-butyl ester of the above-identified compound.

120 mg of the ester thus obtained was dissolved in 4 ml of trifluoroacetic acid, followed by stirring at room temperature for one hour. Then, trifluoroacetic acid was distilled off under reduced pressure. The residue was purified by medium pressure liquid chromatography (Lobor column™, size A, RP-8 (manufactured by Merck Co.); acetonitrile/0.1% trifluoroacetic acid aqueous solution=2/1) to obtain 89 mg (yield: 87%) of the above-identified compound as a colorless foam.

$^1$H-NMR(CDCl$_3$)δ:0.82–1.00(3H, m), 2.50–3.18(12H, m), 3.33–3.57(1H, m), 3.84(3H, s), 4.25–4.90(2H, m), 6.08–6.97, 7.02–7.50 and 7.58–7.92(total 20H, each m)

FAB-MS:686(M+H)

Example 20

N-{(1RS,2RS)-2-(4-chlorophenyl)-1-methyl-3-(4-phenylethynylphenyl)propyl}-N-(2-naphthylmethyl)carbamoylmethylsuccinic acid 22 mg of N-{(1RS,2RS)-2-(4-chlorophenyl)-1-methyl-3-(4-phenylethynylphenyl)propyl)-2-naphthylmethylamine obtained in Reference Example 3 was dissolved in 1 ml of methylene chloride, and 12 mg of chloroformylmethylsuccinic anhydride and 12 μl of diisopropylethylamine were added thereto, followed by stirring at room temperature for 45 minutes. The reaction solution was evaporated to dryness under reduced pressure. Then, the residue was dissolved in a mixed solution of 1 ml of tetrahydrofuran and 0.5 ml of water, and 40 mg of lithium hydroxide monohydrate was added thereto, followed by stirring at room temperature for 15 minutes. The reaction solution was diluted with ethyl ether, then acidified by an addition of 1N hydrochloric acid, washed with a saturated sodium chloride aqueous solution and then dried over anhydrous magnesium sulfate. The drying agent was filtered off, and then, the solvent was distilled off under reduced pressure. The residue was purified by silica gel column thin layer chromatography (Kieselgel™60F$_{254}$, Art™5744; chloroform/methanol=7/1) to obtain 15 mg (yield: 53%) of the above-identified compound as a colorless oily substance.

$^1$H-NMR(CDCl$_3$+CD$_3$OD)δ:0.80–1.05(3H, m), 2.45–3.50(8H, m), 4.25–4.40, 5.10–5.45(total 1H, m), 4.45–4.83(2H, m), 6.18–7.90(20H, m)

FAB-MS:658(M+H)

Compounds of Examples 21 to 22 were prepared in the same manner as in Example 20 except that instead of N-{(1RS,2RS)-2-(4-chlorophenyl)-1-methyl-3-(4-phenylethynylphenyl)propyl)-2-naphthylmethylamine used as the starting material in the above reaction, the corresponding amine derivatives were employed.

Example 21

N-[(1RS,2RS)-2-(4-chlorophenyl)-1-methyl-3-{(E)-3-styrylphenyl)propyl]-N-(2-naphthylmethyl) carbamoylmethylsuccinic acid $^1$H-NMR(CDCl$_3$+CD$_3$OD)δ:0.86–1.00(3H, m), 2.48–3.45(8H, m), 4.30–4.95(3H, m), 6.31–7.90(22H, m)

FAB-MS:660(M+H)

Example 22

N-[(1RS,2RS)-2-(4-methoxycarbonylphenyl)-1-methyl-3-(5-phenoxymethyl-2-furyl)propyl}-N-(2-naphthylmethyl)carbamoylmethylsuccinic acid $^1$H-NMR(CD$_3$COCD$_3$)δ:0.85–1.01(3H, m), 2.50–3.70 (9H, m), 3.85(3H, s), 4.50–5.02(4H, m), 5.45–5.55 and 5.70–5.75(total 1H, each m), 6.05–6.10 and 6.18–6.22(total 1H, each m), 6.90–7.01(3H, m), 7.10–7.60(7H, m), 7.78–7.95(6H, m)

FAB-MS:678(M+H)

Example 23

Preparation of 4-[N-[(1RS,2RS)-1-methyl-2-(4-nitrophenyl)-3-{5-(phenylcarbamoyl)-2-furyl}propyl]-N-(2-naphthylmethyl)carbamoyl]-1,2,3-butanetricarboxylic acid (1) Preparation of N-[(1RS,2RS)-1-methyl-2-(4-nitrophenyl)-3-(5-(phenylcarbamoyl)-2-furyl) propyl]-2-naphthylmethylamine 1.15 g of ethyl 5-{(2RS,3RS)-3-(2-naphthylmethylamino)-2-(4-nitrophenyl)butyl)-2-furancarboxylate obtained in Reference Example 1, was dissolved in 10 ml of ethanol, and 4 ml of a 1N sodium hydroxide aqueous solution was added thereto, followed by stirring at 40° C. for 2.5 hours. The solvent was distilled off under reduced pressure, and the residue was acidified by an addition of 1N hydrochloric acid and then extracted by an addition of ethyl acetate. The organic layer was washed with a saturated sodium chloride aqueous solution and then dried over anhydrous magnesium sulfate. The drying agent was filtered off, and then, the solvent was distilled off under reduced pressure. The residue was dissolved in 5 ml of dimethylformamide. Then, 453 mg of aniline was added thereto, and then 587 mg of 1-ethyl-3-(3-dimethylaminopropyl)carbodiimide hydrochloride was added thereto, followed by stirring at room temperature overnight. The reaction solution was diluted with ethyl acetate, sequentially washed with 1N hydrochloric acid, water, a 1N sodium hydroxide aqueous solution and a saturated sodium chloride aqueous solution and dried over anhydrous magnesium sulfate. Then, the drying agent was filtered off. The solvent was distilled off under reduced pressure. Then, the residue was purified by silica gel column chromatography (hexane/ethyl acetate=3/1+1/1) to obtain 973 mg (yield: 77%) of the above-identified compound as a slightly yellow foam.

(2) Preparation of 4-[N-[(1RS,2RS)-1-methyl-2-(4-nitrophenyl)-3-(5-(phenylcarbamoyl)-2-furyl}propyl]-N-(2-naphthylmethyl)carbamoyl]-1,2,3-butanetricarboxylic acid 21 mg of 2,3,4-triethyl 1,2,3,4-butanetetracarboxylate (the one obtained by dissolving a commercially available tetraethyl ester of meso-butane-1,2,3,4-tetracarboxylic acid in ethanol and partially hydrolyzing the ester by an addition of 1 equivalent, based on the ester, of a 1N sodium hydroxide aqueous solution) was dissolved in 2 ml of chloroform, and 5 μl of thionyl chloride was added thereto, followed by heating and refluxing for one hour. The reaction solution was cooled to 0° C., and then 0.5 ml of a chloroform solution containing 35 mg of N-[(1RS,2RS)-1-methyl-2-(4-nitrophenyl)-3-(5-(phenylcarbamoyl)-2-furyl}propyl)-2-naphthylmethylamine, was added thereto, followed by stirring at room temperature for 2 hours. A saturated sodium hydrogencarbonate aqueous solution was added to the reaction solution, and the mixture was extracted with ethyl acetate. Then, the organic layer was washed with a saturated sodium chloride aqueous solution and dried over anhydrous magnesium sulfate. The drying agent was filtered off, and then, the solvent was distilled off under reduced pressure. The residue was purified by silica gel thin layer chromatography (Kieselgel™60F$_{2541}$ Art™5744; hexane/ethyl acetate=1/1) to obtain 24 mg (yield: 43%) of a triethyl ester of the above-identified compound.

The ester thus obtained was dissolved in a mixed solution of 2 ml of tetrahydrofuran and 2 ml of ethanol, and 1 ml of a 3N sodium hydroxide aqueous solution was added thereto, followed by stirring at room temperature for 18 hours. The mixture was acidified by an addition of 1N hydrochloric acid and then extracted with ethyl acetate. The organic layer was washed with a saturated sodium chloride aqueous solution and then dried over anhydrous magnesium sulfate. The drying agent was filtered off, and then, the solvent was distilled off under reduced pressure. The residue was purified by medium pressure liquid chromatography (Lobor column™, size A, RP-8 (manufactured by Merck Co.); acetonitrile/0.1% trifluoroacetic acid aqueous solution=1/1) to obtain 15 mg (yield: 70%) of the above-identified compound as a white powder.

$^1$H-NMR(CD$_3$COCD$_3$)δ:0.80–1.10(3H, m), 2.30–3.90 (9H, m), 4.60–5.20(3H, m), 5.70–6.70(1H, m), 6.80–7.00 (1H, m), 7.10–8.30(16H, m), 8.80–9.00 and 9.20–9.40(total 1H, m)

FAB-MS:736(M+H)

Example 24

Preparation of disodium (3RS,4RS)-3-carboxylato-4-hydroxy-4-[N-[(1RS,2RS)-1-methyl-2-(4-nitrophenyl)-3-(5-(phenylcarbamoyl)-2-furyl}propyl]-N-(2-naphthylmethyl)carbamoyl] butanoate and disodium (3SR,4SR)-3-carboxylato-4-hydroxy-4-[N-[(1RS,2RS)-1-methyl-2-(4-nitrophenyl)-3-(5-(phenylcarbamoyl)-2-furyl}propyl]-N-(2-naphthylmethyl)carbamoyl] butanoate (1) Preparation of tert-butyl (2RS,3RS)-2-[N-[(1RS,2RS)-1-methyl-2-(4-nitrophenyl)-3-(5-(phenylcarbamoyl)-2-furyl)propyl]-N-(2-naphthylmethyl)carbamoyl]-5-oxotetrahydrofuran-3-carboxylate and tert-butyl (2SR,3SR)-2-[N-[(1RS,2RS)-1-methyl-2-(4-nitrophenyl)-3-{5-(phenylcarbamoyl)-2-furyl}propyl]-N-(2-naphthylmethyl)carbamoyl]-5-oxotetrahydrofuran-3-carboxylate 87 mg of N-[(1RS,2RS)-1-methyl-2-(4-nitrophenyl)-3-{5-(phenylcarbamoyl)-2-furyl)propyl]-2-naphthylmethylamine obtained in Example 23(1), 54 mg of (2RS,3RS)-3-tert-butoxycarbonyl-5-oxotetrahydrofuran-2- carboxylic acid prepared by the method of Reference Example 4 and 97 μl of triethylamine were dissolved in 3 ml of chloroform, and 1 ml of a chloroform solution containing 59 mg of 2-chloro-1,3-dimethylimidazolium chloride under cooling with ice, followed by stirring at the same temperature for 30 minutes. The reaction solution was poured into water and extracted with chloroform. The extract solution was dried over anhydrous magnesium sulfate. The drying agent was filtered off, and then, the solvent was distilled off under reduced pressure. The residue was purified by silica gel column chromatography (hexane/ethyl acetate=2/1), whereby the above-identified compounds which are in the relation of diastereomers, were obtained as colorless oily substances in amounts of 39 mg (the component eluting first in the silica gel column chromatography: yield: 32%) and 49 mg (the component eluting later in the silica gel column chromatography: yield: 40%), respectively.

(2) Preparation of (2RS,3RS)-2-[N-[(1RS,2RS)-1-methyl-2-(4-nitrophenyl)-3-{5-(phenylcarbamoyl)-2-furyl}propyl]-N-(2-naphthylmethyl)carbamoyl]-5-oxotetrahydrofuran-3-carboxylic acid and (2SR,3SR)-2-[N-[(1RS,2RS)-1-methyl-2-(4-nitrophenyl)-3-(5-(phenylcarbamoyl)-2-furyl)propyl]-N-( 2-naphthylmethyl)carbamoyl]-5-oxotetrahydrofuran-3-carboxylic acid 28 mg of tert-butyl (2RS,3RS)-2-[N-[(1RS,2RS)-1-methyl-2-(4-nitrophenyl)-3-{5-(phenylcarbamoyl)-2-furyl) propyl]-N-(2-naphthylmethyl)carbamoyl]-5-oxotetrahydrofuran-3-carboxylate was dissolved in 1 ml of formic acid, and the solution was left to stand at room temperature overnight. The reaction solution was distilled off under reduced pressure. Then, toluene was added to the residue, followed by redistillation to obtain 26 mg (yield: 99%) of the above-identified compound as a white foam.

$^1$H-NMR(CDCl$_3$)δ:0.80–1.05(3H, m), 2.40–3.70(6H, m), 4.00–4.20, 4.40–4.60 and 4.80–5.30(total 4H, each m), 5.50–5.85(1H, m), 6.70–7.00(1H, m), 7.05–7.85 and 8.10–8.50(total 17H, m)

FAB-MS:676(M+H)

A similar reaction was carried out to obtain a compound which is in a relation of a diastereomer.

(2SR,3SR)-2-[N-[(1RS,2RS)-1-methyl-2-(4-nitrophenyl)-3-{5-(phenylcarbamoyl)-2-furyl) propyl]-N-(2-naphthylmethyl)carbamoyl]-5-oxotetrahydrofuran-3-carboxylic acid $^1$H-NMR(CDCl$_3$)δ:0.95 and 1.05(total 3H, each d, J=6.7Hz), 2.70–4.90(7H, m), 5.00–5.80(4H, m), 6.75–6.95 (1H, m), 7.05–8.30 and 8.50–8.80(total 17H, m)

FAB-MS:676 (M+H)

(3) Preparation of disodium (3RS,4RS)-3-carboxylato-4-hydroxy-4-[N-[(1RS,2RS)-1-methyl-2-(4-nitrophenyl)-3-{5-(phenylcarbamoyl)-2-furyl}propyl]-N-(2-naphthylmethyl)carbamoyl] butanoate and disodium (3SR,4SR)-3-carboxylato-4-hydroxy-4-[N-[(1RS,2RS)-1-methyl-2-(4-nitrophenyl)-3-{5-(phenylcarbamoyl)-2-furyl}propyl]-N-(2-naphthylmethyl)carbamoyl] butanoate 26 mg of (3RS,4RS)-5-[N-[(1RS,2RS)-1-methyl-2-(4-nitrophenyl)-3-{5-(phenylcarbamoyl)-2-furyl)propyl]-N-(2-naphthylmethyl)carbamoyl]-2-oxotetrahydrofuran-4-carboxylic acid was dissolved in 5 ml of methanol, and 76 μl of a 1N sodium hydroxide aqueous solution was added thereto, followed by stirring at room temperature for 30 minutes. The reaction solution was evaporated to dryness under reduced pressure to obtain 28 mg (yield: quantitative) of the above-identified compound as a white solid.

$^1$H-NMR(CD$_3$OD)δ:0.80–1.05(3H, m), 2.40–3.70(6H, m), 4.70–5.20(4H, m), 5.60–5.80(1H, m), 6.70–6.85(1H, m), 7.15–8.20(16H, m)

FAB-MS:716(M+Na)

A similar reaction was carried out to obtain a compound which is in a relation of a diastereomer.

Disodium (3SR,4SR)-3-carboxylato-4-hydroxy-4-[N-[(1RS,2RS)-1-methyl-2-(4-nitrophenyl)-3-(5-(phenylcarbamoyl)-2-furyl)propyl]-N-(2-naphthylmethyl) carbamoyl]butanoate $^1$H-NMR(CD$_3$OD)δ:0.80–1.10(3H, m), 2.55–3.70(6H, m), 4.60–4.95 and 5.15–5.50(4H, each m), 5.62 and 5.71 (total 1H, each d, each J=3.1Hz), 7.05–7.15 and 7.30–8.20 (total 16H, each m)

FAB-MS:716(M+Na)

Example 25

Preparation of 3-tert-butoxycarbonyl-4-hydroxy-4-[N-[(1RS,2RS)-1-methyl-2-(4-nitrophenyl)-3-(5-(phenylcarbamoyl)-2-furyl)propyl]-N-(2-naphthylmethyl)carbamoyl]-3-butenoic acid (1) Preparation of methyl 3-tert-butoxycarbonyl-4-hydroxy-4-[N-[(1RS,2RS)-1-methyl-2-(4-nitrophenyl)-3-{5-(phenylcarbamoyl)-2-furyl}propyl]-N-(2-naphthylmethyl)carbamoyl] butanoate 49 mg of tert-butyl (2RS,3RS)-2-(N-[(1RS,2RS)-1-methyl-2-(4-nitrophenyl)-3-{5-(phenylcarbamoyl)-2-furyl) propyl]-N-(2-naphthylmethyl)carbamoyl]-5-oxotetrahydrofuran-3-carboxylate obtained in Example 24(1) was dissolved in a mixed solution of 2 ml of tetrahydrofuran and 0.5 ml of water, and a 1N sodium hydroxide aqueous solution was added thereto, followed by stirring at room temperature for 15 hours. The reaction solution was acidified by an addition of 1N hydrochloric acid and then extracted with ethyl acetate. The extract solution was dried over anhydrous magnesium sulfate. The drying agent was filtered off, and then, a small excess amount of diazomethane was added to the filtrate at room temperature. The solvent was distilled off under reduced pressure, and the residue was purified by silica gel column chromatography (hexane/ethyl acetate=2/1) to obtain 202 mg (yield: 78%) of the above-identified compound as a yellow oily substance.

(2) Preparation of methyl 3-tert-butoxycarbonyl-4-hydroxy-4-[N-[(1RS,2RS)-1-methyl-2-(4-nitrophenyl)-3-(5-(phenylcarbamoyl)-2-furyl}propyl]-N-(2-naphthylmethyl)carbamoyl]-3-butenoate 40 mg of methyl 3-tert-butoxycarbonyl-4-hydroxy-4-[N-[(1RS,2RS)-1-methyl-2-(4-nitrophenyl)-3-(5-(phenylcarbamoyl)-2-furyl)propyl]-N-(2-naphthylmethyl) carbamoyl]butanoate was dissolved in 5 ml of chloroform, and 68 mg of Dess-Martin reagent was added thereto, followed by stirring at room temperature for one hour. The reaction solution was poured into a mixed solution of a saturated sodium hydrogencarbonate aqueous solution and a saturated sodium thiosulfate aqueous solution and extracted with ethyl acetate. The organic layer was washed with a saturated sodium chloride aqueous solution and then dried over anhydrous magnesium sulfate. The drying agent was filtered off, and the solvent was distilled off under reduced pressure. The residue was purified by silica gel thin layer chromatography (Kieselgel™60F$_{254}$, Art™5744; hexane/ethyl acetate=3/2) to obtain 16 mg (yield: 40%) of the above-identified compound as a colorless oily substance.

(3) Preparation of 3-tert-butoxycarbonyl-4-hydroxy-4-[N-[(1RS,2RS)-1-methyl-2-(4-nitrophenyl)-3-(5-(phenylcarbamoyl)-2-furyl}propyl]-N-(2-naphthylmethyl)carbamoyl]-3-butenoic acid 16 mg of methyl 3-tert-butoxycarbonyl-4-hydroxy-4-[N-[(1RS,2RS)-1-methyl-2-(4-nitrophenyl)-3-(5-(phenylcarbamoyl)-2-furyl}propyl]-N-(2-naphthylmethyl)carbamoyl]-3-butenoate was dissolved in a mixed solution of 1 ml of tetrahydrofuran and 0.3 ml of water, and 0.3 ml of a 1N sodium hydroxide aqueous solution was added thereto, followed by stirring at room temperature for 2 days. The reaction solution was acidified by an addition of 1N hydrochloric acid and then extracted with ethyl acetate. The extract solution was dried over anhydrous magnesium sulfate. The drying agent was filtered off, and then, the solvent was distilled off under reduced pressure. The residue was purified by silica gel thin layer chromatography (Kieselgel™60F$_{254}$, Art™5744; chloroform/methanol=8/1) to obtain 7.7 mg (yield: 49%) of the above-identified compound as a colorless foam.

$^1$H-NMR(CDCl$_3$)δ:0.80–1.10(3H, m), 1.40–1.50(9H, m), 2.80–3.40(5H, m), 4.40–5.10(4H, m), 5.45–5.73(1H, m), 6.70–7.00(1H, m), 7.00–8.20(17H, m)

FAB-MS:748(M+H)

Compounds of Examples 26 and 27 were prepared in the same manner as in Example 25 except that instead of N-{(1RS,2RS)-1-methyl-2-(4-nitrophenyl)-3-(5-(phenylcarbamoyl)-2-furyl}propyl}-2-naphthylmethylamine, the corresponding amine derivatives were employed.

Example 26

3-tert-butoxycarbonyl-4-hydroxy-4-(N-[(1RS,2RS)-1-methyl-2-(3,4-methylenedioxyphenyl)-3-{5-(phenylcarbamoyl)-2-furyl)propyl]-N-(2-naphthylmethyl)carbamoyl]-3-butenoic acid $^1$H-NMR(CDCl$_3$)δ:0.80–1.10(3H, m), 1.35–1.55(9H, m), 2.30–3.20(5H, m), 4.25–5.00(4H, m), 5.30–5.90(3H, m), 6.30–6.95(4H, m), 7.05–7.15 and 7.30–7.90(total 13H, each m)

FAB-MS;747(M+H)

Example 27

3-tert-butoxycarbonyl-4-hydroxy-4-[N-{(1RS,2RS)-1-methyl-2-(4-nitrophenyl)-3-(3-phenoxymethylphenyl)propyl}-N-(2-naphthylmethyl)carbamoyl]-3-butenoic acid $^1$H-NMR(CDCl$_3$)δ:0.82–1.10(3H, m), 1.39–1.58(9H, m), 2.29–3.32(5H, m), 4.38–5.02(6H, m), 6.12–8.02(20H, m)

FAB-MS:745(M+H)

Example 28

Preparation of 4-hydroxy-3-methoxycarbonyl-4-[N-[(1RS,2RS)-1-methyl-2-(3,4-methylenedioxyphenyl)-3-(5-(phenylcarbamoyl)-2-furyl}propyl]-N-(2-naphthylmethyl)carbamoyl]-3-butenoic acid 89 mg of disodium (3RS,4RS)-4-(N-[(1RS,2RS)-1-methyl-2-(3,4-methylenedioxyphenyl)-3-{5-(phenylcarbamoyl)-2-furyl}propyl]-N-(2-naphthylmethyl)carbamoyl]-3-carboxylato-4-hydroxybutanoate obtained in the same manner as in Example 24 except that instead of N-{(1RS,2RS)-1-methyl-2-(4-nitrophenyl)-3-{5-(phenylcarbamoyl)-2-furyl}propyl}-2-naphthylmethylamine used as the starting material in Example 24, N-{(1RS,2RS)-1-methyl-2-(3,4-methylenedioxyphenyl)-3-{5-(phenylcarbamoyl)-2-furyl}propyl}-2-naphthylmethylamine was employed, was dissolved in water. The solution was acidified by an addition of 1N hydrochloric acid and extracted with ethyl acetate. The extract solution was dried over anhydrous magnesium sulfate. The drying agent was filtered off, and then, the solvent was distilled off under reduced pressure. The residue was dissolved in 2 ml of ethyl acetate, and a small excess amount of diazomethane was added thereto. Then, the solvent was distilled off under reduced pressure. The residue was purified by silica gel column chromatography (hexane/ethyl acetate=2/1+1/1), and the obtained dimethyl ester was treated in the same manner as in Example 25(2) and (3) to obtain 13 mg (yield: 15%) of the above-identified compound as a colorless oily substance.

$^1$H-NMR(CDCl$_3$)δ:0.95–1.15(3H, m), 2.80–3.30(5H, m), 3.65–3.90(3H, m), 4.20–4.90(4H, m), 5.45–5.55 and 5.65–5.95(total 3H, each m), 6.35–7.00(4H, m), 7.05–7.15 and 7.25–7.90(13H, each m)

FAB-MS:705(M+H)

Example 29

Preparation of 3-allyloxycarbonyl-4-hydroxy-4-[N-[(1RS,2RS)-1-methyl-2-(3,4-methylenedioxyphenyl)-3-{5-(phenylcarbamoyl)-2-furyl}propyl]-N-(2-naphthylmethyl)carbamoyl]-3-butenoic acid 80 mg of disodium (3RS,4RS)-4-[N-[(1RS,2RS)-1-methyl-2-(3,4-methylenedioxyphenyl)-3-{5-(phenylcarbamoyl)-2-furyl}propyl]-N-(2-naphthylmethyl)carbamoyl]-3-carboxylato-4-hydroxybutanoate as the starting material of Example 28, was dissolved in 2 ml of dimethylformamide, and 37 μl of allyl bromide was added thereto, followed by stirring at room temperature for 3 days. The reaction solution was poured into water and extracted with ethyl ether and then dried over anhydrous magnesium sulfate. The drying agent was filtered off, and then, the solvent was distilled off under reduced pressure. The residue was purified by silica gel column chromatography (hexane/ethyl acetate=3/2), and the obtained diallyl ester was treated in the same manner as in Example 25(2) and (3) to obtain 4.4 mg (yield: 2.4%) of the above-identified compound as a colorless oily substance.

$^1$H-NMR(CDCl$_3$)δ:0.80–1.10(3H, m), 2.50–3.30(5H, m), 4.20–4.95(6H, m), 5.20–5.55(2H, m), 5.70–6.00(3H, m), 6.35–7.00(5H, m), 7.05–7.15 and 7.25–8.00(13H, m)

FAB-MS:731(M+H)

Example 30

Preparation of 5-hydroxy-4-isopropoxycarbonyl-5-[N-[(1RS,2RS)-1-methyl-2-(4-nitrophenyl)-3-{5-(phenylcarbamoyl)-2-furyl}propyl]-N-(2-naphthylmethyl)carbamoyl]-4-pentenoic acid (1) Preparation of isopropyl 5-hydroxy-4-isopropoxycarbonyl-5-[N-[(1RS,2RS)-1-methyl-2-(4-nitrophenyl)-3-(5-(phenylcarbamoyl)-2-furyl}propyl]-N-(2-naphthylmethyl)carbamoyl] pentanoate 99 mg of isopropyl 5-acetoxy-4-isopropoxycarbonyl-5-[N-[(1RS,2RS)-1-methyl-2-(4-nitrophenyl)-3-{5-

(phenylcarbamoyl)-2-furyl}propyl]-N-(2-naphthylmethyl) carbamoyl]pentanoate obtained by subjecting N-{(1RS, 2RS)-1-methyl-2-(4-nitrophenyl)3-{5-(phenylcarbamoyl)-2-furyl}propyl]-2-naphthylmethylamine obtained in Example 23(1) and 2,4-diisopropyl 1-acetoxy-1,2,4-butanetricarboxylate obtained in Reference Example 5 to a condensation reaction in accordance with the method of Example 24(1), was dissolved in 3 ml of isopropanol, and 9.8 mg of sodium isopropoxide was added thereto, followed by stirring at room temperature for one hour. The reaction solution was poured into water and extracted with ethyl acetate. Then, the organic layer was dried over anhydrous magnesium sulfate. The drying agent was filtered off, and then, the solvent was distilled off under reduced pressure. The residue was purified by silica gel column chromatography (hexane/ethyl acetate=2/1) to obtain 43 mg (yield: 45%) of the above-identified compound.

(2) Preparation of 5-hydroxy-4-isopropoxycarbonyl-5-[N-[(1RS,2RS)-1-methyl-2-(4-nitrophenyl)-3-{5-(phenylcarbamoyl)-2-furyl}propyl]-N-(2-naphthylmethyl)carbamoyl]-4-pentenoic acid Isopropyl 5-hydroxy-4-isopropoxycarbonyl-5-[N-[(1RS,2RS)-1-methyl-2-(4-nitrophenyl)-3-{5-(phenylcarbamoyl)-2-furyl}propyl]-N-(2-naphthylmethyl)carbamoyl] pentanoate was treated in the same manner as in Example 25(2) and (3) to obtain the above-identified compound as a colorless oily substance.

$^1$H-NMR(CDCl$_3$)δ:0.82–1.00(3H, m), 1.17–1.35(6H, m), 2.10–3.80(7H, m), 4.10–5.16(5H, m), 5.49–5.73(1H, m), 6.78–6.94(1H, m), 7.06–8.22(17H, m)

FAB-MS:748(M+H)

Example 31

Preparation of 3-tert-butoxycarbonyl-4-[N-(2,3-dichlorobenzyl)-N-[(1RS,2RS)-1-methyl-2-(4-nitrophenyl)-3-{5-(phenylcarbamoyl)-2-furyl}propyl]carbamoyl]-4-hydroxy-3-butenoic acid Tert-butyl (3RS,4RS)-5-[N-[(1RS,2RS)-1-methyl-2-(4-nitrophenyl)-3-{5-(phenylcarbamoyl)-2-furyl}propyl]-N-(2,3-dichlorobenzyl)carbamoyl]-2-oxotetrahydrofuran-4-carboxylate obtained in the same manner as in Example 24(1) except that instead of N-[(1RS,2RS)-1-methyl-2-(4-nitrophenyl)-3-{5-(phenylcarbamoyl)-2-furyl}propyl]-2-naphthylmethylamine used as the starting material in Example 24, the corresponding amine derivative was used, was treated in the same manner as in Example 25(2) and (3) to obtain the above-identified compound as a colorless oily substance.

$^1$H-NMR(CDCl$_3$)δ:0.80–1.10(3H, m), 1.20–1.50(9H, m), 2.75–3.20 and 3.55–3.75(total 5H, m), 4.30–5.00(4H, m), 5.55–5.95(1H, m), 6.90–7.00(1H, m), 7.00–7.70 and 8.10–8.20(total 13H, m)

FAB-MS:768(M+H)

Reference Example 1

Preparation of ethyl 5-{(2RS,3RS)-3-(2-naphthylmethylamino)-2-(4-nitrophenyl)butyl}-2-furancarboxylate (1) Preparation of ethyl 5-{2-(4-nitrophenyl)-3-oxobutyl}-2-furancarboxylate 3.00 g of p-nitrophenylacetone was dissolved in 50 ml of dimethylformamide, and 0.70 g of 60% oily sodium hydride was added under cooling with ice with stirring, followed by stirring at the same temperature for 10 minutes. 5 ml of a dimethylformamide solution containing 3.40 g of ethyl 5-chloromethyl-2-furancarboxylate, and 3.05 g of potassium iodide were added thereto, followed by stirring at room temperature for 2.5 hours. Then, the reaction solution was acidified by an addition of acetic acid. Water and ethyl ether were added, and the mixture was extracted. Then, the organic layer was washed with a saturated sodium chloride aqueous solution and dried over anhydrous magnesium sulfate. The drying agent was filtered off, and then, the solvent was distilled off under reduced pressure. The residue was purified by silica gel column chromatography (hexane/ethyl acetate=5/1+2/1) to obtain 5.48 g of the above-identified compound.

(2) Preparation of ethyl 5-{(2RS,3SR)-3-hydroxy-2-(4-nitrophenyl)butyl}-2-furancarboxylate 5.48 g of ethyl 5-(2-(4-nitrophenyl)-3-oxobutyl)-2-furancarboxylate was dissolved in 50 ml of tetrahydrofuran, and 16.5 ml of a 1M tetrahydrofuran solution of lithium tri-sec-butylborohydride was added under cooling to −78° C. with stirring, followed by stirring at the same temperature for 2 hours. Water was added to the reaction solution, followed by stirring at room temperature for 30 minutes. Then, the solution was acidified by an addition of acetic acid. Ethyl acetate was added thereto for extraction. The organic layer was washed with a saturated sodium chloride aqueous solution and then dried over anhydrous magnesium sulfate. The drying agent was filtered off, and then, the solvent was distilled off under reduced pressure. The residue was purified by silica gel column chromatography (hexane/ethyl acetate=5/1+1/1) to obtain 3.66 g of the above-identified compound.

(3) Preparation of ethyl 5-{(2RS,3RS)-3-azido-2-(4-nitrophenyl)butyl}-2-furancarboxylate 3.66 g of ethyl 5-{(2RS,3SR)-3-hydroxy-2-(4-nitrophenyl)butyl}-2-furancarboxylate was dissolved in 40 ml of tetrahydrofuran, and 4.32 g of triphenylphosphine, 2.60 ml of diethyl azodicarboxylate and 4.53 g of diphenylphosphoryl azide were added under cooling with ice with stirring, followed by stirring at room temperature for 18 hours. The reaction solution was evaporated to dryness under reduced pressure. Then, the residue was purified by silica gel column chromatography (hexane/ethyl acetate=50/1) to obtain 3.24 g of the above-identified compound.

(4) Preparation of ethyl 5-{(2RS,3RS)-3-amino-2-(4-nitrophenyl)butyl}-2-furancarboxylate 3.24 g of ethyl 5-{(2RS,3RS)-3-azido-2-(4-nitrophenyl)butyl}-2-furancarboxylate was dissolved in a mixed solution of 50 ml of tetrahydrofuran and 5 ml of water, and 2.37 g of triphenylphosphine was added thereto, followed by heating and refluxing for 6 hours. The reaction solution was left to cool to room temperature, and then ethyl ether and water were added thereto for extraction. The organic layer was washed with a saturated sodium chloride aqueous solution and then dried over anhydrous magnesium sulfate. The drying agent was filtered off, and then, the solvent was distilled off under reduced pressure. The residue was purified by silica gel column chromatography (methylene chloride/methanol=100/1+20/1) to obtain 2.89 g of the above-identified compound.

(5) Preparation of ethyl 5-{(2RS,3RS)-3-(2-naphthylmethylamino)-2-(4-nitrophenyl)butyl}-2-furancarboxylate 0.97 g of ethyl 5-{(2RS,3RS)-3-amino-2-(4-nitrophenyl) butyl}-2-furancarboxylate was dissolved in 10 ml of methanol, and 0.48 g of 2-naphthoaldehyde was added thereto, followed by heating under reflux for 1.5 hours. The reaction solution was left to cool to room temperature. Then, 0.16 g of sodium borohydride was added thereto, followed by stirring at room temperature for 15 minutes. Water and ethyl acetate were added to the reaction solution for extraction. The organic layer was washed with a saturated sodium chloride aqueous solution and then dried over anhydrous magnesium sulfate. The drying agent was filtered off, and then, the solvent was distilled off under reduced pressure. The residue was purified by silica gel column chromatography (hexane/ethyl acetate=4/1) to obtain 1.15 g of the above-identified compound.

The reactions were carried out in the same manner as in Reference Example 1 except that instead of p-nitrophenylacetone and/or ethyl 5-chloromethyl-2-furancarboxylate and/or 2-naphthoaldehyde used as the starting material in the above reaction, the corresponding arylacetone derivative and/or halide and/or arylaldehyde derivative was used, to obtain ethyl 5-{(2RS,3RS)-2-(4-chlorophenyl)-3-(2-naphthylmethylamino)butyl}-2-furancarboxylate, ethyl 3-{(2RS,3RS)-2-(4-chlorophenyl)-3-(2-naphthylmethylamino)butyl]benzoate, ethyl 5-{(2RS,3RS)-2-(4-chlorophenyl)-3-(2-naphthylmethylamino)butyl}-3-isoxazolecarboxylate, ethyl 2-{(2RS,3RS)-2-(4-chlorophenyl)-3-(2-naphthylmethylamino)butyl}-5-pyridinecarboxylate, ethyl 5-{(2RS,3RS)-3-(2-benzo[b]thienylmethylamino)-2-(3,4-methylenedioxyphenyl)butyl}-2-furancarboxylate, N-{1RS,2RS)-2-(4-methoxycarbonylphenyl)-1-methyl-3-(3-phenoxymethylphenyl)propyl}-2-naphthylmethylamine, N-[(1RS,2RS)-2-(4-methoxycarbonylphenyl)-1-methyl-3-{5-(phenoxymethyl)-3-(1,2,4-oxadiazolyl)}propyl]-2-naphthylmethylamine, N-{(1RS,2RS)-2-(4-methoxycarbonylphenyl)-1-methyl-3-{(E)-3-styrylphenyl}propyl]-2-naphthylmethylamine, N-{(1RS,2RS)-2-(4-chlorophenyl)-1-methyl-3-{(E)-3-styrylphenyl}propyl]-2-naphthylmethylamine, N-{(1RS,2RS)-2-(4-methoxycarbonylphenyl)-1-methyl-3-(5-phenoxymethyl-2-furyl)propyl}-2-naphthylmethylamine and ethyl 5-{(2RS,3RS)-2-(4-nitrophenyl)-3-(2,3-dichlorobenzylamino)butyl}-2-furancarboxylate.

Reference Example 2

Preparation of 1,2-di-tert-butyl 1,2,3-propanetricarboxylate and its optical resolution 13.1 ml of a 1.5M cyclohexane solution of lithium diisopropylamide was dissolved in 10 ml of tetrahydrofuran, and a tetrahydrofuran solution (10 ml) containing 2.96 g of benzyl acetate was added under cooling to –70° C. with stirring, followed by stirring at the same temperature for 30 minutes. Then, a tetrahydrofuran solution (10 ml) containing 2.96 g of di-tert-butyl maleate, was dropwise added thereto, followed by stirring at the same temperature for 30 minutes. The reaction solution was extracted by an addition of 20 ml of water and 50 ml of ethyl ether. The organic layer was separated, then washed with a saturated sodium chloride aqueous solution and dried over anhydrous magnesium sulfate. Then, the solvent was distilled off under reduced pressure. The residue was dissolved in 50 ml of dioxane, and 0.4 g of a 10% palladium carbon catalyst was added thereto, followed by catalytic reduction for 20 hours at room temperature under hydrogen atmospheric pressure. The catalyst was filtered off, and then, the solvent was distilled off under reduced pressure. The residue was treated with hexane, whereupon the precipitate thereby obtained was collected by filtration and then dried to obtain 3.02 g of the above-identified compound as colorless crystalline powder, mp 55–57° C.

12.97 g of the di-tert-butyl ester thus obtained and 13.24 g of cinchonidine was dissolved under heating in le of carbon tetrachloride. Then, seed crystals were added thereto, and the mixture was left to stand at room temperature for 24 hours. The crystals were collected by filtration and then again dissolved under heating in 1l of carbon tetrachloride, and seed crystals were added thereto, and the mixture was left to stand for 24 hours. This operation was further repeated twice to obtain 6.66 g of a cinchonidine salt of the above-identified compound, which is named as the (S*)-isomer for the sake of convenience, $[\alpha]_D^{20}$–62.7° (c 1.0, chloroform).

The cinchonidine salt thus obtained was dissolved in a mixed solution of ethyl ether and 1N hydrochloric acid under cooling with ice, and the organic layer was separated and then post-treated in accordance with a conventional method to obtain the (S*)-isomer of the above-identified compound as colorless oily substance, $[a]_D^{20}$+4.44° (c 0.92, chloroform).

The fraction containing a large amount of the other mirror image isomer obtained in the above optical resolution operation, was converted to a free acid, and then, the same operation was carried out in isopropyl ether using quinine, whereby the mirror image isomer named as the (R*)-isomer for the sake of convenience, was obtained.

Reference Example 3

Preparation of N-{(1RS,2RS)-2-(4-chlorophenyl)-1-methyl-3-(4-phenylethynylphenyl)propyl}-2-naphthylmethylamine 1.54 g of (2RS,3SR)-4-(4-bromophenyl)-3-(4-chlorophenyl)-2-butanol (prepared in the same manner as in Reference Example 1) was dissolved in 45 ml of dimethylformamide, and 1.4 g of tert-butyldimethylsilyl chloride and 1.2 g of imidazole were added thereto, followed by stirring at room temperature for one hour. Ethyl ether and water were added to the reaction solution for extraction. The organic layer was washed with a saturated sodium chloride aqueous solution and then dried over anhydrous magnesium sulfate. The drying agent was filtered off, and then, the solvent was distilled off under reduced pressure. The residue was purified by silica gel column chromatography (hexane/ethyl acetate=15/1) to obtain 2.02 g (yield: 99%) of (2RS, 3SR)-4-(4-bromophenyl)-2-(tert-butyldimethylsilyloxy)-3-(4-chlorophenyl)butane.

200 mg of the silyl-protected compound thereby obtained was dissolved in 10 ml of toluene, and 400 mg of tributyl (phenylethynyl)tin and 44 mg of tetrakis (triphenylphosphine)palladium were added thereto, followed by heating and refluxing for 5 hours. A potassium fluoride aqueous solution and ethyl ether were added to the reaction solution and thoroughly mixed by shaking. Then, the organic layer was separated, washed with a saturated sodium chloride aqueous solution and then dried over anhydrous sodium sulfate. The drying agent was filtered off, and then, the solvent was distilled off under reduced pressure. The residue was dissolved in 5 ml of tetrahydrofuran, and 2 ml of a 1M tetrahydrofuran solution of tetrabutylammonium fluoride was added thereto, followed by stirring at room temperature for 7 hours. A saturated ammonium chloride aqueous solution and ethyl acetate were added to the reaction solution for extraction. The organic layer was washed with a saturated sodium chloride aqueous solution and then dried over anhydrous magnesium sulfate. The drying agent was filtered off, and then, the solvent was distilled off under reduced pressure. The residue was purified by silica gel column chromatography (hexane/ethyl acetate=10/1) to obtain 141 mg (yield: 89%) of (2RS,3SR)-3-(4-chlorophenyl)-4-(4-phenylethynylphenyl)-2-butanol.

141 mg of the alcohol compound thus obtained was dissolved in 2 ml of ethyl acetate, and 62 μl of methanesulfonyl chloride and 161 μl of triethylamine were added thereto, followed by stirring at room temperature for 30 minutes. Insoluble precipitates were filtered off from the reaction solution. Then, the filtrate was concentrated under reduced pressure, and the residue was dissolved in 5 ml of dimethylformamide. Then, 255 mg of sodium azide was added thereto, followed by heating at 80° C. for 4 hours. The reaction solution was left to cool to room temperature. Then, ethyl ether and water were added thereto for extraction. The organic layer was washed with a saturated sodium chloride aqueous solution and then dried over anhydrous magnesium sulfate. The drying agent was filtered off, and then, the solvent was distilled off under reduced pressure. The residue was heated and refluxed together with 187 mg of triphenylphosphine in 7 ml of 10%-water containing tetrahydrofuran for one hour. The reaction solution was evaporated to dryness under reduced pressure. Then, the residue was dissolved in ethanol and again evaporated to dryness under reduced pressure. The obtained residue was purified by silica gel column chromatography (chloroform/methanol=50/1+10/1) to obtain 129 mg (yield: 92%) of (1RS,2SR)-2-(4-chlorophenyl)-1-methyl-3-(4-phenylethynylphenyl)propylamine.

38 mg of the amine compound thus obtained was dissolved in 1 ml of methanol, and 20 mg of 2-naphthoaldehyde was added thereto, followed by heating and refluxing for 6 hours. The reaction solution was left to cool to room temperature, and then, 5 mg of sodium borohydride was added thereto, followed by stirring at room temperature for 30 minutes. A saturated ammonium chloride aqueous solution and ethyl ether were added to the reaction solution for extraction. The organic layer was washed with a saturated sodium chloride aqueous solution and then dried over anhydrous magnesium sulfate. The drying agent was filtered off, and then, the solvent was distilled off under reduced pressure. The residue was purified by silica gel thin layer chromatography (hexane/ethyl acetate=4/1) to obtain 22 mg (yield: 42%) of the above-identified compound.

The reaction was carried out in the same manner as in Reference Example 3 except that instead of tributyl (phenylethynyl)tin used as the starting material in the above reaction, tributyl(styryl)tin was employed, to obtain N-{(1RS,2RS)-2-(4-chlorophenyl)-1-methyl-3-(3-styrylphenyl)propyl}-2-naphthylmethylamine.

Reference Example 4

Preparation of (2RS,3RS)-3-tert-butoxycarbonyl-5-oxotetrahydrofuran-2-carboxylic acid (1) Preparation of (2RS,3SR)-2-benzyloxycarbonyl-5-oxotetrahydrofuran-3-carboxylic acid 5.3 g of (2RS,3SR)-5-oxotetrahydrofuran-2,3-dicarboxylic acid was dissolved in 90 ml of acetone, and 6.6 g of N,N'-dicyclohexylcarbodiimide was added thereto, followed by stirring at room temperature for 2.5 hours. 3.3 ml of benzyl alcohol was added to the reaction solution, followed by stirring at the same temperature for 2 days. Insoluble matters were filtered off, and then the filtrate was concentrated under reduced pressure. The residue was purified by silica gel column chromatography (hexane/ethyl acetate=4/1+chloroform/methanol=50/1) to obtain 6.55 g of the above-identified compound as a yellow solid.

(2) Preparation of 2-benzyl 3-tert-butyl (2RS,3RS)-5-oxotetrahydrofuran-2,3-dicarboxylate 6.53 g of (2RS,3SR)-2-benzyloxycarbonyl-5-oxotetrahydrofuran-3-carboxylic acid was dissolved in 70 ml of chloroform, and 4.53 g of 4-dimethylaminopyridine, 7.11 g of 1-ethyl-3-(3-dimethylaminopropyl)carbodiimide hydrochloride and 4.70 ml of tert-butyl alcohol were sequentially added thereto, followed by stirring at room temperature for 14 hours. The reaction solution was poured into 1N hydrochloric acid cooled with ice and extracted with ethyl acetate. The organic layer was dried over anhydrous magnesium sulfate, and the drying agent was filtered off. Then, the solvent was distilled off under reduced pressure. The residue was purified by silica gel column chromatography (hexane/ethyl acetate=5/1), to obtain 5.16 g of the above-identified compound as a white solid.

(3) Preparation of (2RS,3RS)-3-tert-butoxycarbonyl-5-oxotetrahydrofuran-2-carboxylic acid 4.92 g of 2-benzyl 3-tert-butyl (2RS,3RS)-2-oxotetrahydrofuran-2,3-dicarboxylate was dissolved in 50 ml of ethyl acetate, and 500 mg of a 10% palladium-carbon catalyst was added thereto, followed by catalytic reduction at room temperature under hydrogen atmospheric pressure for 3 hours. The catalyst was filtered off, and then, the filtrate was evaporated to dryness under reduced pressure to obtain 3.44 g of the above-identified compound as a white solid.

Reference Example 5

Preparation of 2,4-diisopropyl 1-acetoxy-1,2,4-butanetricarboxylate (1) Preparation of diisopropyl 4-hydroxy-4-phenyl-1,3-butanedicarboxylate 38 ml of a 1.5M lithium diisopropylamide cyclohexane solution was dissolved in 400 ml of tetrahydrofuran, and 20 ml of a tetrahydrofuran solution containing 10.3 g of diisopropyl glutarate was dropwise added at −78° C. in a nitrogen atmosphere. After stirring at the same temperature for 30 minutes, 10 ml of a tetrahydrofuran solution containing 3.9 g of benzaldehyde was dropwise added thereto, followed by stirring at −78° C. for 1.5 hours. 2N hydrochloric acid was added to the reaction solution, and the temperature was brought to room temperature. Then, the mixture was extracted with ethyl acetate. The organic layer was washed with 1N hydrochloric acid, a saturated sodium hydrogencarbonate aqueous solution and a saturated sodium chloride aqueous solution and dried over anhydrous magnesium sulfate. The drying agent was filtered off, and then, the solvent was distilled off under reduced pressure. The residue was purified by silica gel column chromatography (hexane/ethyl acetate=5/1+3/1) to obtain 6.14 g of the above-identified compound as a colorless oily substance.

(2) Preparation of diisopropyl 4-acetoxy-4-phenyl-1,3-butanedicarboxylate 70 mg of dimethylaminopyridine was added to a mixed solution comprising 6.13 g of diisopropyl 4-hydroxy-4- phenyl-1,3-butanedicarboxylate, 30 ml of pyridine and 6 ml of acetic anhydride, followed by stirring at room temperature for 1.5 hours. 2N hydrochloric acid was added to the reaction solution, and then the mixture was extracted with ethyl acetate. The organic layer was sequentially washed with 2N hydrochloric acid, a saturated sodium hydrogencarbonate aqueous solution and a saturated sodium chloride aqueous solution and dried over anhydrous magnesium sulfate. The drying agent was filtered off, and then, the solvent was distilled off under reduced pressure. The residue was purified by silica gel column chromatography (hexane/ethyl acetate=5/1) to obtain 4.68 g of the above-identified compound as a colorless oily substance.

(3) Preparation of 2,4-diisopropyl 1-acetoxy-1,2,4-butanetricarboxylate 4.68 g of diisopropyl 4-acetoxy-4-phenyl-1,3-butanedicarboxylate was dissolved in a mixed solution of 20 ml of carbon tetrachloride, 20 ml of acetonitrile and 20 ml of water, and 9.7 g of disodium phosphate 12 hydrate and 11.2 g of sodium periodate were added thereto. Then, 58 mg of ruthenium chloride was added thereto under cooling with ice, followed by stirring at room temperature for 3 days. Insoluble matters were filtered and then washed with a saturated sodium hydrogencarbonate aqueous solution and chloroform. The filtrate and the washed solution were put together, and then the aqueous layer was separated. The obtained aqueous layer was acidified with 6N hydrochloric acid and then extracted with ethyl ether. The organic layer was washed with a saturated sodium thiosulfate aqueous solution and a saturated sodium chloride aqueous solution and then dried over anhydrous magnesium sulfate. The drying agent was filtered off, and then, the solvent was distilled off under reduced pressure to obtain 1.58 g of the above-identified compound as a colorless oily substance.

INDUSTRIAL APPLICABILITY

The compounds of the present invention have excellent inhibitory activities against protein-farnesyl transferase (PFT) and thus are useful as antitumor agents.

We claim:

1. A compound of the formula (I) or a pharmaceutically acceptable salt or ester thereof:

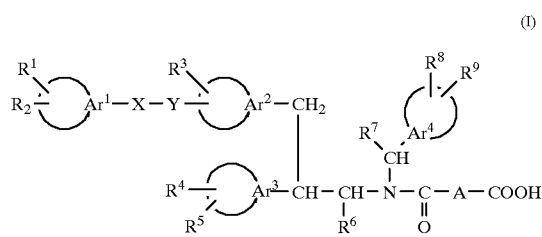

wherein each of

which are the same or different, is selected from the group consisting of phenyl, naphthyl and anthryl, and a heteroaromatic ring group which is a 5- or 6-membered monocyclic ring which contains —O—, —S— or —N—; A is a $C_{2-9}$ saturated or unsaturated aliphatic hydrocarbon group which is unsubstituted or substituted by lower alkyl, hydroxyl, lower hydroxyalkyl, lower alkoxy, carboxyl, lower carboxyalkyl, phenyl, naphthyl or anthryl or alkyl-substituted phenyl, naphthyl or anthryl; —X—Y— is selected from the group consisting of —O—CHR$^a$— and CHR$^a$—O, wherein R$^a$ is hydrogen or lower alyl; each of R$^1$, R$^2$, R$^3$, R$^8$ and R$^9$ which are the same or different, is hydrogen, halogen, hydroxyl, lower alkyl or lower alkoxy; each of R$^4$ and R$^5$, which are the same or different is hydrogen, halogen, hydroxyl, amino, nitro, cyano, carboxyl, lower alkoxycarbonyl, carbomoyl, lower alkyl carbomoyl, lower alkyl, lower hydroxyalkyl, lower fluoroalkyl or lower alkoxy; R$^6$ is lower alkyl; and R$^7$ is hydrogen or lower alkyl.

2. The compound of claim 1, wherein A is a group of the formula.

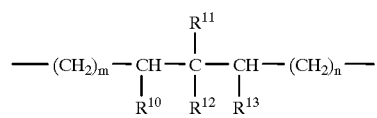

wherein R$^{10}$ is hydrogen, hydroxyl, lower hydroxyalkyl, lower alkoxy or carboxyl; R$^{11}$ is hydrogen, hydroxyl, lower alkoxy, carboxyl or lower carboxyalkyl; R$^{12}$ is hydrogen, lower hydroxyalkyl or carboxyl; R$^{13}$ is hydrogen, hydroxyl or carboxyl; and each of m and n which are the same or different is an integer of from 0 to 2.

3. The compound of claim 1, wherein A is a group of the formula:

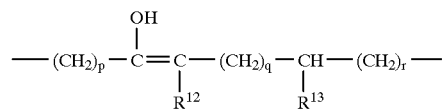

wherein R$^{12}$ is hydrogen, lower hydroxyalkyl or carboxyl; R$^{13}$ is hydrogen, hydroxyl or carboxyl; p is 0 or 1, and each of q and r which are the same or different, is an integer of from 0to2.

4. The compound of claim 1, wherein

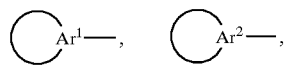

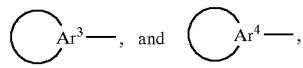

which are the same or different, is selected from the group consisting of phenyl, naphthyl and anthryl.

5. The compound of claim 1, wherein each of

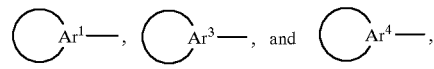

which are the same or different, is selected from the group consisting of phenyl, naphthyl and anthryl; and

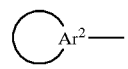

and is a heteroaromatic ring group which is a 5- or 6-membered monocyclic ring which contains —O—, —S— or —N—.

6. The compound of claim 1, wherein each of

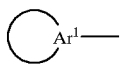

Ar is a heteroaromatic ring group which is a 5- or 6-membered monocyclic ring which contains —O—, —S— or —N—; and each of

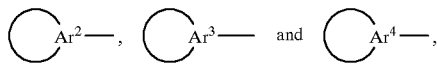

which are the same or different, is selected from the group consisting of phenyl, naphthyl and anthryl.

7. The compound of claim 1, wherein

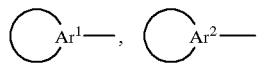

which are the same or different, is a heteroaromatic ring group which is a 5- or 6-membered monocyclic ring which contains —O—, —S— or —N—; and each of

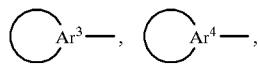

which are the same or different, is selected from the group consisting of phenyl, naphthyl and anthryl.

8. The compound of claim 1, wherein said heteroaromatic ring group which is a 5- or 6-membered monocyclic ring which contains —O—, —S— or —N— is selected from the group consisting of pyrrolyl, imidazolyl, pyrazolyl, pyridyl, pyrazinyl, pyrimidinyl, pyridazinyl, oxazolyl, isoxazolyl, furyl, thenyl, thiazolyl and isothiazolyl.

9. The compound of claim 8, wherein said heteroaromatic ring group which is a 5- or 6-membered monocyclic ring which contains —O—, —S— or —N— is selected from the group consisting of furyl, thienyl, pyridyl, pyrimidinyl. oxazolyl, isoxazolyl and thiazolyl.

10. The compound of claim 1, wherein each of $R^2$ and $R^1$–$R^9$ is lower alkyl and each is selected for the group consisting of methyl ethyl.

11. The compound of claim 1, wherein lower hydroxyalkyl for either $R^4$ or $R^5$ is hydroxymethyl or hydroxyethyl.

12. The compound of claim 1, wherein each of $R^1$–$R^5$, $R^8$ and $R^9$ is lower alkoxy and each is selected from the group consisting of methoxy, ethoxy and methylenedioxy.

13. The compound of claim 1, wherein lower fluoroalkyl for either $R^4$ or $R^5$ is fluoromethyl, difluoromethyl, trifluoromethyl, 1-fluoromethyl, 2-fluoroethyl, 2,2,2-trifluoroethyl or pentafluoroethyl.

14. An anti-tumor agent, which comprises a compound of claim 1, or a pharmaceutically acceptable salt or ester thereof, and a pharmaceutically acceptable excipient.

* * * * *